United States Patent
Blizzard et al.

(10) Patent No.: US 11,779,536 B2
(45) Date of Patent: *Oct. 10, 2023

(54) SUSTAINED RELEASE BIODEGRADABLE INTRACANALICULAR INSERTS COMPRISING A HYDROGEL AND CYCLOSPORINE

(71) Applicant: Ocular Therapeutix, Inc., Bedford, MA (US)

(72) Inventors: Charles D. Blizzard, Nashua, NH (US); Rami El-Hayek, Norwood, MA (US); Michael Goldstein, Cambridge, MA (US); Peter Jarrett, Burlington, MA (US); Andrew Vanslette, Bolton, MA (US)

(73) Assignee: Ocular Therapeutix, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/681,238

(22) Filed: Feb. 25, 2022

(65) Prior Publication Data

US 2022/0202706 A1     Jun. 30, 2022

Related U.S. Application Data

(63) Continuation of application No. 17/483,220, filed on Sep. 23, 2021, now Pat. No. 11,331,267.

(60) Provisional application No. 63/124,204, filed on Dec. 11, 2020, provisional application No. 63/082,505, filed on Sep. 24, 2020.

(51) Int. Cl.
| | |
|---|---|
| *A61K 9/00* | (2006.01) |
| *A61K 38/13* | (2006.01) |
| *A61K 47/10* | (2017.01) |
| *A61K 47/22* | (2006.01) |
| *A61P 27/02* | (2006.01) |

(52) U.S. Cl.
CPC ............ *A61K 9/0051* (2013.01); *A61K 38/13* (2013.01); *A61K 47/10* (2013.01); *A61K 47/22* (2013.01); *A61P 27/02* (2018.01)

(58) Field of Classification Search
CPC ....... A61P 27/02; A61K 9/0051; A61K 38/13; A61K 47/10; A61K 47/22
See application file for complete search history.

(56) References Cited

U.S. PATENT DOCUMENTS

| | | | |
|---|---|---|---|
| 3,993,071 A | 11/1976 | Higuchi et al. | |
| 4,915,684 A | 4/1990 | MacKeen et al. | |
| 5,469,867 A | 11/1995 | Schmitt | |
| 5,902,598 A | 5/1999 | Chen et al. | |
| 6,027,470 A | 2/2000 | Mendius | |
| 6,509,327 B1 | 1/2003 | Cagle et al. | |
| 6,646,001 B2 | 11/2003 | Dellberg et al. | |
| 6,982,090 B2 | 6/2006 | Gillespie | |
| 8,409,606 B2 * | 4/2013 | Sawhney | ............. A61K 31/437 264/118 |
| 8,512,738 B2 | 8/2013 | Hughes et al. | |
| 8,512,749 B2 | 8/2013 | Edelman et al. | |
| 8,535,705 B2 | 9/2013 | Edelman et al. | |
| 8,563,027 B2 | 10/2013 | Sawhney et al. | |
| 8,961,501 B2 | 2/2015 | Jarrett et al. | |
| 9,125,807 B2 | 9/2015 | Sawhney et al. | |
| 9,205,150 B2 | 12/2015 | El-Hayek et al. | |
| 9,254,267 B2 | 2/2016 | Sawhney | |
| 9,370,485 B2 | 6/2016 | Sawhney et al. | |
| 9,463,114 B2 | 10/2016 | Odrich et al. | |
| 9,775,906 B2 | 10/2017 | Sawhney et al. | |
| 9,849,082 B2 | 12/2017 | de Juan, Jr. et al. | |
| 10,226,417 B2 | 3/2019 | Jarrett et al. | |
| 10,251,954 B2 | 4/2019 | Sawhney et al. | |
| 10,300,014 B2 | 5/2019 | de Juan, Jr. et al. | |
| 10,420,724 B2 | 9/2019 | Jarrett et al. | |
| 10,603,274 B2 * | 3/2020 | Utkhede | ............... A61K 9/0051 |
| 10,617,563 B2 | 4/2020 | Jarrett et al. | |
| 10,786,462 B2 | 9/2020 | Jarrett et al. | |
| 10,874,606 B2 | 12/2020 | de Juan, Jr. et al. | |
| 10,905,765 B2 | 2/2021 | Jarrett et al. | |
| 11,291,627 B1 * | 4/2022 | Blizzard | ................. A61K 47/34 |
| 11,331,267 B2 * | 5/2022 | Blizzard | ................. A61P 27/00 |
| 2002/0169409 A1 | 11/2002 | Gillespie | |
| 2003/0065060 A1 | 4/2003 | Qvist et al. | |
| 2003/0108511 A1 | 6/2003 | Sawhney | |
| 2005/0197614 A1 | 9/2005 | Pritchard et al. | |
| 2005/0232972 A1 | 10/2005 | Odrich | |
| 2005/0283109 A1 | 12/2005 | Peyman | |

(Continued)

FOREIGN PATENT DOCUMENTS

| | | | |
|---|---|---|---|
| WO | 2008/017122 | 2/2008 | |
| WO | WO-2008017122 A1 * | 2/2008 | ....... A61K 47/48253 |

(Continued)

OTHER PUBLICATIONS

Lisa M Kaminskas, et al, Characterisation and Tumor Targeting of PEGylated Polylysine Dendrimers Bearing Doxorubicin via a pH Labile Linker, 152 J Control. Rel. 241 (Year: 2011).*
Derek G. van der Poll, et al, Design, Synthesis, and Biological Evaluation of a Robust, Biodegradable Dendrimer, 21 Bioconjugate Chem. 764 (Year: 2010).*
Maisie J. Joralemon, et al, PEGylated Polymers for Medicine: From Conjugation to Self-Assembled Systems, 46 Chem. Commun. 1377 (Year: 2010).*

(Continued)

*Primary Examiner* — Sean M Basquill
(74) *Attorney, Agent, or Firm* — Lowenstein Sandler LLP

(57) ABSTRACT

Provided herein are sustained release biodegradable intracanalicular insert comprising a hydrogel and cyclosporine, methods of treating or preventing an ocular disease in a subject in need thereof by administering such inserts as well as methods of manufacturing such inserts.

20 Claims, 21 Drawing Sheets

(56) References Cited

U.S. PATENT DOCUMENTS

| | | | |
|---|---|---|---|
| 2006/0095108 A1 | 5/2006 | Chowdhury et al. | |
| 2007/0298075 A1 | 12/2007 | Borgia et al. | |
| 2008/0140192 A1 | 6/2008 | Humayun et al. | |
| 2008/0247984 A1 | 10/2008 | Messersmith et al. | |
| 2012/0059338 A1 | 3/2012 | Beeley et al. | |
| 2014/0128478 A1 | 5/2014 | Asgharian et al. | |
| 2014/0171375 A1* | 6/2014 | Owen | A61K 47/60 514/21.3 |
| 2014/0296257 A1* | 10/2014 | Hersel | A61K 47/60 514/367 |
| 2016/0331738 A1 | 11/2016 | Jarrett et al. | |
| 2018/0085307 A1 | 3/2018 | Sawhney et al. | |

FOREIGN PATENT DOCUMENTS

| | | |
|---|---|---|
| WO | 2009/008946 | 1/2009 |
| WO | 2010/093873 | 8/2010 |
| WO | 2013/039706 | 3/2013 |
| WO | 2013/086015 | 6/2013 |
| WO | 2016/094646 | 6/2016 |
| WO | 2016/183296 | 11/2016 |
| WO | 2017/015591 | 1/2017 |
| WO | 2017/015616 | 1/2017 |
| WO | 2017/091749 | 6/2017 |
| WO | 2018/058048 | 3/2018 |

OTHER PUBLICATIONS

Ocular TTherapeutix™ Reports Second Quarter 2020 Financial Results and Business Update, Newly Published Physician Fee Schedules for 0356T for the Administration of Intracanalicular Inserts to Support Ongoing Dextenza® Launch, Firefox, 9 pgs.

Avery, et al., "Preliminary Findings from a Phase 1 Trial Evaluating the Safety, Tolerability and Biological Activity of OTX-TKI, a Hydrogel-Based, Sustained-Release Intravitreal Axitinib Implant, in Subjects with Neovascular Age-Related Macular Degeneration," Retina Society Annual Scientific Meeting, 2020.

Avery, Robert L., "Safety and Efficacy of OTX-TKI, a Novel Tyrosine Kinase Inhibitor Hydrogel Intravitreal Implant," Annual VIT Buckle Society Meeting, Apr. 2020.

Csaky, et al, "Evaluating Safety, Tolerability and Biological Activity of OTX-TKI, a Hydrogel-Based, Sustained-Relese Intravitreal Axitinib Implant, in Subjects with Neovascular Age-Releated Macular Degeneration Preliminary Findings from a Phase 1 Trial," Euretina Congress 2020.

Mattessich, et al., "Transforming Drug Delivery Leveraging a Novel Technology Platform," Sep. 2020.

Mattessich, et al., "Transforming Drug Delivery Leveraging a Novel Technology Platform," Oct. 10, 2020.

Database Biosis [Online], Biosciences Information Service, Philadelphia, PA, US; Sep. 2016 (Sep. 2016), Smoot Daniel Lee et al: "Sustained Delivery of Cyclosporine from an Intracanalicular Depot in a Canine Model".

International Search Report and Written Opinion of International Application No. PCT/US2020/051724 dated Jan. 10, 2022, 16 pgs.

Van Der Poll, et al., "Design, Synthesis, and Biological Evaluation of a Robust, Biodegradable Dendrimer," 21 Bioconjugate Chem. 764 (Year: 2010).

Joralemon, et al., "PEGylated Polymers for Medicine: From Conjugation to Self-Assembled Systems," 46 Chem. Commun. 1377 (Year: 2010).

Kaminskas, et al., "Characterisation and Tumor Targeting of PEGylated Polylysine Dendrimers Bearing Doxorubicin via a pH labile Linker," 152 J Control. Rel. 241 (Year: 2011).

International Search Report and Written Opinion of International Application No. PCT/US2021/051724 dated Jan. 10, 2022, 16 pgs.

* cited by examiner

FIGURE 1.2A
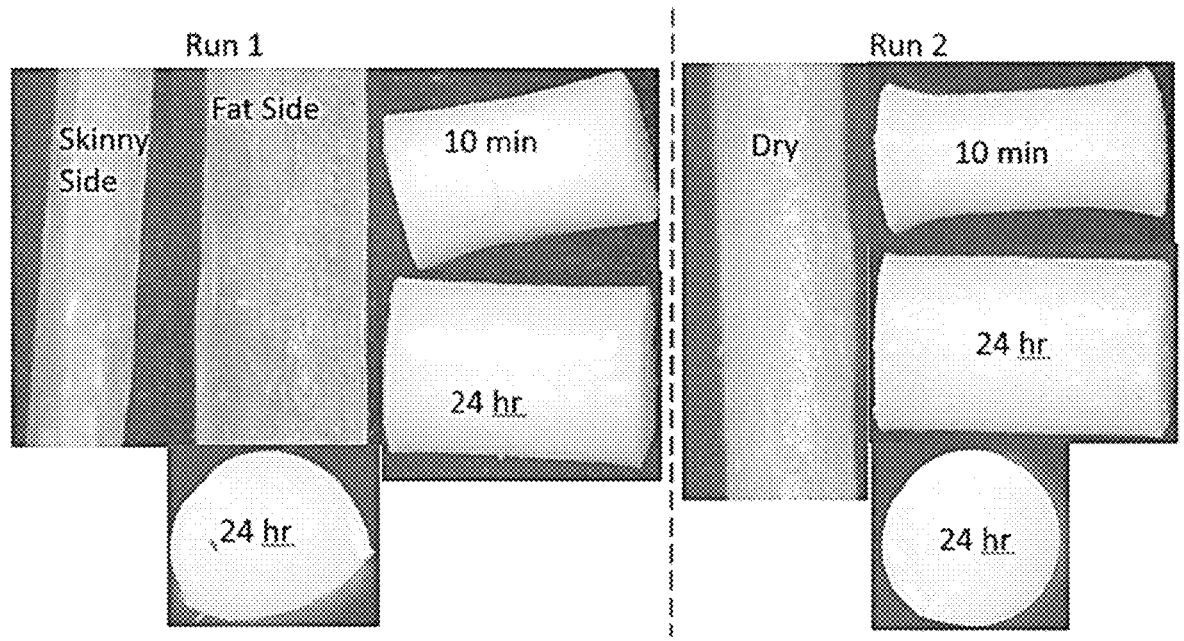
FIGURE 1.2B
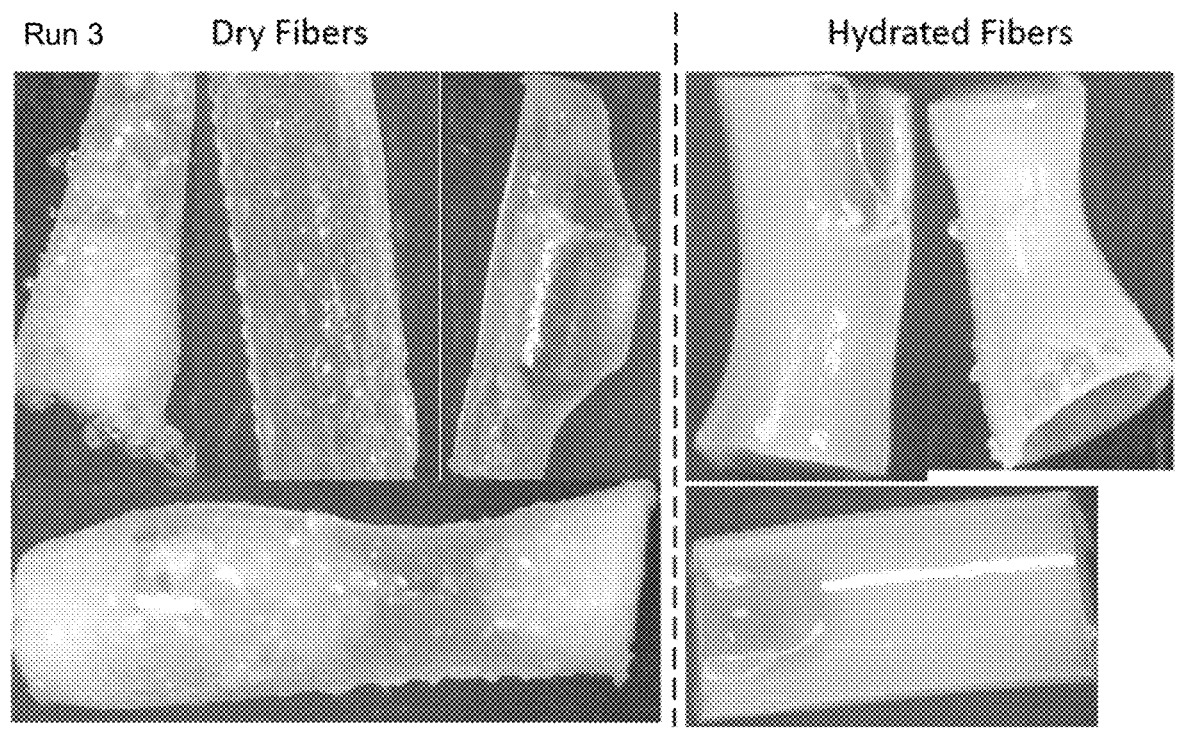

FIGURE 1.2C
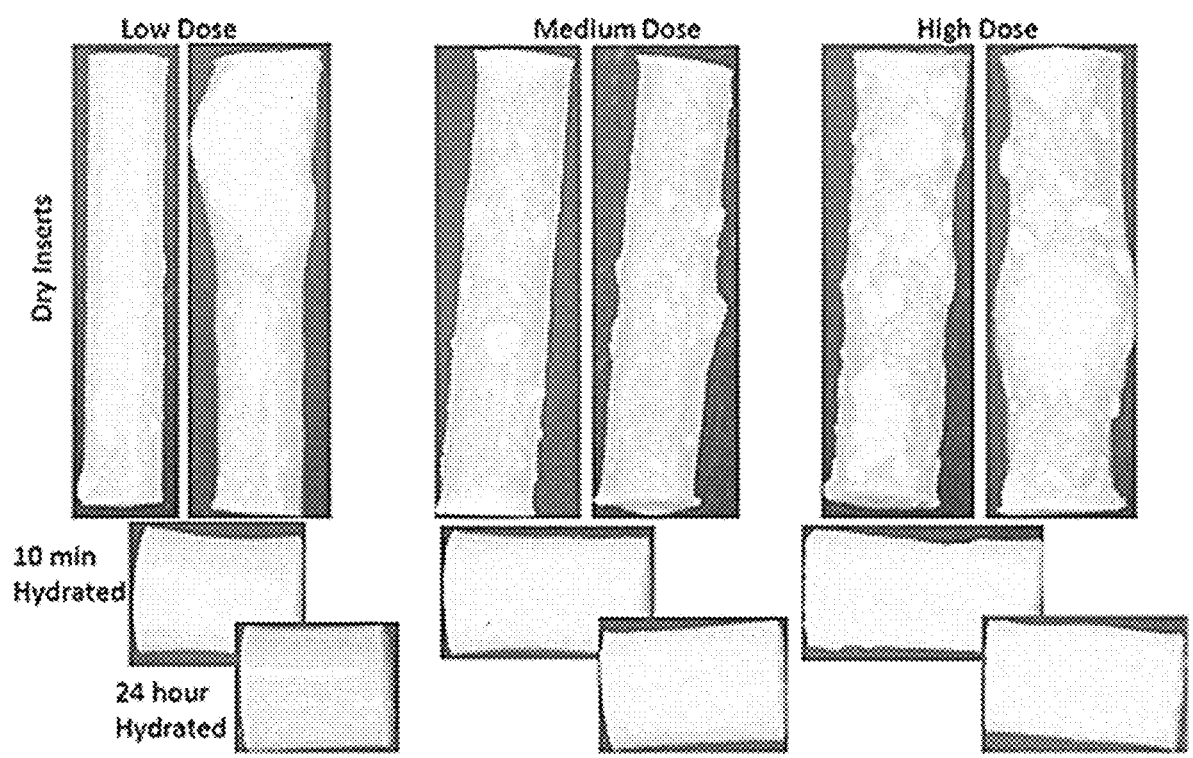

FIGURE 1.3
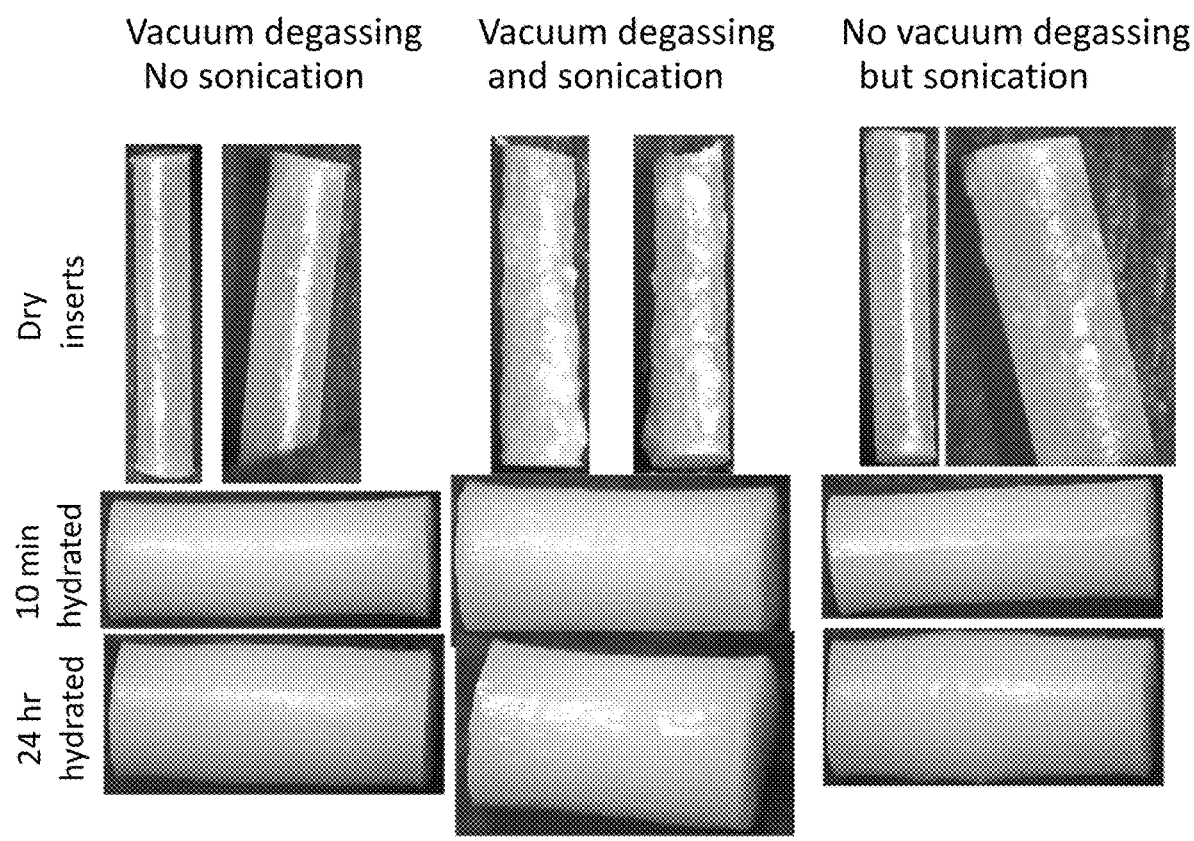

FIGURE 1.4A
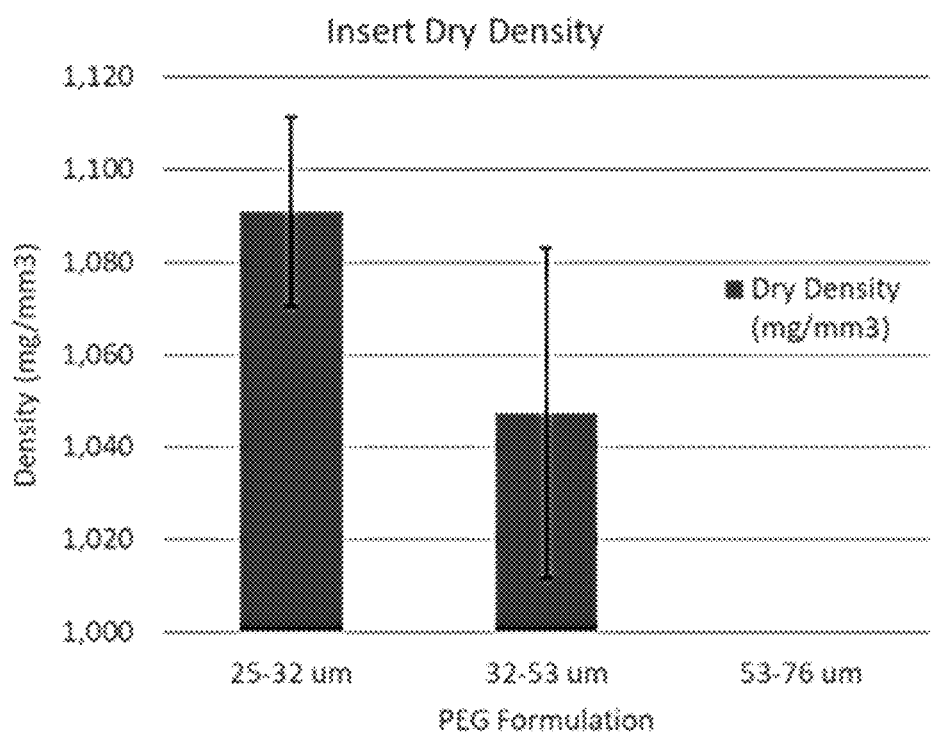
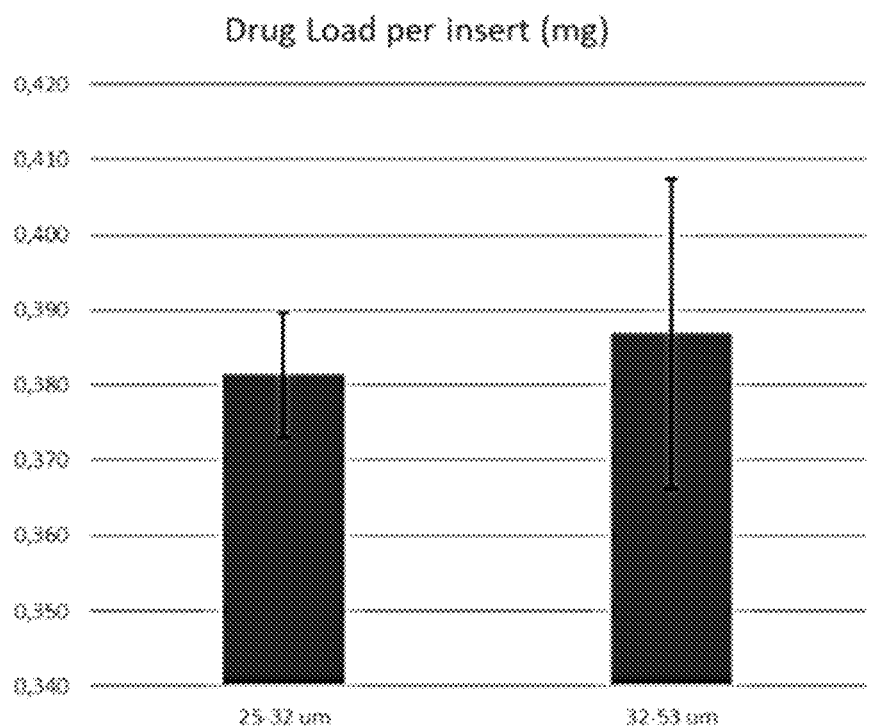

FIGURE 1.4B
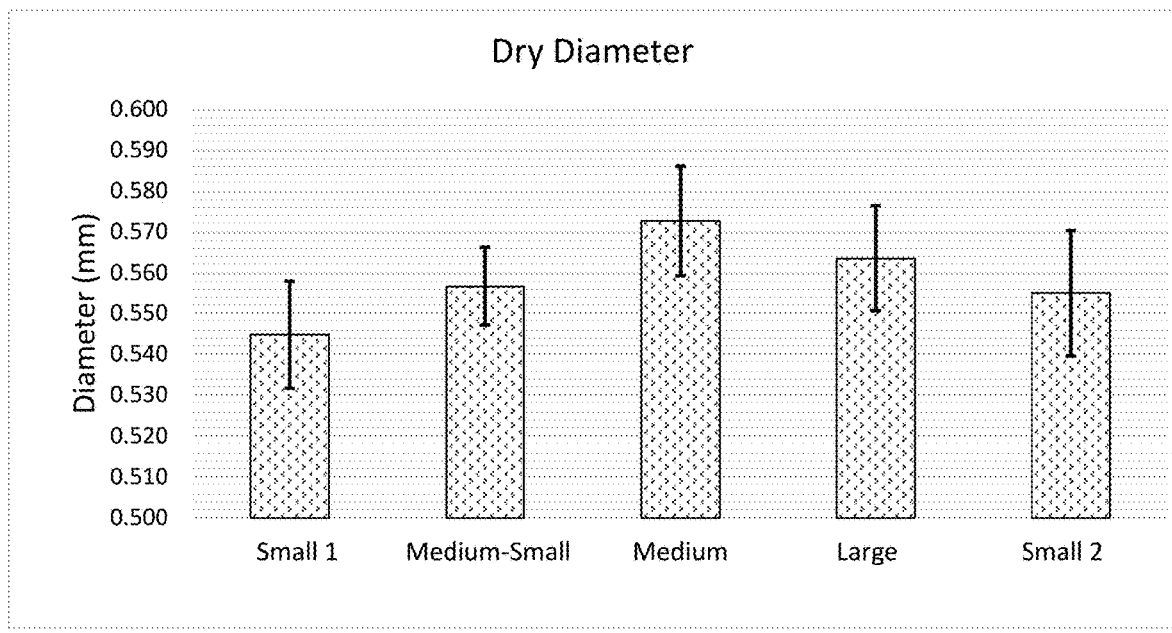

FIGURE 1.4C
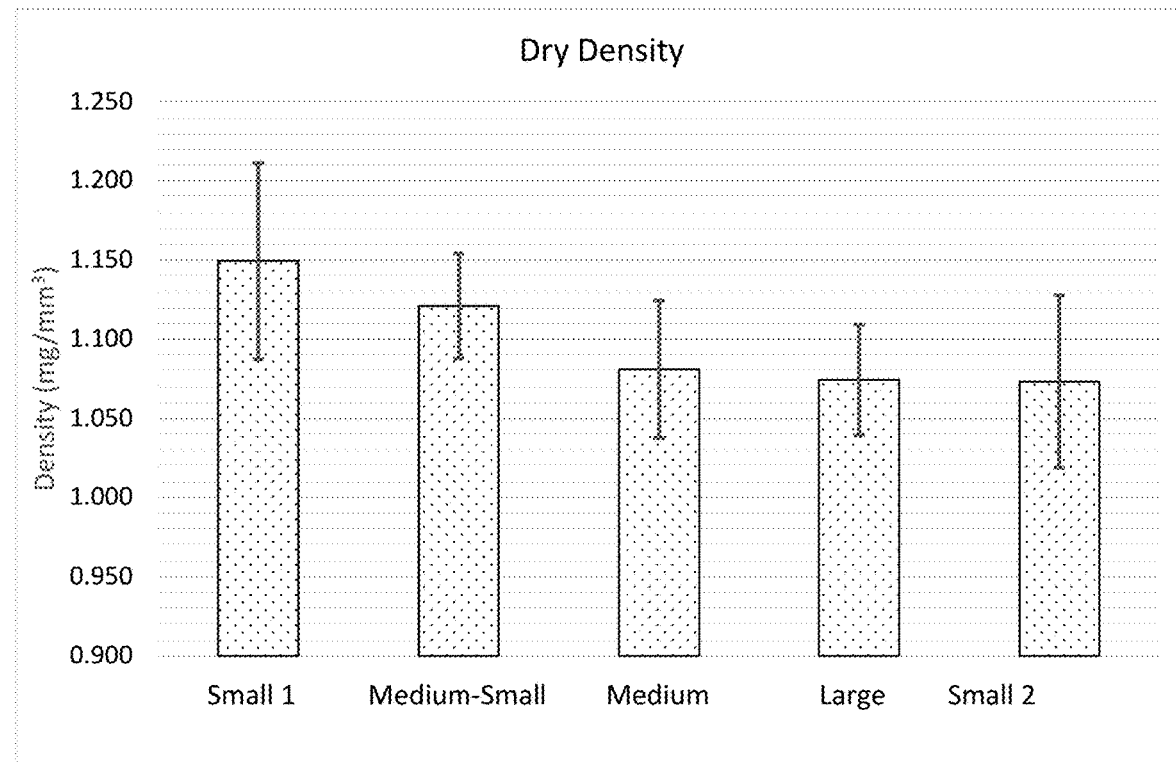
FIGURE 1.4D
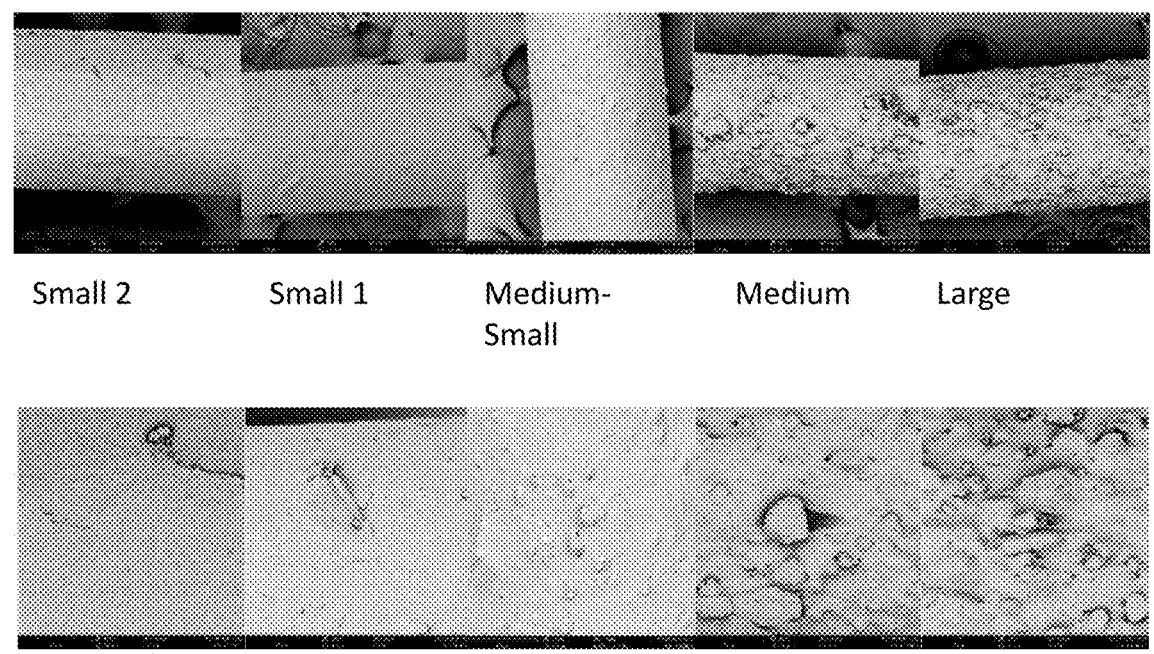

FIGURE 1.4E
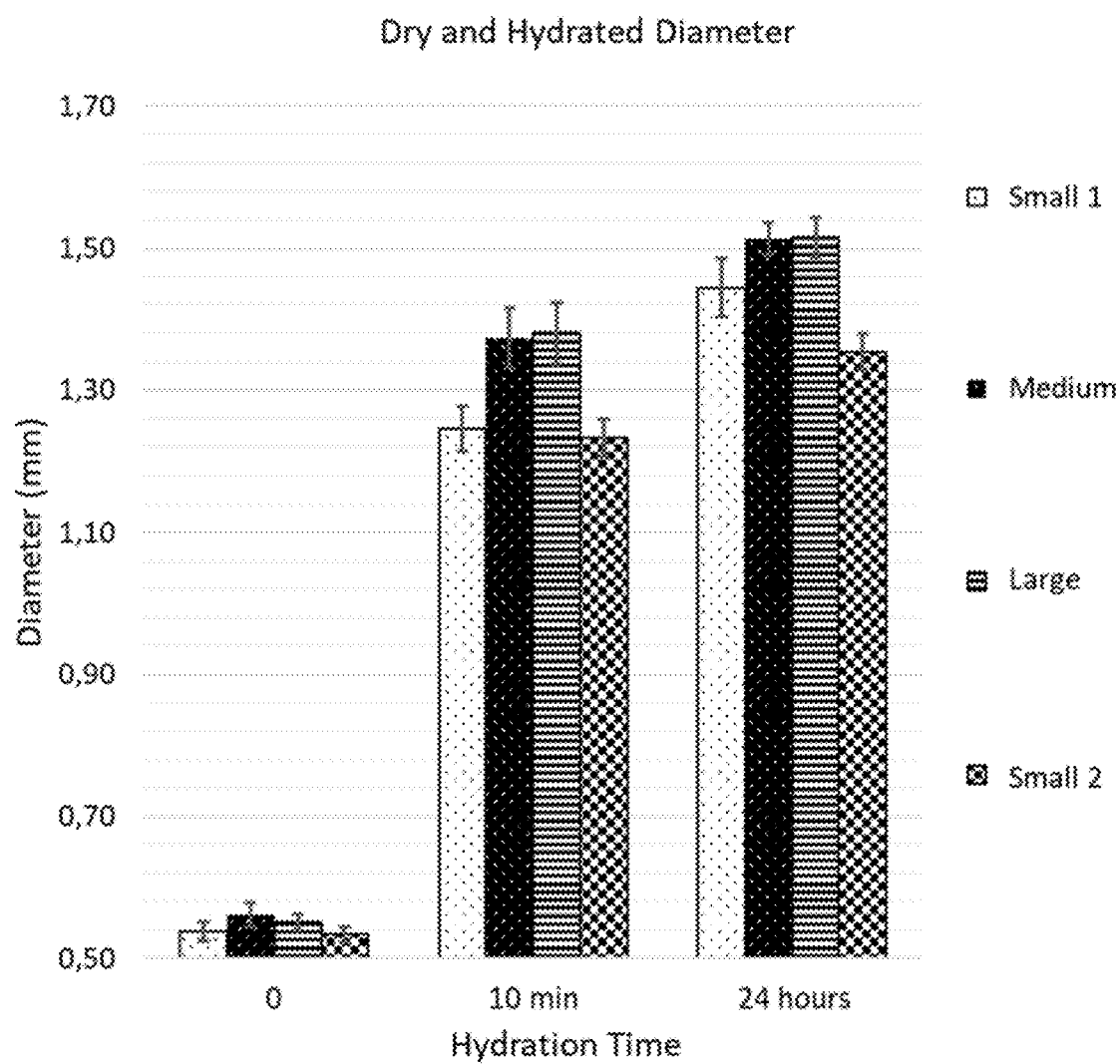

FIGURE 3.1
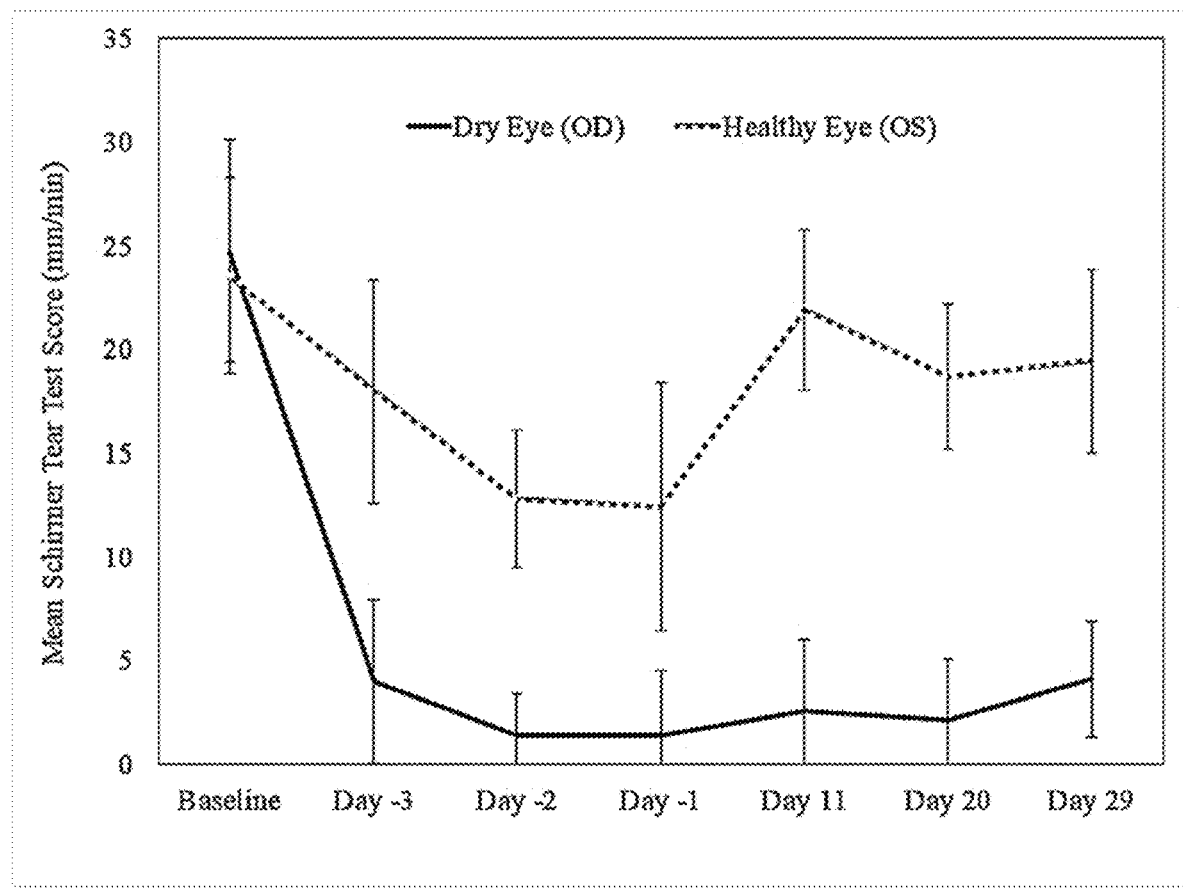

FIGURE 3.2A
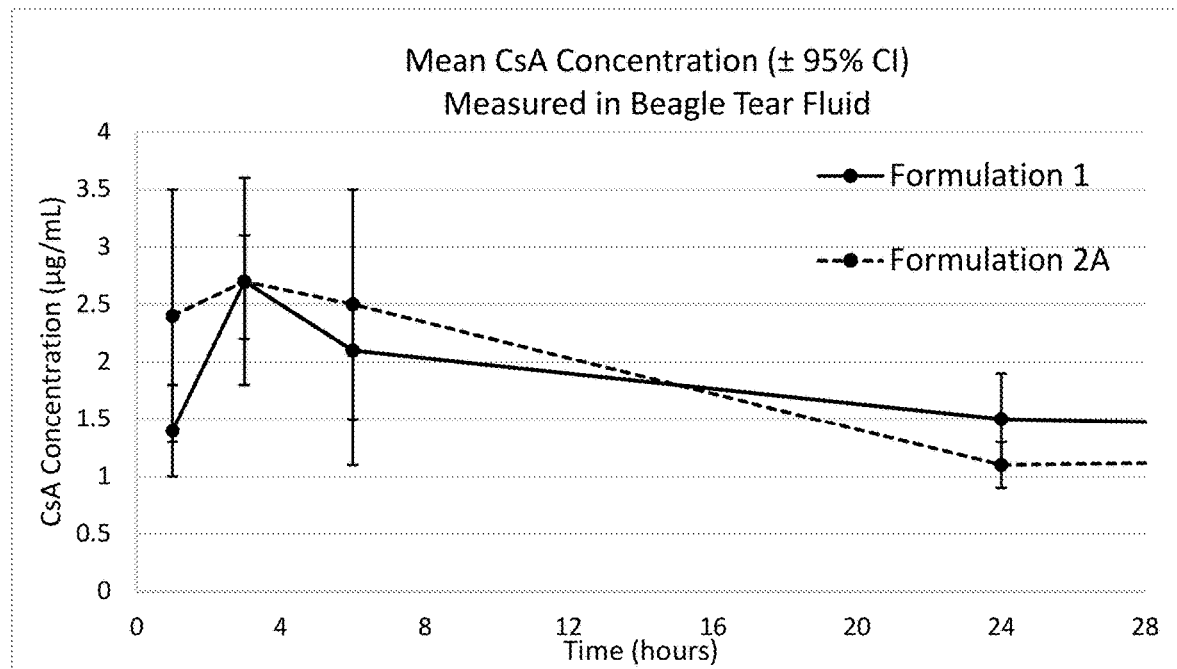
FIGURE 3.2B
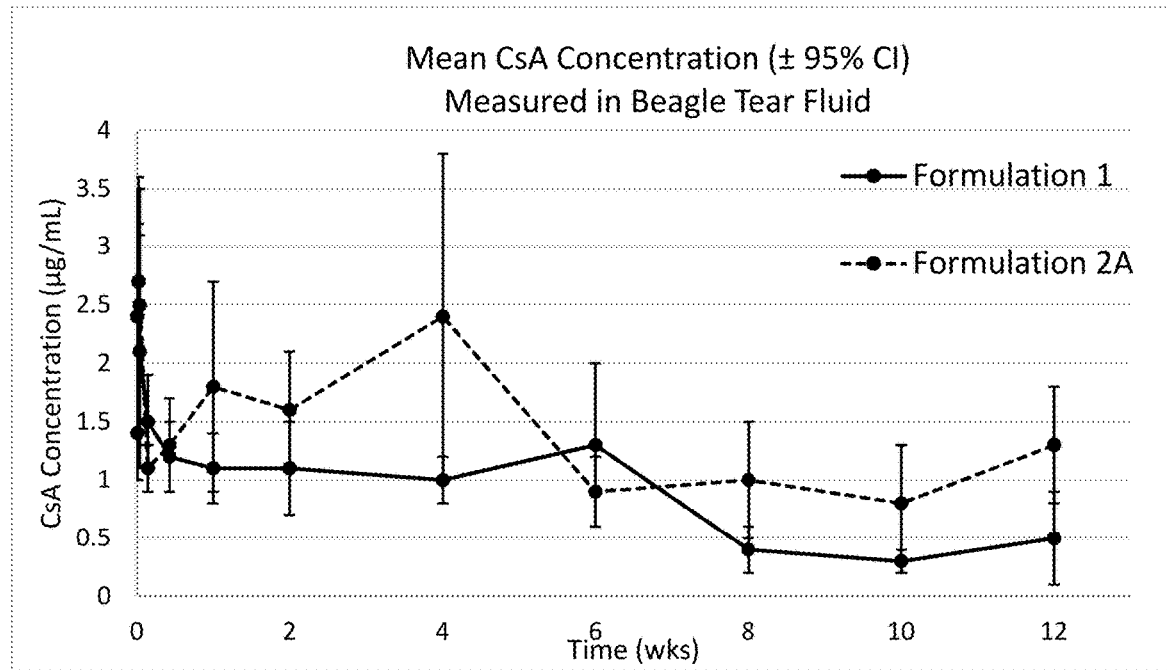

FIGURE 3.3
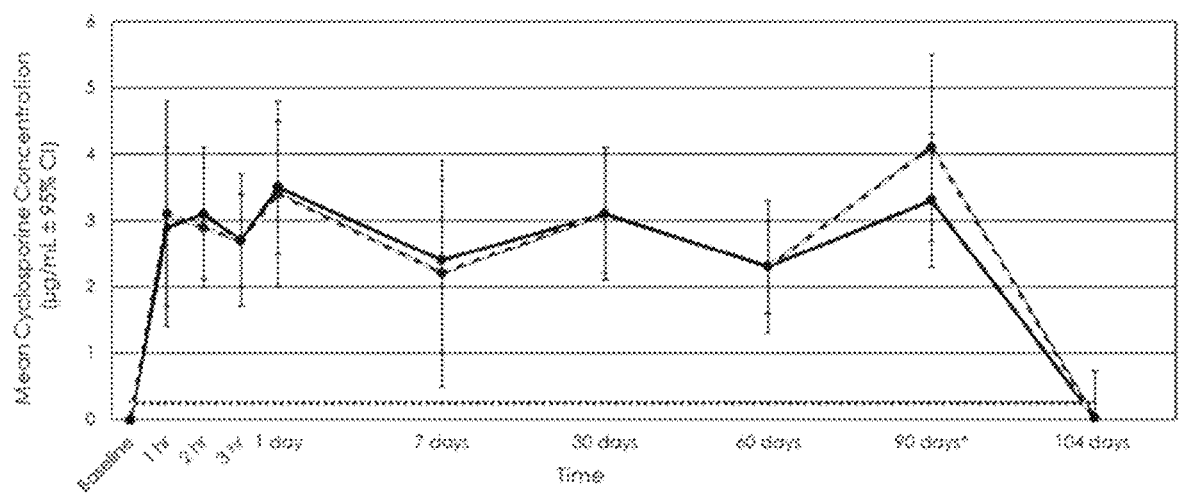

*Subject remains in the study until insert is no longer visible and no evidence of biological activity.

SUSTAINED RELEASE BIODEGRADABLE INTRACANALICULAR INSERTS COMPRISING A HYDROGEL AND CYCLOSPORINE

CROSS-REFERENCE TO RELATED APPLICATION(S)

This application is a continuation of U.S. application Ser. No. 17/483,220, filed on Sep. 23, 2021, which claims the benefit of U.S. Provisional Patent Application No. 63/082,505, filed on Sep. 24, 2020 and U.S. Provisional Patent Application No. 63/124,204, filed on Dec. 11, 2020. The contents of these applications are hereby incorporated by reference in their entirety.

FIELD OF THE INVENTION

Technical Field

The present invention relates to the treatment of ocular diseases, such as diseases affecting the ocular surface such as dry eye or dry eye disease "DED". According to the present invention, ocular diseases are treated by administering e.g., intracanalicularly an insert that is biodegradable and provides sustained release of cyclosporine.

Background

Ocular diseases and disorders, in particular those affecting the ocular surface, are widespread. For example, dry eye disease (DED), also known as Keratoconjunctivitis Sicca (KCS), is one of the most common ophthalmic disorders. Patients who visit ophthalmic clinics frequently report symptoms of dry eye, making it a growing public health problem and one of the most common conditions seen by eye care practitioners. Prevalence increases significantly with age and with female sex. It is estimated that more than 16 million United States (US) adults have been diagnosed with the disorder, with 9 million being classified as moderate to severe.

DED is a multifactorial disorder of the tear film and ocular surface that may result in eye discomfort symptoms such as dryness, burning sensation, itching, redness, stinging, blurred vision, grittiness, pain, foreign body sensation, visual disturbances, tear film instability, ocular fatigue and often ocular surface damage. DED can also make it difficult or impossible for a patient to wear contact lenses, read, work on a computer or drive at night.

Inflammation of both the lacrimal gland and ocular surface has been shown to play a role in dry eye. Factors that adversely affect tear film stability and osmolarity can induce ocular surface damage and initiate an inflammatory cascade that generates innate and adaptive immune responses. These immunoinflammatory responses lead to further ocular surface damage and the development of a self-perpetuating inflammatory cycle. For instance, inflammation of the ocular surface results in a reduction of tear production, which further deteriorates the conditions and potentially leads in turn to inflammation of ocular surface and epithelial cell damage. In animal models, T-cell-mediated inflammation was indeed both a cause and result of dry eye. In humans, dry eye was found to be associated with the presence of conjunctival T-cells and elevated levels of inflammatory cytokines in the tears compared with controls, supportive of inflammation as a driving source of the disorder.

DED can be categorized as acute, episodic or chronic. In some cases, it can be categorized as chronic with acute flares. Chronic DED can require year-round attention. Several pharmacological therapies for DED have been explored and include a stepped approach starting with over the counter lubricants and artificial tear replacements (delivered as drops), progressing to topical anti-inflammatory therapy and lacrimal occlusion using punctal plugs to block tear drainage.

Artificial tears increase the tear volume, but the tear volume may return to its original state due to tear drainage and fluid loss by, e.g., evaporation or absorption through ocular epithelia, and thus require frequent administration. While the residence time could be increased by addition of viscosity enhancers, a high viscosity tear replacement may cause blurred vision. Although punctal plugs have been shown to be effective in patients with DED, plugs can be lost (show poor retention) and may rarely migrate into the nasolacrimal duct, resulting in inflammation or other critical conditions. In some cases, the punctum can be surgically closed with high temperature cautery in an effort to treat DED. Additional approved therapies for DED patients in US are Restasis® (cyclosporine) which increases tear production, Cequa® (cyclosporine) which increases tear production, and Xiidra® (lifitegrast) for signs and symptoms of DED. Recently Eysuvis™ (loteprednol) was approved for acute treatment of DED.

Cyclosporine A is a cyclic polypeptide calcineurin inhibitor immunosuppressant/immunomodulatory agent found in soil fungi, and its immunomodulatory activity is used in the treatment of immune-based disorders, such as transplant rejection, psoriasis, ulcerative colitis, and rheumatoid arthritis. Calcineurin is an enzyme that activates T-cells, which play a key role in cell-mediated immunity. Because calcineurin inhibitors suppress the immune system they are known as immunosuppressants.

The exact mechanism through which cyclosporine acts to ameliorate signs and symptoms of keratoconjunctivitis sicca (KCS) has not been fully established, but it is thought to act as partial immunomodulator. In DED, cyclosporine can inhibit lymphocytic infiltration, decrease the immune inflammatory response and inhibit apoptosis of the lacrimal and conjunctival epithelial cells. Cyclosporine affects immune function by interfering with the activity and growth of T-cells, by entering T-cells and binding cyclophilin. The complex affects T-cell activity by blocking the action of calcineurin and preventing NFATc dephosphorylation and the regulation of the production of pro-inflammatory cytokines such as IL-2, IL-4, interferon-gamma and TNF-alpha.

Topical administration of cyclosporine A has been shown to increase tear fluid secretion, possibly by promoting the local release of parasympathetic nervous system-associated neurotransmitters. A clinical field trial was conducted by veterinary ophthalmologists in 124 dogs afflicted with KCS evaluated efficacy following twice a day treatment with either 2.0 mg/mL cyclosporine (OPTIMMUNE® Ophthalmic Ointment, Intervet Inc.) or vehicle ophthalmic ointment for approximately 90 days, resulting in increased tear fluid production, although some dogs improved clinically without a tear fluid increase.

This is thought to occur through suppression of inflammation by cyclosporine on the ocular surface. Overall improvement was noted in 81% of eyes treated with OPTIMMUNE® Ophthalmic Ointment (vs % treated with vehicle) and withdrawal of therapy resulted in rapid clinical regression in all but one test eye indicating the need for long-term continual therapy. In the management of KCS in dogs, the mechanism by which cyclosporine causes an increase in lacrimation is poorly understood, but clinical improvement is considered to be not necessarily dependent on an increase in tear production. In humans, the beneficial effects of cyclosporine A treatment in DED are better established and findings of several clinical trials indicate that long-term treatment with topical cyclosporine can yield positive results with regard to e.g. corneal surface staining, Schirmer test, blurred vision, frequency of artificial tear application, but also with respect to cellular and molecular markers of disease severity.

Cyclosporine for ophthalmic use was first approved in 1995 for the treatment of KCS in dogs. In 2003, it was approved for ophthalmic use in humans as Restasis® (cyclosporine ophthalmic emulsion 0.5 mg/mL, Allergan) and is indicated for increased tear production in patients whose tear production is presumed to be suppressed due to ocular inflammation associated with KCS. Topical cyclosporine eye drops were shown to decrease inflammatory mediators and increase tear production. Commercial and marketed topical cyclosporine eye drops are sold around the world for the treatment of DED/KCS, Vernal Keratoconjunctivitis (VKC), and ocular inflammation. Cyclosporine ophthalmic solution is currently on the market for topical use for multiple products in multiple jurisdictions as shown below.

| Product Name | Company | Indication | Region | Marketed since |
|---|---|---|---|---|
| Restasis® (0.5 mg/ml) | Allergan | DED (KCS with presumed suppression of tear substitutes) | US, Canada, and 33 other countries | 2003 |
| Ikervis® (1.0 mg/ml) | Santen Pharmaceutical | DED (Severe keratitis which has not improved with tear substitutes) | Europe | 2015 |
| Papilock mini® (1.0 mg/ml) | Santen Pharmaceutical | VKC | Japan | 2005 |
| Modusik-A Ofteno® (1.0 mg/ml) | Laboratorios Sophia | KCS with a functional decrease of lacrimal glands | Mexico, Chile Columbia, Peru, Ecuador, Argentina | 2003 |
| Lacrinmune® (0.5 mg/ml) | Bausch & Lomb, Inc. | KCS with a functional decrease of lacrimal glands | Argentina | NA |
| TJ Cyporin® (0.5 mg/ml) | Taejoon Pharma Co, Ltd | Ocular inflammation associated with KCS | South Korea | 2003 |
| Cyporin® (0.5 mg/ml) | Aristopharma, Ltd | Ocular inflammation associated with KCS | Bangladesh, Myanmar | NA |
| Cyclorin® (0.5 mg/ml) | Ibn Sina Pharmaceutical Industry, Ltd. | Ocular inflammation associated with KCS | Bangladesh | NA |
| Optimmune® (2.0 mg/ml) | Intervet, Inc. (Merck Animal Health) | Chronic KCS and superficial keratitis in dog | WW | 1995 |
| Cequa® (0.9 mg/ml) | Sun Ophthalmics | DED (KCS with presumed suppression of tear production) | US | 2018 |

However, there are limitations with the application of topical drops, which affect patient management. These limitations include difficulty with handling the bottle, limited instillation accuracy, potential washout of drops, and limited bioavailability of topical eye drops (Aldrich et al, 2013, Ophthalmic preparations, USP, 39(5), pp. 1-21). Specific issues with currently available eye drop formulations of cyclosporine are tolerability issues such as burning and stinging, and slow onset of action which can be from many weeks to months. The high frequency of administration (e.g. several times per day) highly affects daily life of patients In humans, the bioavailability from topical eye drops reaching the ocular tissues is less than 5%. Other limitations include a delayed onset of action (many weeks to months), as well as the high drug dose in the drops, which may be the cause for adverse reactions, such as ocular burning associated with topical cyclosporine eye drops (Restasis® NDA #021023).

There is thus an unmet need for a form of cyclosporine A treatment that overcomes the disadvantages of current commercial, topical formulations, in particular for dosage forms that allow a sustained release of cyclosporine A and associated less frequent administration that increases quality of life and patient compliance, has less risk of infections and adverse effects such as burning and stinging in the eyes.

Drug delivery from punctal plugs are beneficial over topical drops in that they allow for a sustained release of the drug over time by forming a depot from which the drug is slowly being released. Administration consists of a one-time administration of the plug, which addresses the above-mentioned limitations inherent to long-term administration of topical eye-drops.

However, intracanalicular plugs are also associated with challenges. The intracanalicular administration route has certain anatomically implied restrictions (it needs to be small enough to enter the lacrimal punctum) and it is difficult to develop an ophthalmic intracanalicular plug that is easy to administer and to remove once the drug depot is depleted if necessary, fits well, i.e. provides appropriate retention so that it is not unintentionally lost, but at the same time does not cause any discomfort or unintended administration site reactions such as inflammation.

In addition, drug release needs to be appropriate and consistent over a sustained period of time. In view of the small size of the plug, it is challenging to formulate to include an adequate drug load and sustained-release properties.

Against this background, it is clear that there is a demand for alternative cyclosporine dosage forms which are effective in the treatment of ocular diseases such as DED.

All references disclosed herein are hereby incorporated by reference in their entireties for all purposes.

OBJECTS AND SUMMARY OF THE INVENTION

It is an object of certain embodiments of the present invention to provide an intracanalicular insert comprising cyclosporine that is effective for treating an ocular disease, and in particular DED, in a patient for an extended period of time.

It is also an object of certain embodiments of the present invention to provide an intracanalicular insert comprising cyclosporine that is effective for treating an ocular disease, and in particular blepharitis, in a patient for an extended period of time.

It is also an object of certain embodiments of the present invention to provide an intracanalicular insert comprising cyclosporine that is effective for treating an ocular disease, and in particular blepharitis, allergic conjunctivitis and in particular atopic keratoconjunctivitis and vernal keratoconjunctivitis, in a patient for an extended period of time.

As outlined above, one of the major drawbacks of current commercial cyclosporine formulations, e.g. topical eye drops, is the necessity of frequent administration. The present invention aims to address this by enabling effective, prolonged therapy by a one-time administration of a single insert releasing the active continuously that lasts an extended period of time such as several weeks.

Thus, another object of certain embodiments of the present invention is to provide an intracanalicular insert comprising cyclosporine that provides for sustained release of cyclosporine to the ocular surface.

In order to ensure effective therapy over the wearing period of the insert, the cyclosporine release should remain at a substantially constant level (e.g., within the therapeutic window) providing therapeutic effect.

Another object of certain embodiments of the present invention thus is to provide an intracanalicular insert comprising cyclosporine that provides for sustained release and in particular a constant release of cyclosporine to the ocular surface.

Another object of certain embodiments of the present invention is also to provide an intracanalicular insert comprising cyclosporine that has a faster onset of action, e.g. within days or even within hours.

In addition, the present invention also aims at respecting and improving patient compliance, which has still room for improvement in the current commercial products.

Therefore, another object of certain embodiments of the present invention is to provide an intracanalicular insert comprising cyclosporine that is well tolerated and does not provide intolerable discomfort during or after insertion to the canaliculus.

It is also another object of certain embodiments of the present invention to provide an intracanalicular insert comprising cyclosporine that is easy to administer, i.e. is easily inserted in the canaliculus.

Another object of certain embodiments of the present invention is to provide an intracanalicular insert comprising cyclosporine that is easy to handle and does not spill like an eye drop, or break easily.

Another object of certain embodiments of the present invention is to provide an intracanalicular insert comprising cyclosporine that is not prone to incorrect administration by the patient and thus avoids over- and under-dosing.

Another object of certain embodiments of the present invention is to provide an intracanalicular insert comprising cyclosporine that fits well in the canaliculus once inserted, and is not easily lost or inadvertently drained through the lacrimal duct.

Another object of certain embodiments of the present invention is to provide an intracanalicular insert comprising cyclosporine that is easy to remove or to replace, or which does not need to be removed.

Another object of certain embodiments of the present invention thus is to provide an intracanalicular insert comprising cyclosporine that has reduced side effects such as ocular burning, stinging or itching when compared to common treatments such as ophthalmic drops.

Another object of certain embodiments of the present invention thus is to provide an intracanalicular insert comprising cyclosporine that has reduced associated risks such as ocular infections or systemic toxicity when compared to common treatments such as ophthalmic drops.

Another object of certain embodiments of the present invention thus is to provide an intracanalicular insert comprising cyclosporine that has no or reduced impairment of quality of life, e.g. through therapy-associated restrictions such as impossibility or limited possibility of wearing contact lenses, or of reading, working on a computer or driving at night.

Another object of certain embodiments of the present invention is to provide an intracanalicular insert comprising cyclosporine that is simple to manufacture.

Another object of certain embodiments of the present invention is to provide an intracanalicular insert comprising cyclosporine that is easily stored and is stable upon storage.

Another object of certain embodiments of the present invention is to provide an intracanalicular insert comprising cyclosporine that increases tear production and provides for an appropriate tear fluid level in a patient for an extended period of time.

Another object of certain embodiments of the present invention is to provide an intracanalicular insert comprising cyclosporine that resolves or reduces symptoms of an ocular surface disease, in particular DED, such as eye dryness, burning sensation, itching, redness, stinging, grittiness, pain, foreign body sensation, visual disturbances, tear film instability, ocular fatigue and ocular surface damage, in a patient for an extended period of time.

Another object of certain embodiments of the present invention is to provide a method of treating or preventing an ocular disease, and in particular DED, in a patient for an extended period of time, which may address one or more of the issues referred to in the objects listed above.

It is also an object of certain embodiments of the present invention to provide a method of treating an ocular disease, and in particular blepharitis, in a patient for an extended period of time, which may address one or more of the issues referred to in the objects listed above.

It is also an object of certain embodiments of the present invention to provide a method of treating an ocular disease, and in particular blepharitis, allergic conjunctivitis and in particular atopic keratoconjunctivitis and vernal keratoconjunctivitis, in a patient for an extended period of time, which may address one or more of the issues referred to in the objects listed above.

Another object of certain embodiments of the present invention is to provide a method of treating or preventing DED comprising inserting into the canaliculus of a patient a biodegradable insert comprising a hydrogel and cyclosporine, wherein the method may address one or more of the issues listed above for the objects directed to providing an intracanalicular insert.

Another object of certain embodiments of the present invention is to provide a method of treating or preventing DED comprising inserting into the canaliculus of a patient a biodegradable insert comprising a hydrogel and cyclosporine, and inserting into the same canaliculus a second biodegradable insert comprising a hydrogel and cyclosporine after an extended period of time such as at least about 2 months, wherein the method may address one or more of the issues listed above for the objects directed to providing an intracanalicular insert.

Another object of certain embodiments of the present invention is to provide a method of treating or preventing an ocular disease, and in particular DED, in a patient for an extended period of time, wherein a therapeutic effect is achieved that is more than a therapeutic effect achieved by a treatment consisting in the combination of a punctal occlusion by a drug-free punctal plug and administration of cyclosporine eye drops.

Another object of certain embodiments of the present invention is to provide a method of manufacturing an intracanalicular insert, which may address one or more of the issues referred to in the objects related to an intracanalicular insert as listed above.

One or more of these objects of the present invention and others are solved by one or more embodiments as disclosed and claimed herein.

The individual aspects of the present invention are disclosed in the specification and claimed in the independent claims, while the dependent claims claim particular embodiments and variations of these aspects of the invention. Details of the various aspects of the present invention are provided in the detailed description below.

BRIEF DESCRIPTION OF THE DRAWINGS

FIG. 1.2A depicts dry and hydrated insert fibers prepared in Example 1.2 (Run 1 and Run 2).

FIG. 1.2B depicts dry and hydrated insert fibers prepared in Example 1.2 (Run 3).

FIG. 1.2C depicts dry and hydrated insert fibers prepared in Example 1.2 (Low, Medium and High Dose). The main portion of the prepared dry insert fibers independent of the dose showed a particulate, cylindrical shape without any visible surface defects (left). In addition, also the inserts with the highest surface deformations per dose are presented (right).

FIG. 1.3 depicts dry and hydrated insert fibers prepared in Example 1.3.

FIGS. 1.4A to 1.4E depicts the insert dry density and the drug load per insert, the dry diameter, the dry density, microscopic images as well as a chart showing the dry and hydrated diameters of the insert fibers prepared in Example 1.4 in dependency of the hydration time, respectively.

FIG. 3.1 depicts the results of tear production as followed over time by a Schirmer's Tear Test of Example 3.4.

FIGS. 3.2A and 3.2B depict the cyclosporine A (CsA) concentration over time measured in beagle tear fluid of Example 3.5.

FIG. 3.3 depicts the cyclosporine A (CsA) concentration over time measured in beagle tear fluid of Example 3.6.

DEFINITIONS

Figure 1:
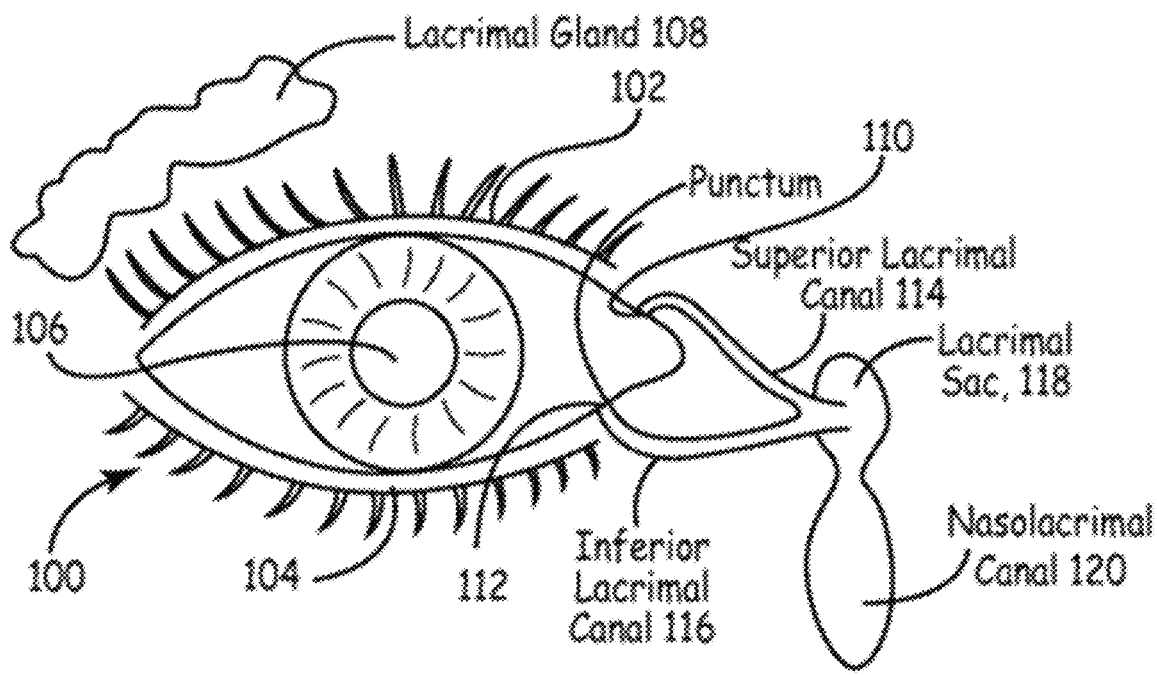
FIG. 1 is a schematic representation of an eye and the lacrimal system.

The term "intracanalicular insert" as used herein refers to an object that contains an active agent, specifically cyclosporine and that is administered, i.e. inserted to the lacrimal canaliculus where it remains for a certain period of time while it releases the active agent into the surrounding environment. An insert can be of any predetermined shape, most of ten rod-like shape before being inserted, which shape may be maintained to a certain degree upon placing the insert into the desired location, although dimensions of the insert (e.g. length and/or diameter) may change after administration due to hydration as further disclosed herein. In other words, what is inserted into the eye is not a solution or suspension, but an already shaped, coherent object. The insert has thus been completely formed, e.g., according to the methods disclosed herein, prior to being administered. An intracanalicular insert can be designed to be biodegradable over the course of time (as disclosed below), and thus may thereby soften, change its shape and/or decrease in size, and in the end might be eliminated either by dissolution or disintegration upon which the remainder of the insert will be drained down the lacrimal duct. In the present invention the term "insert" is used to refer both to an insert in a hydrated (also called "swollen") state when it contains water (e.g. after the insert has been (re-)hydrated once administered to the eye or otherwise immersed into an aqueous environment) and to an insert in its dry (dried/dehydrated) state, e.g., when it has been dried to a low water content of e.g. not more than 1% by weight.

The term "ocular" as used in the present invention refers to the eye in general, or any part or portion of the eye (as an "ocular insert" can in principle be administered to any part or portion of the eye). The present invention in certain embodiments is directed to intracanalicular injection of an ocular insert, and to the treatment of dry eye disease (DED), as further disclosed below.

The term "biodegradable" refers to a material or object (such as the intracanalicular insert according to the present invention) which becomes degraded in vivo, i.e., when placed in the human or animal body. In the context of certain embodiments of the present invention, as disclosed in detail herein below, the insert comprising the hydrogel within which cyclosporine is contained, slowly biodegrades over time once administered into the canaliculus of the eye. In certain embodiments, biodegradation takes place at least in part via ester hydrolysis in the aqueous environment of the canaliculus. The insert slowly softens and disintegrates, resulting in clearance through the nasolacrimal duct.

A "hydrogel" is a three-dimensional network of one or more hydrophilic natural or synthetic polymers (as disclosed herein) that can swell in water and hold an amount of water while maintaining or substantially maintaining its structure, e.g., due to chemical or physical cross-linking of individual polymer chains. Due to their high-water content, hydrogels are soft and flexible, which makes them very similar to natural tissue. In the present invention the term "hydrogel" is used to refer both to a hydrogel in the hydrated state when it contains water (e.g. after the hydrogel has been formed in an aqueous solution, or after the hydrogel has been hydrated or (re-)hydrated once inserted into the eye or otherwise immersed into an aqueous environment) and to a hydrogel in its dry (dried/dehydrated) state, e.g., when it has been dried to a low water content of e.g. not more than 1% by weight. In the present invention, wherein an active principle is contained (e.g. dispersed) in a hydrogel, the hydrogel may also be referred to as a "matrix".

The term "polymer network" describes a structure formed of polymer chains (of the same or different molecular structure and of the same or different molecular weight) that are cross-linked with each other. The types of polymers suitable for the purposes of the present invention are disclosed herein below.

The term "amorphous" refers to a polymer or polymer network, which does not exhibit crystalline structures in X-ray or electron scattering experiments.

The term "semi-crystalline" refers to a polymer or polymer network, which possesses some crystalline character, i.e., exhibits some crystalline properties in X-ray or electron scattering experiments.

The term "precursor" herein refers to those molecules or compounds that are reacted with each other and that are thus connected via crosslinks to form a polymer network and thus a hydrogel matrix. While other materials might be present in the hydrogel, such as active agents or buffers, they are not referred to as "precursors".

The parts of the precursor molecules that are still present in a final polymer network are also called "units" herein. The "units" are thus the building blocks or constituents of a polymer network forming the hydrogel. For example, a polymer network suitable for use in the present invention may contain identical or different polyethylene glycol units as further disclosed herein.

The term "sustained release" for the purposes of the present invention is meant to characterize products which are formulated to make cyclosporine available over an extended period of time, thereby allowing a reduction in dosing frequency compared to an immediate release dosage form, such as a solution of cyclosporine that is topically applied onto the eye (i.e. cyclosporine-comprising eye drops). Other terms that may be used herein interchangeably with "sustained release" are "extended release" or "controlled release". Within the meaning of the invention, the term "sustained release" comprises constant cyclosporine release, tapered cyclosporine release as well as any combination thereof such as a constant cyclosporine followed by a tapered cyclosporine release. Within the meaning of the invention, the term "tapered" or "tapering" refers to a decrease of cyclosporine release over time.

The term "extended period of time" as used herein refers to any period of time that would be considered by those of ordinary skill in the art as being extended with respect to treating a disease, and in particular refers to periods such as at least about 1 week, or at least about 1 month or longer, such as up to about 12 months, or any intermediate periods such as about 1 to about 6 months, about 2 to about 4 months, about 2 to about 3 months or about 3 to about 4 months.

The term "wearing time" as used herein refers to the period of time the intracanalicular insert is present in the canaliculus, i.e. the period from administration of the insert until elimination of the insert from the canaliculus. In certain embodiments, elimination of the insert can be achieved by removal of the insert (which may be intentional or unintentional but would not occur spontaneously without external application of force) or by spontaneous clearance after an extended period of time once the insert is either completely biodegraded, completely disintegrated, or substantially disintegrated so that the remaining part(s) of the insert is/are drained away. In certain embodiments, the wearing time is at least about 1 week, or at least about 1 month or longer, such as up to about 12 months, or any intermediate periods such as about 1 to about 6 months, about 2 to about 4 months, about 2 to about 3 months or about 3 to about 4 months.

The term "visualization agent" as used herein refers to a molecule or composition that is contained within the hydrogel of an insert providing the possibility to easily visualize the insert when inserted into the canaliculus of the eye. The visualization agent may be a fluorophore such as fluorescein, rhodamine, coumarin, and cyanine. In certain embodiments the visualization agent is fluorescein or includes a fluorescein moiety.

As used herein, "ocular surface" includes the conjunctiva and/or the cornea, together with elements such as the lacrimal apparatus, including the lacrimal punctum, as well as the lacrimal canaliculus and associated eyelid structures.

As used herein, the terms "tear fluid" or "tears" refer to the liquid secreted by the lacrimal glands, which lubricates the eyes and thus forms the tear film. Tears are made up of water, electrolytes, proteins, lipids, and mucins.

As used herein, in the context of the present invention, the terms "administration", "insertion", "administering" and "inserting" are used synonymously and refer to the placement of the inserts into the lacrimal canaliculus, and in particular in the vertical part of the canaliculus, e.g. in accordance with the procedure as described in Example 4.11. (Insert placement).

As used herein, the term "bilaterally" or "bilateral" refers—in the context of administration of the inserts of the present invention- to an administration of the inserts into both eyes of a patient. Independent for each eye, the inserts may be inserted into the superior or inferior canaliculus of the eye, or into both superior and inferior canaliculus of the eye.

The term "plug" refers to a device, which is capable of providing an occlusion, substantial occlusion or partial occlusion of the tear ducts ("lacrimal occlusion") thereby preventing or reducing draining of tears, which helps to keep the eyes moist. Plugs can be classified into "punctal plug" and "intracanalicular plugs". Intracanalicular plugs are also referred to as "canalicular plugs" in literature. Both plug classes are inserted through the upper and/or lower punctum of the eye. Punctal plugs rest at the punctal opening making them easily visible and, hence, removable without much difficulty. However, punctal plugs show poor retention rates and can be contaminated with microbes due to their exposed composition, rarely resulting in infection. In contrast, intracanalicular plugs are not visible and provide a better retention rate compared to punctal plugs as they are placed inside either the vertical or the horizontal canaliculus. However, intracanalicular plugs are not easy to remove and provide an increased risk of migration. Commercially available plugs are often made of collagen, acrylic, or silicone.

The terms "canaliculus" (plural "canaliculi") or alternatively "tear duct" as used herein refer to the lacrimal canaliculus, i.e. the small channels in each eyelid that drain tear fluid from the lacrimal punctum to the nasolacrimal duct (see also FIG. 1). Canaliculi therefore form part of the lacrimal apparatus that drains lacrimal fluid from the surface of the eye to the nasal cavity. The canaliculus in the upper eyelid is referred to as "superior canaliculus" or "upper canaliculus", whereas the canaliculus in the lower eyelid is referred to as "inferior canaliculus" or "lower canaliculus". Each canaliculus comprises a vertical region, referred to as "vertical canaliculus" following the lacrimal punctum and a horizontal region, referred to as "horizontal canaliculus" following the vertical canaliculus, wherein the horizontal canaliculus merges into the nasolacrimal duct.

The term "punctum" (plural "puncta") refers to the lacrimal punctum, a minute opening on the margins of the eyelids, representing the entrance to the canaliculus. As tears are produced, some fluid evaporates between blinks, and some is drained through the lacrimal punctum. Both the upper and the lower eyelid show the lacrimal punctum, the puncta therefore referred to as "upper punctum" or "superior punctum" and "lower punctum" or "inferior punctum", respectively (see also FIG. 1).

The term "intracanalicular insert" refers to an insert that can be administered through the upper or lower punctum or through both upper and lower puncta into the superior or inferior canaliculus of the eye or into both the superior and inferior canaliculus of the eye, in particular into the superior or inferior vertical canaliculus of the eye or into the superior and inferior vertical canaliculus of the eye. Due to the intracanalicular localization of the insert, the insert blocks tear drainage by way of lacrimal occlusion as observed for intracanalicular plugs. In certain embodiments, the intracanalicular inserts of the present invention are inserted bilaterally into the inferior vertical canaliculi of the eyes. According to certain embodiments of the invention, the intracanalicular insert is a sustained release biodegradable insert.

The terms "API", "active (pharmaceutical) ingredient", "active (pharmaceutical) agent", "active (pharmaceutical) principle", "(active) therapeutic agent", "active", and "drug" are used interchangeably herein and refer to the substance used in a finished pharmaceutical product (FPP) as well as the substance used in the preparation of such a finished pharmaceutical product, intended to furnish pharmacological activity or to otherwise have direct effect in the diagnosis, cure, mitigation, treatment or prevention of a disease, or to have direct effect in restoring, correcting or modifying physiological functions in a patient.

The API used according to the present invention is cyclosporine A. The term "cyclosporine" as used herein refers to cyclosporine A and in particular does not refer to cyclosporine B, C, D, E, H, and L, which are metabolites of cyclosporine A, and also does not refer to cyclosporine U, G, Dihydrocyclosporine A or Isocyclosporine A, which can be contained as impurities in cyclosporine A. In certain embodiments, cyclosporine A may contain cyclosporine B, C, D, E, G, H, L and U, Dihydrocyclosporine A and Isocyclosporine A as impurities in a concentration of not more than 1.0% each or not more than 0.7% each, may further contain unknown impurities in a concentration of not more than 0.3% each or not more than 0.1% each, and may contain impurities overall in a total amount of not more than 2.5% or not more than 1.5%.

The molecular formula of cyclosporine A is $C_{62}H_{111}N_{11}O_{12}$ and its IUPAC name is 30-ethyl-33-(1-hydroxy-2-methylhex-4-enyl)-1,4,7,10,12,15,19,25,28-nonamethyl-6,9,18,24-tetrakis(2-methylpropyl)-3,21-di(propan-2-yl)-1,4,7,10,13,16,19,22,25,28,31-undecazacyclotritriacontane-2,5,8,11,14,17,20,23,26,29,32-undecone (CAS No. 59865-13-3). Its molecular weight is 1203 Daltons. It has the following chemical structure:

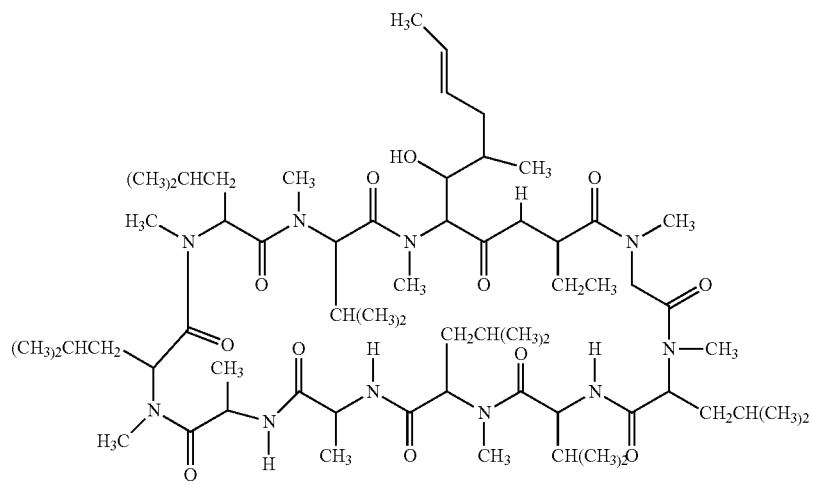

Cyclosporine is a white to practically white powder which is soluble in various organic solvents such as acetone, methanol and ethanol (96% v/v), but practically insoluble in water. In certain embodiments, cyclosporine is micronized.

For the purposes of the present invention, cyclosporine in all its possible forms, including polymorphs or any pharmaceutically acceptable salts, anhydrates, hydrates, other solvates or derivatives, can be used. Whenever in this description or in the claims cyclosporine is referred to without further specification, even if not explicitly stated, it also refers to cyclosporine A (see above) in the form of any such polymorphs, pharmaceutically acceptable salts, anhydrates, solvates (including hydrates) or derivatives of cyclosporine. With respect to cyclosporine, suitable solid forms include without limitation the pure substance form in any physical form known to the person of ordinary skill in the art. For example, cyclosporine may be in the form of particles. Particles can be amorphous or crystalline, or present a mixture of the two forms, and can be made of any size which could be without limitation classified as coarse, fine or ultrafine particles, the dimensions of which may be in particular visible to the naked eye or under the microscope, and have shapes such as single grains and agglomerates. Particles may also be micronized. As used herein, the term "micronized" refers to small-size particles, in particular those of microscopic scale, which are without limitation reduced in particle size, by e.g. jet milling, jaw crushing, hammer milling, wet milling, precipitation in non solvent, cryomilling (milling with liquid nitrogen or dry ice) and ball milling. Cyclosporine can also be present in dissolved or dispersed state, e.g. within a solvent or in an aqueous medium, for example in the form of particles dispersed in an aqueous suspension which may optionally include further excipients such as a surfactant.

As used herein, the term "therapeutically effective" refers to the amount of cyclosporine needed to produce a desired therapeutic result after administration. For example, in the context of the present invention, one desired therapeutic result would be the reduction of symptoms associated with DED, e.g., as measured by in vivo tests known to the person of ordinary skill in the art, such as an increase of a Schirmer's tear test score, a reduction of Staining values as measured by conjunctival lissamine green staining or corneal fluorescein staining, a reduction of the eye dryness severity and/or eye dryness frequency score on a visual analogue scale (VAS), a reduction of the Ocular Surface Disease Index and/or the Standard Patient Evaluation of Eye Dryness score as well as a reduction of the best corrected visual acuity. In one embodiment, "therapeutically effective" refers to an amount of cyclosporine in a sustained release intracanalicular insert capable of achieving a tear fluid concentration of 0.236 µg/mL (which is considered to be required for immunomodulation, Tang-Liu and Acheampong, Clin. Pharmacokinet. 44(3), pp. 247-261) over an extended period of time and in particular over substantially the whole remaining wearing period of the insert once said tear fluid concentration is achieved.

As used herein, the values "d10", "d50", "d90" and "d100" refer to a value characterizing the amount of particles in a particle size distribution meeting a certain particle size. In a given particle size distribution, 10% of the particles present a particle size of d10 or less, 50% of the particles present a particles size of d50 or less, 90% of the particles present a particles size of d90 or less, and substantially all particles present a particles size of d100 or less. The percentages may be given by different parameters known to the person of ordinary skill in the art, e.g. the percentages may be based on volume, weight, or the number of the particles. Thus, d50 may exemplarily be the volume-based, the weight-based or the number-based median particle size. For example, a volume-based d90 of 43 µm means that 90% of the particles by volume have a particle size of 43 µm or less. In certain embodiments, the d10, d50 and d90 are volume-based values. The particle size distribution PSD can be commonly measured by methods as known to the person of ordinary skill in the art, and includes sieving as well as laser diffraction methods. In certain embodiments, the PSD is measured by laser diffraction in accordance with USP <429> Light Diffraction Measurement of Particle Size. In certain embodiments, the PSD is measured by laser diffraction using a Beckman Coulter LS 13 320 based on the optical model "Fraunhofer.rf780z" with an obscuration value ranging from 7 to 9%.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that.

As used herein, the singular forms "a," "an," and "the" include plural references unless the context clearly indicates otherwise.

The term "and/or" as used in a phrase such as "A and/or B" herein is intended to include both "A and B" and "A or B".

Open terms such as "include," "including," "contain," "containing" and the like mean "comprising." These open-ended transitional phrases are used to introduce an open ended list of elements, method steps, or the like that does not exclude additional, unrecited elements or method steps.

DETAILED DESCRIPTION

I. The Intracanalicular Insert

The intracanalicular inserts of the present invention in accordance with certain embodiments are characterized in that they provide sustained release, are biodegradable and comprise a hydrogel and cyclosporine.

As also outlined in the definitions section above, providing sustained release means in the context of the present invention that the inserts are capable of making cyclosporine available over an extended period of time. The inserts are administered into the eye and release the cyclosporine slowly into the tear fluid. As the latter is slowly renewed by production of new tear fluid from the lacrimal glands, replacing already present tear fluid on the ocular surface which is drained through the lacrimal duct, the cyclosporine present in the insert is slowly released into the tear fluid, with each blink of the eye, without the need of the patient taking any action. Thus, the inserts provide an advantageous hands-free alternative to traditional eye drops.

Typically, sustained release is maintained, e.g., over several weeks, so that the current product's dosing frequency of multiple times a day (due to the product being in the form of topical eye drops that are prone to fast wash-out) can be dramatically reduced. This means that a patient can benefit from the therapeutic effect of the insert without the need to remind oneself several times a day to self-administer eye-drops, which in itself is a huge advantage, but in addition reduces the risk of incorrect dosing due to inexact instillation or incorrect handling/administration as well as the risk of infections due to the repeated use of the eye drops bottle.

Further, as again also outlined in the definitions section above, the inventive inserts in certain embodiments are designed to slowly biodegrade over a pre-specified time once administered. This means that the inserts can remain in the canaliculus and do not need to be explanted. Normally there is no need for removing the insert, but the patient can simply leave the insert until it is cleared away. On the other hand, in the unexpected event of e.g. an allergic reaction, wearing discomfort or other adverse events such as irritating sensations etc., the (partially biodegraded) insert can be removed by applying slight pressure to expulse the insert through the punctum to the outside or to move the insert further down canaliculus to be cleared through the nasolacrimal duct. The ability for removal and/or ease of removal is also advantageous in case the cyclosporine in the insert is depleted at the end of the wearing time so that the insert needs to be replaced by a new insert in order to maintain the therapeutic effect.

The intracanalicular inserts of the present invention also comprise a hydrogel. A hydrogel as explained in detail in the definitions section is able to absorb water and to transition from a dried to a hydrated state. In certain embodiments, hydration of the hydrogel results in the insert to change its shape. In particular embodiments, the insert swells in diameter and shrinks in length, so that the thin, rod-shaped insert in its dried state can be easily inserted into the canaliculus, and, once administered and positioned correctly, swells in the canaliculus in diameter so that it firmly fits and reduces the risk of migration or loss of the insert. The hydrated insert is soft and thus comfortable to wear despite being firmly secured in position.

In certain embodiments, the hydrogel comprises a polymer network. Details on the polymer network are provided further below.

The principle of such hydrogel plugs that are high-swelling to be firmly positioned have been disclosed, for instance, in U.S. Pat. No. 8,409,606 (hereby incorporated by reference for all purposes with the instant specification prevailing in case of conflict).

The Active Principle:

Details on cyclosporine, its chemical structure and its properties are provided above in the definitions section. As outlined therein, cyclosporine is practically insoluble in water, and thus, without wishing to be bound by theory, it is hypothesized that upon contact with tear fluid, the low drug solubility at physiological conditions (about 10 µg/mL) in conjunction with the cross-sectional area of the insert in contact with the tear fluid as well as the limited volume of the tear fluid is believed to regulate the rate of drug release.

On the other hand, the form and amount of the cyclosporine embedded in the hydrogel may still affect dissolution of the cyclosporine and reaching of a therapeutically effective rate of release.

One aspect of certain embodiments of the present invention is a sustained release biodegradable intracanalicular insert comprising a hydrogel and cyclosporine, wherein the cyclosporine is in the form of particles and wherein the cyclosporine particles are dispersed within the hydrogel.

In certain embodiments of the invention, the cyclosporine particles are uniformly dispersed within the hydrogel. Dispersed within the hydrogel as used herein refers to the cyclosporine particles to be present in substantially pure substance form embedded within the matrix, although it does not exclude a small amount of cyclosporine being found on the surface of the matrix. In certain embodiments the cyclosporine particles form a separate hydrophobic phase that does not contain further excipients other than the cyclosporine and any impurities that may be present in the active material as employed, and in particular does not refer to any microspheres, microparticles or hydrophobic microdomains entrapping the drug and comprising further materials such as an oil, fat, fatty acid, wax, fluorocarbon or other water immiscible phases that have been suggested earlier. The cyclosporine being present in substantially pure form has the advantage of easy manufacture, as no further treatment of the active material is necessary to prepare e.g. microspheres, microparticles or hydrophobic microdomains.

The cyclosporine in certain embodiments may have a loss on drying of not more than 1.5% w/w determined on 100 mg in a capillary stoppered bottle in vacuum at a pressure not exceeding 5 mm of mercury at 60° C., a heavy metals content of not more than 0.002%, organic impurities as defined in the product specification section of Example 2, and in particular a sum of all impurities as determined by HPLC of not more than 1.5%, a cyclosporine content of not less than 97.0% and not more than 101.5% as determined by HPLC, and residual acetone of not more than 4500 ppm and residual ethyl acetate of not more than 2000 ppm as measured by GC Headspace.

The inventive inserts are, in certain embodiments and as also shown in the examples (see in particular Example 2), stable upon storage, and the cyclosporine content does not change substantially upon long term storage.

Thus, in certain embodiments, the cyclosporine content as measured by HPLC after at least 3 months, after at least 6 months, or after at least 12 months of storage at a temperature of from 2 to 8° C. as well as the initial cyclosporine content as measured by HPLC directly before storage is from about 300 to about 410 µg.

In certain embodiments, the cyclosporine content as measured by HPLC after at least 3 months, after at least 6 months, or after at least 12 months of storage at a temperature of from 2 to 8° C. is within 90 to 110% by weight, or within 95 to 105% by weight, or within 98 to 102% by weight of the initial cyclosporine content as measured by HPLC directly before storage.

In certain embodiments, the amount of impurities as measured by HPLC after at least 3 months, after at least 6 months, or after at least 12 months of storage at a temperature of from 2 to 8° C. is not more than 3.0%.

In certain embodiments of the invention, the cyclosporine is in the form of particles. In certain embodiments the particles are micronized particles. Without wishing to be bound by theory, it is believed that cyclosporine particles, and in particular small cyclosporine particles, in a dispersed state enable dissolution of the active that is fast enough to allow for a fast onset of action.

In certain embodiments of the invention, the cyclosporine particles have a d50 value of less than about 50 µm or a d90 value of less than about 43 µm or a d100 value of less than about 45 µm as measured by laser diffraction. As demonstrated by the Examples (see Example 1.4), large particles are believed to have an impact on the mechanical properties of the intracanalicular inserts. In addition, large particles also tend to block the tubes so that casting the precursor mixture (as outlined further below) gets difficult to impossible.

In certain embodiments of the invention, the cyclosporine particles have a d50 value ranging from about 3 to about 17 µm, or from about 4 to about 12 µm, or from about 5 to about 8 µm. As demonstrated by the Examples (see Example 1.4), the particle size has a substantial impact on the density, swelling behavior as well as surface quality of the inserts, and high densities and smoother insert surfaces, which can be achieved by smaller particles, need to be weighed up against better hydration and swelling behavior of large particles.

In certain embodiments, the d50, d90 and d100 values refer to those of the cyclosporine particles used to manufacture the inserts, or to those of the cyclosporine particles present in the inserts.

In terms of the amount of cyclosporine contained in the insert, a high concentration of active in the insert is desirable in certain embodiments as it will allow a high dose of active (resulting in the sustained release to last longer and/or at a constant rate, as will be further discussed below) at the same insert dimensions, or the same dose but smaller product dimensions, the latter being preferable in terms of ease of administration and wearing comfort. On the other hand, the concentration has a non-negligible impact on the insert quality, as demonstrated in Example 1.1. I.e., too high or too low concentrations tend to result in the manufactured inserts being "strawed", having large dry diameters and hollow holes. In addition, lower drug concentrations appear to result in improved swelling/hydration behavior.

In certain embodiments of the invention, the insert in a dried state contains from about 15% to about 80%, or from about 30% to about 65% by, or from about 45% to about 55% by weight of the cyclosporine based on the total weight of the insert.

One aspect of the present invention is a sustained release biodegradable intracanalicular insert comprising a hydrogel and cyclosporine, wherein the insert in a dried state contains from about 40% to about 80% by weight of the cyclosporine based on the total weight of the insert.

In terms of absolute amount of active, the dose is an important factor for achieving sustained release.

In certain embodiments of the invention, the insert comprises the cyclosporine in an amount ranging from about 100 µg to about 800 µg.

The cyclosporine is contained in the insert of the invention in a range of doses, e.g., from about 100 µg to about 800 µg, from about 100 µg to about 300 µg, from about 300 µg to about 450 µg, or from about 500 µg to about 800 µg. Any amount within these ranges may be used, such as about 250 µg, about 360 µg, about 600 µg, or about 670 µg, all values also including a variance of +25% and −20%, or a variance of +/−15%, or a variance of +/−10%.

The disclosed amounts of cyclosporine, including the mentioned variances, refer to both the final content of the active principle in the insert, as well as to the amount of active principle used as a starting component when manufacturing the insert.

The Polymer Network:

As indicated above, in certain embodiments, the hydrogel comprises a polymer network. The hydrogel may be formed from precursors having functional groups that form crosslinks to create such a polymer network. These crosslinks between polymer strands or arms may be chemical (i.e., may be covalent bonds) and/or physical (such as ionic bonds, hydrophobic association, hydrogen bridges etc.) in nature.

The polymer network may be prepared from precursors, either from one type of precursor or from two or more types of precursors that are allowed to react. Precursors are chosen in consideration of the properties that are desired for the resultant hydrogel. There are various suitable precursors for use in making the hydrogels. Generally, any pharmaceutically acceptable and crosslinkable polymers forming a hydrogel may be used for the purposes of the present invention. The hydrogel and thus the components incorporated into it, including the polymers used for making the polymer network, should be physiologically safe such that they do not elicit e.g. an immune response or other adverse effects. Hydrogels may be formed from natural, synthetic, or biosynthetic polymers.

Natural polymers may include glycosaminoglycans, polysaccharides (e.g. dextran), polyaminoacids and proteins or mixtures or combinations thereof.

Synthetic polymers may generally be any polymers that are synthetically produced from a variety of feedstocks by different types of polymerization, including free radical polymerization, anionic or cationic polymerization, chain-growth or addition polymerization, condensation polymerization, ring-opening polymerization etc. The polymerization may be initiated by certain initiators, by light and/or heat, and may be mediated by catalysts.

Generally, for the purposes of the present invention one or more synthetic polymers of the group comprising one or more units of polyethylene glycol (PEG), polyethylene oxide, polypropylene oxide, polyvinyl alcohol, poly (vinylpyrrolidinone), polylactic acid, polylactic-co-glycolic acid, random or block copolymers or combinations/mixtures of any of these can be used, while this list is not intended to be limiting.

To form covalently crosslinked polymer networks, the precursors may be covalently crosslinked with each other. In certain embodiments, precursors with at least two reactive centers (for example, in free radical polymerization) can serve as crosslinkers since each reactive group can participate in the formation of a different growing polymer chain.

The precursors may have biologically inert and hydrophilic portions, e.g., a core. In the case of a branched polymer, a core refers to a contiguous portion of a molecule joined to arms that extend from the core, where the arms carry a functional group, which is of ten at the terminus of the arm or branch. Multi-armed PEG precursors are examples of such precursors and are further disclosed herein below.

Thus a hydrogel for use in the present invention can be made e.g. from one multi-armed precursor with a first (set of) functional group(s) and another multi-armed precursor having a second (set of) functional group(s). By way of example, a multi-armed precursor may have hydrophilic arms, e.g., polyethylene glycol units, terminated with primary amines (nucleophile), or may have activated ester end groups (electrophile). The polymer network according to the present invention may contain identical or different polymer units crosslinked with each other. The precursors may be high-molecular weight components (such as polymers having functional groups) or low-molecular weight components (such as low-molecular amines, thiols, esters etc.).

Certain functional groups can be made more reactive by using an activating group. Such activating groups include (but are not limited to) carbonyldiimidazole, sulfonyl chloride, aryl halides, sulfosuccinimidyl esters, N-hydroxysuccinimidyl (NHS) ester, succinimidyl ester, epoxide, aldehyde, maleimides, imidoesters, acrylates and the like. The NHS esters are useful groups for crosslinking of nucleophilic polymers, e.g., primary amine-terminated or thiol-terminated polyethylene glycols. An NHS-amine crosslinking reaction may be carried out in aqueous solution and in the presence of buffers, e.g., phosphate buffer (pH 5.0-7.5), triethanolamine buffer (pH 7.5-9.0), borate buffer (pH 9.0-12), or sodium bicarbonate buffer (pH 9.0-10.0).

In certain embodiments, each precursor may comprise only nucleophilic or only electrophilic functional groups, so long as both nucleophilic and electrophilic precursors are used in the crosslinking reaction. Thus, for example, if a crosslinker has only nucleophilic functional groups such as amines, the precursor polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly (allyl amine), or amine-terminated di-or multifunctional poly(ethylene glycol) can be also used to prepare the polymer network of the present invention.

In one embodiment of the present invention a precursor for the polymer network forming the hydrogel in which the cyclosporine is dispersed to form the insert according to the present invention has about 2 to about 16 nucleophilic functional groups each (termed functionality), and in another embodiment a precursor has about 2 to about 16 electrophilic functional groups each (termed functionality). Reactive precursors having a number of reactive (nucleophilic or electrophilic) groups as a multiple of 4, thus for example 4, 8 and 16 reactive groups, are particularly suitable for the present invention. Any number of functional groups, such as including any of 2, 3, 4, 5, 6, 7, 8, 9, 10, 11, 12, 13, 14, 15, or 16 groups, is possible for precursors to be used in accordance with the present invention, while ensuring that the functionality is sufficient to form an adequately cross-linked network.

PEG Hydrogels:

In a certain embodiment of the present invention, the polymer network forming the hydrogel contains polyethylene glycol (PEG) units. PEGs are known in the art to form hydrogels when crosslinked, and these PEG hydrogels are suitable for pharmaceutical applications e.g. as matrix for drugs intended to be administered to all parts of the human or animal body.

The polymer network of the hydrogel inserts of the present invention may comprise one or more multi-arm PEG units having from 2 to 10 arms, or 4 to 8 arms, or 4, 5, 6, 7 or 8 arms. In certain embodiments, the PEG units used in the hydrogel of the present invention have 4 and/or 8 arms. In certain particular embodiments, a 4-armed PEG is utilized.

The number of arms of the PEG used contributes to controlling the flexibility or softness of the resulting hydrogel. For example, hydrogels formed by crosslinking 4-arm PEGs are generally softer and more flexible than those formed from 8-arm PEGs of the same molecular weight. In particular, if stretching the hydrogel prior to (or also after) drying as disclosed herein below in the section relating to the manufacture of the insert is desired, a more flexible PEG unit may be used, such as a 4-arm PEG, optionally in combination with another multi-arm PEG, such as an 8-arm PEG as disclosed above, or another (different) 4-arm PEG.

In certain embodiments of the present invention, polyethylene glycol units used as precursors have an average molecular weight in the range from about 2,000 to about 100,000 Daltons, or in a range from about 10,000 to about 60,000 Daltons. In certain particular embodiments the polyethylene glycol units have an average molecular weight in a range from about 10,000 to about 40,000 Daltons. In specific embodiments, the polyethylene glycol units used for making the hydrogels according to the present invention have a molecular weight of about 20,000 Daltons.

The molecular weight of polyethylene glycol and polyethylene glycol derivatives can be determined by several methods, including gel electrophoresis such as SDS-PAGE (sodium dodecyl sulphate-polyacrylamide gel electrophoresis), gel permeation chromatography (GPC), GPC with dynamic light scattering (DLS) as well as Matrix-assisted laser desorption/ionization-time of flight (MALDI-TOF) spectrometry. The molecular weight of polyethylene glycol precursors as disclosed herein can be determined by any method known to the person of ordinary skill in the art, including SDS-PAGE, GPC and MALDI-TOF, and in particular is determined by GPC using a PEG standard of known molecular weight (determined e.g. by MALDI-TOF) and polydispersity (determined e.g. by GPC). In case a high accuracy is needed, MALDI-TOF can be used.

The molecular weight of the polyethylene glycol refers to an average molecular weight, which may be selected from various average values known to the person of ordinary skill in the art, including number average molecular weight (Mn), weight average molecular weight (Mw), and peak average molecular weight. Any of such average values, and in particular the three aforementioned average molecular weights can be used in the context of the present invention. In certain embodiments, the average molecular weight of the polyethylene glycol units and precursors as disclosed herein is given as number average molecular weight.

Multi-arm PEG units with a specified molecular weight as used herein may be abbreviated in the form of e.g. 4a20 kPEG, referring to a 4-arm PEG unit with a molecular weight of 20,000.

In a 4-arm PEG, each of the arms may have an average arm length (or molecular weight) of the total molecular weight of the PEG divided by 4. A 4a20 kPEG precursor, which is a particularly suitably precursor for use in the present invention thus has 4 arms with an average molecular weight of about 5,000 Daltons each. An 8a20 k PEG precursor, which could also be used in combination with or alternatively to the 4a20 kPEG precursor in the present invention, thus has 8 arms each having an average molecular weight of 2,500 Daltons. Longer arms may provide increased flexibility as compared to shorter arms. PEGs with longer arms may swell more as compared to PEGs with shorter arms. A PEG with a lower number of arms also may swell more and may be more flexible than a PEG with a higher number of arms. In certain particular embodiments, only a 4-arm PEG precursor is utilized in the present invention. In certain particular embodiments, two different 4-arm PEG precursors are utilized in the present invention. In certain other embodiments, a combination of a 4-arm PEG precursor and an 8-arm precursor is utilized in the present invention. In addition, longer PEG arms have higher melting temperatures when dry, which may provide more dimensional stability during storage.

In certain embodiments, electrophilic end groups for use with PEG precursors for preparing the hydrogels of the present invention are N-hydroxysuccinimidyl (NHS) esters, including but not limited to NHS dicarboxylic acid esters such as the succinimidylmalonate group, succinimidylmaleate group, succinimidylfumarate group, "SAZ" referring to a succinimidylazelate end group, "SAP" referring to a succinimidyladipate end group, "SG" referring to a succinimidylglutarate end group, and "SS" referring to a succinimidylsuccinate end group.

Thus, in certain embodiments, the PEG-precursor is an NHS dicarboxylic acid ester-terminated multi-arm PEG precursor that can be represented by the formula:

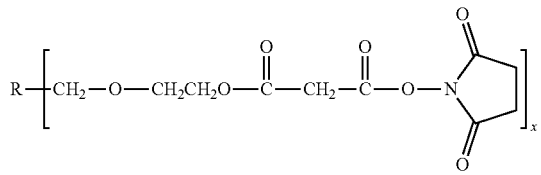

wherein n is determined by the molecular weight of the respective PEG-arm, m is an integer from 0 to 10, and specifically is 1, 2, 3, 4, 5, 6, 7, 8, 9, or 10, and x is the number of arms (and thus can be, e.g., 2, 4, 8, etc., see above). Where m is 1, each arm is terminated with a succinimidylsuccinate (SS) end group, where m is 2, each arm is terminated with a succinimidylglutarate (SG) group, where m is 3, each arm is terminated with a succinimidyladipate (SAP) group, and where m is 6, each arm is terminated with a succinimidylazelate (SAZ) group. With these specific electrophilic end groups, multi-arm PEG units may be abbreviated in the form of e.g. 4a20 kPEG-SAP, referring to a 4-arm PEG with a succinimidyadipate end group and a molecular weight of 20,000 (4 arms, about 5,000 Daltons each). In the above formula, R is a core structure appropriate to provide the desired number of arms. For 4-arm PEG units and precursors, R can be a pentaerythritol structure, whereas for 8-arm PEG units and precursors, R can be a hexaglycerol structure.

In certain embodiments, the PEG precursor is 4a20 kPEG-SG or 4a20 kPEG-SAP.

In certain embodiments, nucleophilic end groups for use with electrophilic group-containing PEG precursors for preparing the hydrogels of the present invention are amine (denoted as "NH$_2$") end groups. Thiol (—SH) end groups or other nucleophilic end groups are also possible.

In certain embodiments, 4-arm PEGs with an average molecular weight of about 20,000 Daltons and electrophilic end groups as disclosed above (such as the SAZ, SAP, SG and SS end groups) are crosslinked for forming the polymer network and thus the hydrogel according to the present invention.

Reactions of e.g. nucleophilic group-containing crosslinkers and electrophilic group-containing PEG units, such as a reaction of amine group-containing crosslinkers with activated ester-group containing PEG units, result in a plurality of PEG units being crosslinked by the crosslinker via an amide group.

In the case of PEGs with NHS-ester end groups such as succinimidylazelate (SAZ)-, succinimidyladipate (SAP)- or succinimidylgluatarate-(SG)-terminated PEG units (see above), the reaction with amine group-containing crosslinkers result in a plurality of PEG units being crosslinked by the crosslinker via a hydrolyzable linker having the formula:

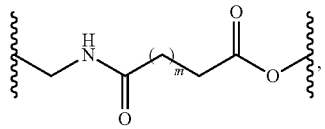

wherein m is an integer from 0 to 10, and specifically is 1, 2, 3, 4, 5, 6, 7, 8, 9, or 10. For a SAZ-end group, m would be 6. For a SAP-end group, m would be 3, for a SG-end group, m would be 2 and for an SS-end group, m would be 1.

In particular embodiments, the SG or the SAP end group is utilized in the present invention. The SG end group may provide for a shorter time until the hydrogel is biodegraded when compared to the use of the other succinimidyl end groups (except the SS group), such as the SAZ end group, which provides for a higher number of carbon atoms in the linker and may thus be more hydrophobic and therefore less prone to ester hydrolysis than the SG end group.

In certain embodiments, an electrophilic group-containing multi-arm polymer precursor, and in particular a multi-arm PEG precursor having an SG or an SAP end group (as defined above) is crosslinked with a nucleophilic group-containing crosslinking agent. The nucleophilic group can be an amine and in particular a primary amine.

In certain embodiments, the nucleophilic group-containing crosslinking agent is a nucleophilic group-containing multi-arm polymer precursor.

In certain other embodiments, the crosslinking agent used is a low-molecular weight component containing nucleophilic end groups, such as amine or thiol end groups. In certain embodiments, the nucleophilic group-containing crosslinking agent is a small molecule amine with a molecular weight below 1,000 Da, comprising two or more primary aliphatic amine groups. A particular crosslinking agent for use in the present invention is, e.g., dilysine, trilysine, tetralysine, ethylenediamine, 1,3-diaminopropane, 1,3-diaminopropane, diethylenetriamine, trimethylhexamethylenediamine, their pharmaceutically acceptable salts, hydrates, but also derivatives such as conjugates (as long as sufficient nucleophilic groups for crosslinking remain present), and any mixtures thereof. In certain preferred embodiments, trilysine is used as crosslinking agent. It is understood that trilysine as used herein refers to trilysine in any form including a trilysine salt, such as trilysine acetate or a trilysine derivative such as a labeled trilysine.

In certain embodiments, the nucleophilic group-containing crosslinking agent is a labeled crosslinking agent and in particular is a labeled trilysine. The crosslinking agent can be labeled with a visualization agent to aid the physician in confirming the presence of the insert e.g. in the course of control examinations. Fluorophores such as fluorescein, rhodamine, coumarin, and cyanine can be used as visualization agent for labeling the crosslinking agent. Labeling can be achieved e.g. by chemical conjugation, and in particular by using the nucleophilic groups of the crosslinking agent for conjugation with the label. Since a sufficient amount of the nucleophilic groups (at least more than one molar equivalent) are necessary for crosslinking, "conjugated" or "conjugation" in general includes partial conjugation, meaning that only a part of the nucleophilic groups are used for conjugation with the label. Thus, in certain embodiments, the crosslinking agent is trilysine labeled by partial conjugation with a visualization agent, wherein in particular about 1% to about 20%, or about 5% to about 10%, or about 8% of the trilysine amine groups are conjugated with a visualization agent.

In certain embodiments, the nucleophilic group-containing crosslinking agent is fluorescein-conjugated trilysine. The fluorescein-conjugated trilysine can be obtained by reacting trilysine acetate with N-hydroxysuccinimide (NHS)-fluorescein.

In certain embodiments, the multi-arm polymer units comprise 4a20 kPEG units and the cross-linking units comprise fluorescein-conjugated trilysine amide units.

In certain embodiments, the polymer network is obtained by reacting 4a20 kPEG-SG with fluorescein-conjugated trilysine in a molar ratio ranging from about 1:2 to about 2:1. In certain other embodiments, the polymer network is obtained by reacting 4a20 kPEG-SS or 4a20 kPEG-SAZ with fluorescein-conjugated trilysine in a molar ratio ranging from about 1:2 to about 2:1.

In certain embodiments, the molar ratio of the nucleophilic and the electrophilic end groups reacting with each other is about 1:1, i.e., one amine group is provided per one electrophilic group such as the SG or the SAP end group. In the case of 4a20 kPEG-SG or 4a20 kPEG-SAP as electrophilic group-containing polymer unit and fluorescein-conjugated trilysine, this results in a molar ratio of the two components of about 1:1, assuming a partial conjugation of the trilysine utilizing one of the four primary amines on average, as the trilysine then has three primary amine groups that may react with the electrophilic SG or SAP ester group. However, an excess of either the electrophilic (e.g. the NHS end groups, such as the SG) end group precursor or of the nucleophilic (e.g. the amine) end group precursor may be used.

Thus, in certain embodiments, the polymer network is obtained by reacting 4a20 kPEG-SG with fluorescein-conjugated trilysine in a molar ratio ranging from about 1:2 to about 2:1, and in particular in molar ratio of about 1:1.

In certain embodiments, the polymer network is obtained by reacting 4a20 kPEG-SAP with fluorescein-conjugated trilysine in a molar ratio ranging from about 1:2 to about 2:1, and in particular in molar ratio of about 1:1.

Surfactant:

One aspect of the present invention is a sustained release biodegradable intracanalicular insert comprising a hydrogel and cyclosporine, wherein the insert contains a surfactant.

As outlined further above, cyclosporine is a hydrophobic active that is practically non-miscible with the hydrophilic hydrogel material, and in certain embodiments, is present in the form of dispersed particles with a specific particle size. It has been shown that a certain particle size is advantageous in terms of the insert properties. However, small particles are also prone to agglomeration. Without wishing to be bound by theory, the presence of a surfactant is believed to prevent agglomeration and to improve content uniformity of the hydrogel.

In addition, experimental results indicate that the presence of a surfactant aids in preventing undesirable tube adhesion of the casted hydrogel during manufacture of the inserts (see Example 1.2) and improves the insert quality.

Thus, in certain embodiments, the insert contains a surfactant.

In certain embodiments, the insert in a dried state contains from about 0.01% to about 5% by weight or from about 0.01% to about 2% by weight or from about 0.2% to about 2% by weight or from about 0.05% to about 0.5% by weight of a surfactant based on the total weight of the insert.

As shown in Example 1.2, the surfactant type may be important in view of the ability to prevent cyclosporine particle aggregation. In certain embodiments, the insert contains a non-ionic surfactant. The non-ionic surfactant may comprise a poly(ethylene glycol) chain. Exemplary non-ionic surfactants which can be used herein are poly (ethylene glycol) sorbitan monolaurate commercially available as Tween® (and in particular Tween®20, a PEG-20-sorbitan monolaurate, or Tween®80, a PEG-80-sorbitan monolaurate), poly(ethylene glycol) ester of castor oil commercially available as Cremophor (and in particular Cremophor40, which is PEG-40-castor oil), and an ethoxylated 4-tert-octylphenol/formaldehyde condensation polymer which is commercially available as Tyloxapol.

Additional Ingredients:

The insert of the present invention may contain, in addition to the polymer units forming the polymer network as disclosed above, the active principle and the surfactant, other additional ingredients. Such additional ingredients are for example salts originating from buffers used during the preparation of the hydrogel, such as phosphates, borates, bicarbonates, or other buffer agents such as triethanolamine. In certain embodiments of the present invention sodium phosphate buffers (specifically, mono- and dibasic sodium phosphate) are used.

Optionally, preservatives may be used for the inserts of the present invention. However, as demonstrated also in the Examples by way of storage stability test data as well as by clinical results demonstrating that the inserts remain safe, the inventive inserts do not require the presence of preservatives in contrast to e.g. certain eye drops. As preservatives are believed to be also a cause for discomfort to the subject such as stinging and irritation of the eyes, in one embodiment of the invention, the inserts are free or essentially free of preservatives.

Formulation:

In certain embodiments, inserts according to the present invention comprise cyclosporine, a polymer network made from one or more polymer precursors as disclosed herein above in the form of a hydrogel, and optional additional components such as a surfactant, but also salts etc. remaining in the insert from the production process (such as phosphate salts used as buffers etc.).

In certain embodiments, the insert according to the present invention in a dried state contains from about 15% to about 80% by weight of the cyclosporine based on the total weight of the insert and from about 20% to about 60% by weight polymer units based on the total weight of the insert, or from about 30% to about 65% by weight of the cyclosporine based on the total weight of the insert and from about 25% to about 50% by weight polymer units based on the total weight of the insert, or from about 45% to about 55% by weight of the cyclosporine based on the total weight of the insert and from about 37% to about 47% by weight polymer units based on the total weight of the insert.

In one further particular embodiment, on a dry weight basis the cyclosporine to PEG ratio is from about 50% to 60% by weight cyclosporine to approximately 40% by weight PEG based on the total weight of the insert, the balance being phosphate salt and other excipients.

In certain embodiments, the balance of the insert in its dried state (i.e., the remainder of the formulation when cyclosporine, polymer hydrogel, such as PEG hydrogel, and the optional surfactant have already been taken account of) may be salts remaining from buffer solutions as disclosed above. In certain embodiments, such salts are phosphate, borate or (bi) carbonate salts. In one embodiment the buffer salt is sodium phosphate (mono- and/or dibasic).

The amounts of the cyclosporine and the polymer(s) may be varied, and other amounts of cyclosporine and the polymer hydrogel may be used to prepare inserts according to the invention.

In certain embodiments, the amount of drug within the formulation is less than about two times the amount of the polymer (e.g., PEG) units, but may be higher in certain cases, but it is desired that the mixture comprising, e.g., the precursors, buffers and drug (in the state before the hydrogel has gelled completely) can be uniformly cast into a mold or tubing.

In one embodiment of the invention, the hydrogel after being formed and prior to being dried, i.e., in a wet state, comprises from about 3% to about 20% polyethylene glycol representing the polyethylene glycol weight divided by the fluid weight×100. In one embodiment, the hydrogel in a wet state comprises about 7.5% to about 15% polyethylene glycol representing the polyethylene glycol weight divided by the fluid weight×100.

In certain embodiments, solid contents of about 10% to about 30% (w/v) (wherein "solids" means the combined weight of polymer precursor(s), salts and the drug in solution) are utilized for forming the hydrogel for the inserts according to the present invention.

In certain embodiments, the water content of the hydrogel in its dry (dehydrated/dried) state, e.g. prior to insertion into the canaliculus of the eye, may be very low, such as not more than 1% by weight of water. In other words, in certain embodiments, the insert in a dried state contains not more than about 1% by weight water. The water content may in certain embodiments also be lower than that, e.g. not more than 0.25% by weight or not more than 0.1% by weight, based on the total weight of the insert.

Dimensions of the Insert and Dimensional Change Upon Hydration Through Stretching:

The dried insert may have different geometries, depending on the method of manufacture, such as the use of mold or tubing into which the mixture comprising the hydrogel precursors including the cyclosporine is cast prior to complete gelling. In one embodiment, the insert has an cylindrical or essentially cylindrical shape, with a round or essentially round cross-section. The shape of the insert may also be described as a fiber (as the length of the cylinder is much in excess of the diameter) or rod.

The polymer network, such as the PEG network, of the hydrogel insert according to certain embodiments of the present invention may be semi-crystalline in the dry state at or below room temperature, and amorphous in the wet state. Even in the stretched form, the dry insert may be dimensionally stable at or below room temperature, which may be advantageous for inserting the insert into the canaliculus.

Upon hydration of the insert in the eye (which can be simulated by immersing the insert into PBS, pH 7.4 at 37° C.) the dimensions of the insert according to the invention may change: generally, the diameter of the insert may increase, while its length may decrease or at least may stay the same or essentially the same. An advantage of this dimensional change is that, while the insert in its dry state is sufficiently thin for an easy insertion into the canaliculus, once it has been placed in the canaliculus, the insert does not only become shorter to improve wearing comfort with respect to the short, vertical part of the canaliculus and the corresponding limited space available, but also becomes larger in diameter, so that it tightly fits against the canaliculus walls, locks the insert in place and thus prevents unintentional migration and loss of the insert. As it also may become softer, it is comfortable to wear despite the tight fit. In certain embodiments, the dimensional change is enabled at least in part by the "shape memory" effect introduced into the insert by means of stretching the insert in the longitudinal direction during its manufacture (as also disclosed below in the section "Method of manufacture"). In certain embodiments, the stretching may either be performed in the dry or in the wet state, i.e., after drying the hydrogel insert, or before drying. It is noted that if no stretching is performed, and the hydrogel insert is only dried and cut into a desired length, the dimensions of the insert may not change substantially, or the insert may increase in both diameter and length upon hydration. If this is not desired, the hydrogel fiber may be dry or wet stretched, i.e. stretched prior to or after drying. In particular, the fiber may be stretched prior to drying.

In pre-formed dried hydrogels, a degree of molecular orientation may be imparted by dry-stretching the material then allowing it to solidify, locking in the molecular orientation. This can be accomplished in certain embodiments by drawing the material (optionally while heating the material to a temperature above the melting point of the crystallizable regions of the material), then allowing the crystallizable regions to crystallize. Alternatively, in certain embodiments the glass transition temperature of the dried hydrogel can be used to lock in the molecular orientation for polymers such as PVA that have a suitable glass transition temperature. Still another alternative is to stretch the gel prior to complete drying (also referred to as "wet stretching") and then drying the material while under tension. The molecular orientation provides one mechanism for anisotropic swelling upon introduction into a hydrating medium such as the vitreous. Upon hydration the insert of certain embodiments will swell only in the radial dimension, while the length will either decrease or be maintained or essentially maintained. The term "anisotropic swelling" means swelling preferentially in one direction as opposed to another, as in a cylinder that swells predominantly in diameter, but does not appreciably expand (or does even contract) in the longitudinal dimension.

The degree of dimensional change upon hydration may depend inter alia on the stretch factor. The stretch factor as used herein refers to the factor the hydrogel is stretched at as measured in stretching direction, i.e. the change in length and not in diameter, immediately before and after stretching, without taking any eventual further dimensional change (e.g. due to drying or rehydration) into account. As an example, stretching at e.g. a stretch factor of about 1.3 (e.g. by means of wet stretching) may have a less pronounced effect or may not change the length during hydration to a large extent. In contrast, stretching at e.g. a stretch factor of about 1.8 (e.g. by means of wet stretching) may result in a markedly shorter length during hydration. Stretching at e.g. a stretch factor of 4 (e.g. by means of dry stretching) could result in a much shorter length upon hydration (such as, for example, a reduction in length from 15 to 8 mm). One skilled in the art will appreciate that other factors besides stretching can also affect swelling behavior.

One aspect of the present invention is a sustained release biodegradable intracanalicular insert comprising a hydrogel and cyclosporine in the form of a fiber, wherein the fiber has been stretched.

In certain embodiments, the fiber has been stretched by a stretch factor in the longitudinal direction of from about 1.0 to about 4.0, or from about 1.5 to about 3.0, or of about 2.7.

Among other factors influencing the possibility to stretch the hydrogel and to elicit dimensional change of the insert upon hydration is the composition of the polymer network. In the case PEG precursors are used, those with a lower number of arms (such as 4-armed PEG precursors) contribute in providing a higher flexibility in the hydrogel than those with a higher number of arms (such as 8-armed PEG precursors). If a hydrogel contains more of the less flexible components (e.g. a higher amount of PEG precursors containing a larger number of arms, such as the 8-armed PEG units), the hydrogel may be firmer and less easy to stretch without fracturing. On the other hand, a hydrogel containing more flexible components (such as PEG precursors containing a lower number of arms, such as 4-armed PEG units) may be easier to stretch and softer, but also swells more upon hydration. Thus, the behavior and properties of the insert once it has been placed into the eye (i.e., once the hydrogel becomes (re-)hydrated) can be tailored by means of varying structural features as well as by modifying the processing of the insert after it has been initially formed.

Exemplary dimensions of inserts used in the Examples herein below are provided in Table 2.1 of the Examples section. The dried insert dimensions inter alia depend on the amount of cyclosporine incorporated as well as the ratio of cyclosporine to polymer units and can also be controlled by the diameter and shape of the mold or tubing in which the hydrogel is allowed to gel. Furthermore, the diameter of the insert is further determined inter alia by (wet or dry) stretching of the hydrogel fiber once formed. The dried fiber (after stretching) is cut into segments of the desired length to form the insert. The diameter and the length of the insert can thus be adapted as desired. On the other hand, the anatomical dimensions of the lacrimal canaliculus provide certain dimensional requirements to an intracanalicular insert to be met.

In certain embodiments, the insert is in the form of a fiber. The fiber may have an average length of about 1.5 mm to about 4.0 mm and an average diameter of not more than 0.8 mm in its dried state, an average length of about 2.0 mm to about 2.5 mm and an average diameter of not more than 0.62 mm in its dried state, or an average length of about 2.5 mm to about 2.9 mm and an average diameter of not more than 0.62 mm in its dried state.

The inventive inserts are in certain embodiments, as also shown in the examples (see in particular Example 2), stable upon storage, and the product dimensions do not change or do not substantially upon long term storage.

Thus, in certain embodiments, the insert after at least 3 months, at least 6 months or at least 12 months of storage at a temperature of from 2 to 8° C. is in the form of a fiber that has an average length of about 2.5 mm to about 2.9 mm and an average diameter of not more than 0.62 mm in its dried state.

The insert dimensions can e.g. be adjusted by selecting an appropriate active concentration in view of the dose of cyclosporine to be incorporated in the insert. By increasing the active concentration, the insert dimensions can be reduced. On the other hand, the active concentration also affects the release behavior as well as insert properties and qualities such as swelling behavior or diameter after drying (see in particular Example 1.1). The inventors have surprisingly found in certain embodiments that certain combinations of insert dimensions, active concentration and/or dose would result not only in high quality inserts with appropriate swelling behavior allowing easy manufacture, easy administration and high wearing comfort, but would also provide an effective release over an extended period of time.

In view of the above, one aspect of the present invention is a sustained release biodegradable intracanalicular insert comprising a hydrogel and cyclosporine in an amount of about 360 µg, in the form of a fiber (or cylinder) that has an average length of about 2.5 mm to about 2.9 mm and an average diameter of not more than about 0.62 mm in its dried state. Also one aspect of the present invention is a sustained release biodegradable intracanalicular insert comprising a hydrogel and from about 45% to about 55% by weight of cyclosporine based on the total weight of the insert, in the form of a fiber (or cylinder) that has an average length of about 2.5 mm to about 2.9 mm and an average diameter of not more than about 0.62 mm in its dried state.

Such inserts, but also the inventive inserts in certain other embodiments may decrease in length and increase in diameter upon hydration in vivo in the eye, i.e. in the lacrimal canaliculus, or in vitro (wherein hydration in vitro is measured in phosphate-buffered saline at a pH of 7.4 at 37° C. after 24 hours) to an average diameter of at least 1.0 mm in expanded state after 10 minutes of hydration in vitro in phosphate-buffered saline at a pH of 7.4 at 37° C., or to an average diameter of at least 1.3 mm in equilibrium state after 24 hours of hydration in vitro in phosphate-buffered saline at a pH of 7.4 at 37° C. In one embodiment, this dimensional change can be achieved by dry stretching the hydrogel fiber at a stretch factor of about 1 to about 4, or a factor of about 1.5 to about 3.0, or about 2.7.

In certain embodiments, the stretching thus creates a shape memory, meaning that the insert upon hydration when administered into the lacrimal canaliculus, will shrink in length (also referred to as snap-back) and widen in diameter until it approaches (more or less) its equilibrium dimensions, which are determined by the original molded dimensions and compositional variables. While the narrow dry dimensions facilitate insertion of the product into the canaliculus, the widened diameter and shortened length after administration yield a shorter and thicker insert that is comfortable to wear and still is firmly locked in place so that the risk of unintended migration is minimized. Thus, in one aspect the present invention also relates to a method of imparting shape memory to a hydrogel mixture fiber comprising cyclosporine particles dispersed in the hydrogel by stretching the hydrogel mixture fiber in the longitudinal direction.

In Vitro Release:

The in vitro-release of cyclosporine from the inserts of the invention can be determined by various methods and e.g. under non-sink simulated physiological conditions in PBS (phosphate-buffered saline, pH 7.4) at 37° C., with daily replacement of PBS in a volume comparable to the tear fluid in the human eye.

The in vitro release tests may be used to compare different inserts (e.g. of different production batches, of different composition, and of different dosage strength etc.) with each other, for example for the purpose of quality control or other qualitative assessments.

In Vivo Release and Persistence:

In an embodiment of the present invention, when the dried insert of the present invention is inserted to the canaliculus, it becomes hydrated and changes its dimensions as disclosed above, and is then over time biodegraded and disintegrates until it has been fully disintegrated and any remains have been drained down the lacrimal duct. When the insert is biodegraded, such as through ester hydrolysis, it gradually may swell and soften. As recognized by the inventors from the clinical studies presented in the Examples section herein below, an insert according to certain embodiments of the invention may persist several months, such as about 2 to about 4 months or longer, enabling a sustained release of cyclosporine again over several months.

After full disintegration of the insert, any remaining undissolved cyclosporine particles may be drained through the lacrimal excretory system. Thus, the length of sustained release can be inter alia designed by way of adjusting the disintegration time if a sufficient amount of cyclosporine is included that lasts over the time the insert needs for complete disintegration. If in certain embodiments two inserts are used to treat one eye, e.g., one insert per each of the lower and upper canaliculus, to achieve a desired total dose, they may be designed to disintegrate over the same or substantially the same time.

In the lacrimal canaliculus, the insert of the invention in certain embodiments disintegrates within an extended period of time, e.g. within about 1 to about 6 months after insertion, or within about 2 to about 4 months after insertion, or within about 2 to about 3 months after insertion, or within about 3 to about 4 months after insertion. This has been demonstrated in the clinical trials, see the Examples section, in particular Example 4.

In one embodiment, the insert after insertion to the canaliculus releases a therapeutically effective amount of cyclosporine over a period of at least about 1 month, at least about 2 months, at least about 3 months, or at least 4 months after insertion.

In one embodiment of the invention, cyclosporine is released from the insert after insertion at an average rate of about 0.1 µg/day to about 10 µg/day, or about 1 µg/day to about 5 µg/day, or about 2 µg/day to about 4 µg/day.

In one embodiment of the invention, cyclosporine is released from the insert after insertion to a human subject at an average rate of about 0.1 µg/day to about 10 µg/day, or about 1 µg/day to about 5 µg/day, or about 2 µg/day to about 4 µg/day.

Pre-clinical studies in animals as well as clinical studies in humans, as presented in the Examples section herein, have shown that the inserts of certain embodiments of the invention may continuously release therapeutically effective amounts of cyclosporine over an extended period of time, until the inserts are fully disintegrated. In certain embodiments, however, the entire amount of cyclosporine contained in the insert is released from the insert prior to complete biodegradation of the insert.

One aspect of the present invention is a sustained release biodegradable intracanalicular insert comprising a hydrogel and cyclosporine in an amount of about 360 µg dispersed within the hydrogel, wherein the insert after insertion to the canaliculus releases a therapeutically effective amount of cyclosporine over a period of at least about 3 months after insertion.

In certain embodiments, the tear fluid concentration of cyclosporine after insertion to a human subject ranges from about 0.1 µg/mL to about 10 µg/mL.

In certain embodiments, the tear fluid concentration of cyclosporine after insertion of the insert ranges from about 0.1 µg/mL to about 10 µg/mL, or from about 1 µg/mL to about 5 µg/mL.

In certain embodiments, the insert disintegrates in the canaliculus prior to complete solubilization of the cyclosporine particles contained in the insert.

The insert of the invention in certain embodiments may be designed to disintegrate in the lacrimal canaliculus within about 1 to about 6 months after insertion, or within about 2 to about 4 months after insertion, or within about 2 to about 3 months after insertion, or within about 3 to about 4 months after insertion.

In one embodiment, where the polymer network of the hydrogel is crosslinked based on linking groups derived from NHS ester end groups such as the SG-, the SAP or similar groups as disclosed above, the persistence of the hydrogel within an aqueous environment and in the canaliculus depends inter alia on the hydrophobicity of the carbon chain in proximity to the degradable ester group. In the inserts used in the Examples herein, this carbon chain comprises 3 or 4 carbon atoms as it stems from the SG and SAP functional group of the 4a20 k PEG precursor. This may provide an extended persistence in the human eye of from about 2 to about 3 months or from about 3 to about 4 months, respectively. In other embodiments, different precursors than the 4a20 kPEG-SG-/-SAP and the crosslinker trilysine may be used to prepare hydrogel inserts that biodegrade in the human eye and have similar or different persistence as the inserts exemplified in the Examples.

In certain embodiments, the hydrogel insert softens over time as it degrades, which may depend inter alia on the structure of the linker that crosslinks the PEG units in the hydrogel. An insert as used in the examples of the present application formed from a 4a20 kPEG-SAZ and an 8a20 kPEG-NH$_2$ softens rather slowly over time.

Mechanism of Release:

Without wishing to be bound by theory, the mechanism of release of cyclosporine from an insert of the invention may be explained as follows:

As outlined above, the hydrophobic active agent cyclosporine is practically non-miscible with the hydrophilic hydrogel material. Once inserted and placed in the canaliculus, the insert is in contact with tear fluid, which slowly imbibes and penetrates the hydrophilic hydrogel.

Biodegradation, i.e. the hydrolytic degradation of the hydrogel matrix leads to the hydrogel getting softer and allows the tear fluid to penetrate even further, but the hydrophobic active, in particular in form of uniformly dispersed cyclosporine particles, remains entrapped within the hydrogel matrix and is released by slow partitioning into the hydrogel due to the low solubility in aqueous solutions.

Also, it is believed, without wishing to be bound to a particular theory, that the tear fluid on top of an intracanalicular insert provides a fluid column that tends to allow active release to be limited by the cross-sectional area of the proximal portion of the plug. The walls of the canaliculus seem to release the drug at a rate that is much slower relative to the depletion of the therapeutic agent through the fluid column, and/or the canaliculus walls may become saturated with the drug so that release through the walls is slowed. Thus, in certain embodiments, the intracanalicular insert of the present invention does not necessitate and in particular does not comprise any barrier or reservoir system (e.g. a coating on the side wall of the insert blocking and limiting release of the active to a release from the cross-sectional area) as has been previously proposed, which are complex and more difficult to manufacture.

Drug release from the cross-sectional area of the insert into the tear fluid may happen first at the outer region of the hydrogel (i.e., the drug particles that are located in the region of the hydrogel closer to the punctum get dissolved and diffuse out first, while those located closer to the other end of the insert, closer to the lacrimal duct diffuse out last) that is in contact with the liquid environment. Thereby, in certain embodiments, the region of the hydrogel closer to the punctum becomes devoid of drug particles. This region is therefore also called the "clearance zone", which is limited to dissolved drug only, with a concentration at or below the solubility of the drug.

In certain embodiments in which a clearance zone has formed upon drug dissolution and diffusion out of the hydrogel, this area of the hydrogel develops voids and becomes softer and weaker. Concurrently with the drug diffusing out of the hydrogel, the hydrogel may also be slowly degraded by means of, e.g., ester hydrolysis in the aqueous environment of the eye. This degradation occurs uniformly throughout the bulk of the hydrogel. At advanced stages of degradation, distortion and erosion (also termed disintegration as used herein) of the hydrogel begins to occur. As this happens, the hydrogel becomes softer and more liquid (and thus its shape becomes distorted) until the hydrogel finally disintegrates completely and any remaining bits of the hydrogel and/or active are cleared away by the lacrimal drainage system.

As cyclosporine is a relatively low solubility drug, undissolved cyclosporine particles may remain at the time the insert is fully disintegrated, i.e. the insert may disintegrate in the canaliculus prior to complete solubilization of the cyclosporine particles contained in the insert, but as outlined above, in such a case any remaining active particles are cleared away by the lacrimal drainage system.

In one embodiment, however, the entire amount of cyclosporine is released prior to the complete disintegration of the hydrogel. As the hydrogel may hold the cyclosporine particles in place and prevent them from agglomeration, the release of cyclosporine from the hydrogel can be maintained at a relatively constant rate.

II. Manufacture of the Insert

In certain embodiments, the present invention also relates to a method of manufacturing a sustained release biodegradable intracanalicular insert comprising a hydrogel and cyclosporine as disclosed herein. In certain embodiments, the method comprises the steps of a) preparing a precursor mixture containing hydrogel precursors and cyclosporine particles dispersed in the precursor mixture,
b) shaping the precursor mixture and allowing the hydrogel precursors to cross-link to form a polymer network and to obtain a shaped hydrogel mixture comprising the polymer network, and
c) drying the hydrogel mixture to provide the insert.

In one embodiment, the cyclosporine particles may be used in micronized form for preparing the insert, i.e. they are employed in the form of micronized particles and dispersed to prepare a precursor mixture wherein the micronized particles are homogeneously dispersed. In another embodiment, the cyclosporine may be used in non-micronized form for preparing the insert. Further details on the active principle cyclosporine have been disclosed in detail above and apply to the active used for the manufacture in all aspects.

The precursors for forming the hydrogel of certain embodiments have been disclosed in detail above in the section relating to the insert itself.

In certain embodiments, in step a) the precursor mixture is prepared by mixing an electrophilic group-containing multi-arm-polymer precursor with a nucleophilic group-containing crosslinking agent in a buffered aqueous solution in the presence of micronized cyclosporine particles.

In certain embodiments, in step a) the buffered aqueous precursor solution is prepared by dissolving the multi-arm-polymer precursor in an aqueous buffer solution and is then mixed with the buffered aqueous precursor suspension comprising the nucleophilic group-containing cross-linking agent and micronized cyclosporine particles within, e.g., 60 minutes.

In case PEG precursors are used to prepare a crosslinked PEG network, the method of manufacturing the insert in certain embodiments may comprise mixing an electrophilic group-containing multi-arm polyethylene glycol, such as 4a20 kPEG-SG or 4a20 kPEG-SAP, with a nucleophilic group-containing crosslinking agent such as trilysine in a buffered aqueous solution in the presence of micronized cyclosporine particles.

In certain embodiments, the molar ratio of the electrophilic groups to the nucleophilic groups in the PEG precursors is about 1:1, but the nucleophilic groups (such as the amine groups) may also be used in excess of the electrophilic groups, or vice versa, e.g. in a molar ratio ranging from about 1:2 to 2:1. In certain embodiments, the method comprises reacting 4a20 kPEG-SG or 4a20 kPEG-SAP with fluorescein-conjugated trilysine in a weight ratio ranging from about 30:1 to about 50:1

As shown in Example 1.4, treatment of the precursor mixture by vacuum degassing turned out to have a high impact on the insert quality. In particular, agglomeration of cyclosporine particles could be prevented. Thus, in certain embodiments, in step a) the precursor mixture containing cyclosporine particles is degassed under vacuum after mixing its component.

In certain embodiments, once the precursor mixture has been prepared as outlined for step a) above, the mixture can be shaped in step b) by casting into a suitable mold or tubing prior to complete gelling in order to provide the desired final shape of the hydrogel, i.e. in step b) the shaping of the precursor mixture consists of filling the precursor mixture into a mold or tubing prior to complete cross-linking in order to provide the desired final shape of the hydrogel mixture and allowing the hydrogel precursors to cross-link.

In case the insert should have the shape of a fiber, the reactive mixture may be filled into a fine diameter tubing, such as a polyurethane (PU) tubing, in order to provide for the extended cylindrical shape. Different geometries and diameters of the tubing may be used, depending on the desired final cross-sectional geometry of the hydrogel fiber, its initial diameter (which may still be decreased by means of stretching), and depending also on the ability of the reactive mixture to uniformly fill the tubing.

Thus, the inside of the tubing may have a round geometry or a non-round geometry such as a cross-shaped geometry. The tubing may have a round geometry with an inner diameter of, e.g., about 1 mm to about 3 mm or about 2.0 mm.

In certain embodiments, after the hydrogel has formed and has been left to cure to complete gelling, the hydrogel may be longitudinally stretched in the wet or dry state as already disclosed in detail herein above in the section relating to the dimensional change of the insert upon hydration. In certain embodiments, a stretching factor may be in a range of about 1 to about 4.5, or within other ranges also as disclosed above. When dry stretching is performed in certain embodiments, the hydrogel is first dried and then stretched. When wet stretching is performed in certain embodiments, the hydrogel is stretched in the wet (essentially undried) state and then left to dry under tension. Optionally, heat may be applied upon stretching. Further optionally, the fiber may additionally be twisted.

In certain embodiments, the insert is obtainable by preparing a precursor mixture containing hydrogel precursors and cyclosporine, filling the precursor mixture into a tubing, allowing the hydrogel precursors to crosslink in the tubing to provide a hydrogel mixture shaped as a fiber, and stretching the hydrogel mixture fiber to provide the insert.

In certain embodiments, the insert maintains its dimensions even after stretching as long as it is kept in the dry state at or below room temperature.

In certain embodiments, the inserts are separately packaged and sterilized e.g. by means of gamma irradiation.

The shape memory effect of the stretching has already been disclosed in detail above with respect to the properties of the insert. In certain embodiments, the degree of shrinking upon hydration depends inter alia on the stretch factor as already disclosed above.

In certain embodiments, the present invention thus also relates to a method of imparting shape memory to a hydrogel mixture fiber comprising cyclosporine particles dispersed in the hydrogel by stretching the hydrogel mixture fiber in the longitudinal direction.

Stretch factors for use in these methods of the invention may be utilized as already disclosed above.

III. Therapy

In certain embodiments, the present invention is further directed to a method of treating or preventing an ocular disease in a patient in need thereof, the method comprising administering to the patient a first sustained release biodegradable intracanalicular insert comprising a hydrogel and a cyclosporine as disclosed above.

In certain embodiments, said first insert is left to remain in the canaliculus until complete disintegration, or is removed prior to complete disintegration. In certain embodiments, said first insert may be designed to disintegrate in the canaliculus within an extended period of time, e.g. within about 1 to about 6 months, within about 2 to about 4 months, or within about 2 to about 3 months, or within about 3 to about 4 months after insertion, although in some cases it will take longer to disintegrate. Under normal circumstances, since the inserts disintegrate without the need of any action from the patient's side, the insert may remain in the canaliculus until complete disintegration. This is advantageous as the patient does not need to consult a physician or optician in order to have the insert removed. On the other hand, ongoing biodegradation will soften the insert, thus facilitating a premature removal if necessary by applying slight pressure to expulse the insert through the punctum to the outside or to move the insert further down canaliculus to be cleared through the nasolacrimal duct, in the unexpected event of e.g. an allergic reaction, wearing discomfort or other adverse events such as irritating sensations etc. Also, the softness of the first insert allows inserting a second insert without the need of prior removal of the first insert. By inserting the second insert, the first insert is further pushed into the canaliculus and remains there without wearing discomfort until disintegration is completed, or is pushed down the lacrimal drainage system. The second insert can be inserted e.g. as soon as the intended treatment period of the first insert has passed, or if the patient feels that the therapeutic effect wears of f.

Thus, in certain embodiments, a second insert can be inserted after at least 1 month or at least 2 months without prior removal of said first insert. In other embodiments, said first insert is removed prior to complete disintegration and a second insert is administered to replace the removed first insert.

One aspect of the invention is a method of treating dry eye disease in a subject, the method comprising the steps of:
(a) inserting a first biodegradable insert into a first canaliculus of a first eye of the subject, wherein the insert comprises:
    (1) a biodegradable hydrogel;
    (2) from about 100 µg to about 800 µg cyclosporine dispersed in the hydrogel;
    (3) wherein the cyclosporine releases from the insert over a period of at least about 2-months from the date of inserting the first insert in the subject, at an average rate of about 0.1 µg/day to about 10 µg/day; and
(b) after at least about 2-months from the date of inserting the first insert, inserting a second insert into the first canaliculus of the first eye in the subject, wherein the second insert is similar or substantially similar to the first insert.

In certain embodiments, said first insert is designed to disintegrate in the canaliculus within about 2 to about 3 months after insertion and said first insert is removed within 2 months after administration.

In certain embodiments the dose of cyclosporine per eye administered once for a treatment period of at least 2 months is from about 300 µg to about 400 µg cyclosporine. Other appropriate doses are disclosed further above.

In certain embodiments the ocular disease is a disorder of the tear film and ocular surface.

In certain embodiments the ocular disease is dry eye disease. In alternative embodiments, inserts and methods of the present invention can be used to treat other ocular surface diseases, such as blepharitis, allergic conjunctivitis and in particular atopic keratoconjunctivitis and vernal keratoconjunctivitis.

In some embodiments the ocular disease is associated with one or more conditions selected from the group consisting of burning sensation, itching, redness, singing, pain, foreign body sensation, visual disturbances, inflammation of the lacrimal gland, inflammation of the ocular surface, T-cell-mediated inflammation, presence of conjunctival T-cells in the tears and elevated levels of inflammatory cytokines in the tears.

In some embodiments the sustained release biodegradable intracanalicular insert comprising the hydrogel and cyclosporine of the present invention can be applied in preventing such ocular conditions in subjects at the risk of developing dry eye disease or any associated conditions, e.g. subjects wearing contact lenses.

In some embodiments the treatment is effective in improving tear production as measured by Schirmer's tear test in a patient with a Schirmer's score of less than 10 mm prior to administration, and/or is effective in reducing eye dryness symptoms as determined by one or more assessments selected from the group consisting of rating of the severity of symptoms of eye dryness on a visual analogue scale, rating of the frequency of symptoms of eye dryness on a visual analogue scale, determination of tear film break up time, Corneal Fluorescein Staining, Conjunctival Lissamine Green Staining, best corrected visual acuity, determination of ocular surface disease index and standard patient evaluation of eye dryness.

In some embodiments the treatment is effective in improving tear production as measured by Schirmer's tear test in a patient with a Schirmer's score of less than 10 mm prior to administration.

In certain embodiments, the dose per eye administered once for the treatment period is contained in one or in two inserts.

In certain embodiments, the insert is inserted into the lower canaliculus, or into the upper canaliculus, or one insert is inserted each into the lower and upper canaliculus. The insert may be inserted into the vertical part of the canaliculus.

Cyclosporine, per eye administered once for the treatment period may be contained in one or two inserts.

In certain embodiments the dose per eye administered once for the treatment period is contained in one insert as for instance in one insert comprising a dose of about 250 µg or about 360 µg cyclosporine.

In certain embodiments, the insert may be inserted into the canaliculus with the aid of a grasping device selected from the group consisting of a forceps, a tweezer, and an applicator In embodiments wherein two inserts are administered, the inserts are inserted concurrently as disclosed herein above. The inserts inserted concurrently can be the same or different.

In certain embodiments, the treatment period is at least 1 month, at least 2 months or at least 3 months. "Treatment period" according to one embodiment of the invention means that the therapeutic effect of an insert of the present invention once inserted is maintained or essentially maintained over that period of time. In other words, only one insertion (of the insert of the present invention) is required in certain embodiments for maintaining a therapeutic effect during the extended period of time referred to herein as "treatment period". This is a considerable advantage over currently used eye drops for treating dry eye disease, which require a much more frequent administration of several times a day, and thus substantially improves the patient's quality of life.

One aspect of the present invention is a method of treating dry eye disease in a patient in need thereof, the method comprising administering to the patient a sustained release biodegradable intracanalicular insert comprising a hydrogel and cyclosporine, wherein punctal occlusion and cyclosporine release to the eye provide a synergistic effect.

Such a synergistic effect may consist in a higher bioavailability of the cyclosporine when compared to administration of eye drops containing cyclosporine designed to provide the same daily release of cyclosporine, which can e.g. be determined by the amount of cyclosporine released to the tear fluid as calculated based on cyclosporine tear fluid concentration over time.

In certain embodiments the systemic concentration of cyclosporine is below quantifiable amounts. As systemic concentrations of cyclosporine are kept at a minimum, the risk of drug-to-drug interactions or systemic toxicity is also kept at a minimum. Therefore, in one embodiment additional medication(s) taken by the patients do not provide a significant risk. This is especially beneficial in older patients who are frequently suffering from ocular diseases and are additionally taking other medications.

One aspect of the present invention is the use of a sustained release biodegradable intracanalicular insert comprising a hydrogel and cyclosporine as disclosed above in the preparation of a medicament for the treatment of an ocular disease in a patient in need thereof as disclosed above, or for the treatment of dry eye disease/keratoconjunctivitis Sicca in a patient in need thereof as disclosed above.

One aspect of the present invention is a sustained release biodegradable intracanalicular insert comprising a hydrogel and cyclosporine as disclosed above for use in the treatment of an ocular disease in a patient in need thereof as disclosed above or for use in the treatment of dry eye disease/keratoconjunctivitis Sicca in a patient in need thereof as disclosed above.

One aspect of the present invention is a method of increasing tear production as measured by Schirmer's tear test in a patient with a Schirmer's score of less than 10 mm prior to administration, the method comprising administering to the patient the sustained release biodegradable intracanalicular insert comprising a hydrogel and cyclosporine as disclosed above.

In certain embodiments, in such a method, the Schirmer's score may increase by at least 2 mm at 6 weeks or by at least 3 mm at 12 weeks after insertion of the insert.

One aspect of the present invention is a method of reducing eye dryness symptoms as determined by one or more assessments selected from the group consisting of rating of the severity of symptoms of eye dryness on a visual analogue scale, rating of the frequency of symptoms of eye dryness on a visual analogue scale, determination of tear film break up time, Corneal Fluorescein Staining, Conjunctival Lissamine Green Staining, best corrected visual acuity, determination of ocular surface disease index OSDI, and standard patient evaluation of eye dryness SPEED, the method comprising administering to the patient the sustained release biodegradable intracanalicular insert comprising a hydrogel and cyclosporine as disclosed above.

In certain embodiments, in such a method, the total Corneal Fluorescein Staining value tCFS may decrease by at least 1.5 at 6 weeks or by at least 3 at 12 weeks after insertion of the insert.

In certain embodiments, in such a method, the rating of the severity of symptoms of eye dryness on a visual analogue scale may decrease by at least 10 at 2 weeks, or by at least 15 at 6 weeks after insertion of the insert.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example 1: Preparation of Cyclosporine Inserts

The cyclosporine inserts of the present application are essentially cylindrical (shaped as a fiber), with cyclosporine homogeneously dispersed and entrapped within a PEG-based hydrogel matrix to provide sustained release of cyclosporine based on its low solubility in the tear fluid.

I. Example 1.1: Evaluation of Drug Concentration

In order to evaluate the influence of drug concentration, three different formulations were prepared with a low, a medium and a high dose of cyclosporine. The composition of the three formulations is shown in Table 1.1.1 below.

TABLE 1.1.1

Composition of cyclosporine insert formulations

| | Hydrogel precursor mixture (pre-drying) | | |
|---|---|---|---|
| | Low dose | Medium Dose | High Dose |
| Cyclosporine Concentration (% w/w) | 5.12% | 9.90% | 14.58% |
| 4a20K PEG SG Concentration (% w/w) | 7.96% | 7.55% | 7.13% |
| Sodium Phosphate Dibasic Concentration (% w/w) | 0.55% | 0.52% | 0.50% |
| TLA Concentration (% w/w) | 0.22% | 0.21% | 0.20% |
| NHS-Fluorescein Concentration (% w/w) | 0.07% | 0.07% | 0.06% |
| Sodium Phosphate monobasic Concentration (% w/w) | 0.22% | 0.21% | 0.19% |
| Solids content | 14.13% | 18.46% | 22.66% |
| | Dried Insert | | |
| Drug Loading (% w/w) | 36.2% | 53.6% | 64.3% |

The inserts of Low, Medium and High Dose were prepared essentially in accordance with the manufacturing process as outlined for the study product inserts (see Example 1.5 below). However, no tyloxapol was used, the cyclosporine-containing syringe was first mixed with the syringe containing the multi-arm PEG solution before mixing with the trilysine acetate (TLA)/fluorescein solution-containing syringe, and no vacuum degassing was conducted.

Once casted, the hydrogel was cured, i.e. allowed to cross-link, and the strands of tubing were then stretched and dried in an incubator under a flow of nitrogen. The dried strands were removed from the flexible tubing and cut to length. The dimensional and physical properties were as follows:

TABLE 1.1.2

Dimensional and physical properties of Low, Medium and High Dose inserts

| Run Name | Dry Length (min) | Dry Diameter 1 (mm) | Dry Diameter 2 (mm) | Dry Diameter Ave (mm) | Dry Volume (mm$^3$) | Dry Aspect Ratio (−) | Dry (mg) | Dry (mg/mm$^3$) |
|---|---|---|---|---|---|---|---|---|
| Low Dose | 3.54 ± 0.51 | 0.56 ± 0.04 | 0.57 ± 0.05 | 0.57 ± 0.04 | 0.92 ± 0.26 | 0.97 ± 0.03 | 0.56 ± 0.15 | 0.61 |
| Medium Dose | 3.57 ± 0.36 | 0.47 ± 0.03 | 0.68 ± 0.07 | 0.58 ± 0.03 | 0.91 ± 0.15 | 0.7 ± 0.1 | 0.83 ± 0.13 | 0.90 |
| High Dose | 3.59 ± 0.34 | 0.81 ± 0.11 | 0.89 ± 0.13 | 0.85 ± 0.12 | 2.09 ± 0.7 | 0.91 ± 0.06 | 0.89 ± 0.3 | 0.43 |

The Low and High Dose formulations resulted in fibers with an undesirable "strawing", i.e. these fibers had large dry diameters and showed hollow holes in the middle of the fibers. As a result, the density of the strawed fibers was low.

In order to determine the "roundness" of the fibers, the cross-section diameter was measured on the thick as well as on the thin side, the lower diameter value was identified as diameter 1, the higher one as diameter 2, and the aspect ratio calculated as Aspect ratio=Diameter 1/Diameter 2

While the medium dose formulation did not show evidence of strawing, it produced flat fibers with a very low aspect ratio. The aspect ratio was 0.7 indicating a lack of roundness. Though the strawed fibers of Low and High Dose formulations were rounder, the low density produced much larger fibers than desired. The drug concentration had also an effect on the hydration properties of the inserts as summarized in Table 1.1.3 below:

TABLE 1.1.3

Hydration properties of Low, Medium and High Dose inserts

| Run Name | Wet (10 min) Length (mm) | Wet (10 mm) Diameter (mm) | Shrink Factor (%) | Wet Equilibrium (24 hr) Length (mm) | Wet Equilibrium (24 hr) Diameter (mm) | Shrink Factor (%) |
|---|---|---|---|---|---|---|
| Low Dose | 2.46 ± 0.29 | 1.78 ± 0.05 | 30% ± 3% | 2.55 ± 0.34 | 1.86 ± 0.04 | 27.9% ± 2% |
| Medium Dose | 2.99 ± 0.28 | 1.59 ± 0.09 | 16.3% ± 2.1% | 2.93 ± 0.3 | 1.7 ± 0.09 | 18% ± 1.5% |
| High Dose | 3.19 ± 0.3 | 1.61 ± 0.12 | 11.1% ± 2.2% | 3.14 ± 0.26 | 1.63 ± 0.09 | 12.3% ± 2.3% |

As can be seen, hydrated diameters were all significantly above the target of 1.45 mm and decreased with increasing dose, and the shrink factor also decreased with increasing dose.

II. Example 1.2: Evaluation of Surfactants

Presence of Surfactant

In order to evaluate the influence of surfactants being present in the insert, three different formulations were prepared, wherein one of the formulations contained no surfactant (control, Run 1), one contained 0.05% Tween® 20 (Run 2), and the third contained no surfactant but was prepared using ethanol (Run 3). The composition of the three formulations is shown in Table 1.2.1 below.

TABLE 1.2.1

Composition of eye osporine insert formulations with and without surfactant

| | Hydrogel precursor mixture (pre-drying) | | |
|---|---|---|---|
| | Run 1 | Run 2 | Run 3 |
| Cyclosporine Concentration (% w/w) | 9.79% | 9.84% | 10.66% |
| 4a20K PEG SG Concentration (% w/w) | 7.56% | 7.58% | 8.24% |
| Sodium Phosphate Dibasic Concentration (% w/w) | 0.52% | 0.52% | 0.57% |
| TLA Concentration (% w/w) | 0.21% | 0.21% | 0.22% |
| NHS-Fluorescein Concentration (% w/w) | 0.07% | 0.07% | 0.07% |

TABLE 1.2.1-continued

Composition of eye osporine insert formulations with and without surfactant

| | Hydrogel precursor mixture (pre-drying) | | |
|---|---|---|---|
| | Run 1 | Run 2 | Run 3 |
| Sodium Phosphate monobasic Concentration (% w/w) | 0.21% | 0.21% | 0.21% |
| Tween® 20 Concentration (% w/w) | 0.000% | 0.050% | 0.000% |
| Solids content | 18.35% | 18.48% | 19.98% |
| 4a20K PEG SO Concentration (% w/w) | 9.27% | 9.30% | 9.28% |
| Dried Insert | | | |
| Drug Loading (% w/w) | 53.3% | 53.3% | 53.4% |

The inserts of Runs 1 to 3 were prepared essentially in accordance with the manufacturing process as outlined for the study product inserts (see Example 1.5 below), i.e. by preparing one hydrogel suspension pre-cursor syringe containing a cyclosporine suspension in a trilysine acetate (TLA)/fluorescein aqueous solution (Run 1: containing no tyloxapol; Run 2: containing Tween® 20 instead of tyloxapol; Run 3: containing no tyloxapol but dissolved in ethanol instead of water) and a second hydrogel solution pre-cursor syringe containing a multi-arm PEG aqueous solution, mixing these two syringes and then casting into a subset of flexible tubing pieces by injecting the liquid suspension before the material cross-links and solidifies. No vacuum degassing was conducted. Once casted, the hydrogel was cured, i.e. allowed to cross-link, and the strands of tubing were then stretched and dried in an incubator under a flow of nitrogen. The dried strand was removed from the flexible tubing and cut to length. The dimensional and physical properties were as follows:

TABLE 1.2.2

Dimensional and physical properties of inserts with and without surfactant

| | Run # | Dry Length (mm) | Dry Diameter 1 (mm) | Dry Diameter 2 (mm) | Dry Diameter Ave (mm) | Dry Aspect Ratio (−) | Dry Mass (mg) | Dry Density (mg/mm³) |
|---|---|---|---|---|---|---|---|---|
| No Surfactant | 1 | 3.12 ± 0.03 | 0.41 ± 0.02 | 0.72 ± 0.04 | 0.57 ± 0.02 | 0.57 ± 0.05 | | 0.76 ± 1.02 0.05 |
| 0.05% Tween-20 | 2 | 3.16 ± 0.03 | 0.53 ± 0.02 | 0.54 ± 0.01 | 0.53 ± 0.01 | 0.96 ± 0.01 | | 0.76 ± 1.07 0.05 |
| Ethanol | 3 | 3.3 ± 0.18 | 0.76 ± 0.12 | 0.79 ± 0.18 | 0.77 ± 0.15 | 0.95 ± 0.06 | | 1.63 ± 1.01 0.62 |

In order to determine the "roundness" of the fibers, the cross-section diameter was measured on the thick as well as on the thin side, the lower diameter value was identified as diameter 1, the higher one as diameter 2, and the aspect ratio calculated as Aspect ratio=Diameter 1/Diameter 2

As can be seen, the addition of Tween® 20 led to a high aspect ratio, indicating round fibers. The average diameter was lower than the control and the density was higher, which is advantageous in terms of ease of insertion of the product. The control fiber of Run 1 stuck to the tubing during drying and had a low aspect ratio indicating flat fibers (see FIG. 1.2A).

Run 3, which investigated the use of ethanol, encountered major issues. The solution started evaporating within 1 minute of starting the cure, creating air bubbles in the fiber. The fibers were all broken and deformed when removed from the incubator which can be seen in FIG. 1.2.

Drug Concentration in the Presence of Surfactant

In order to evaluate the influence of drug concentration in the presence of surfactant, three different formulations were prepared with a low, a medium and a high dose of cyclosporine in the presence of D0.05% Tween® 20. The composition of the three formulations is shown in Table 1.2.3

TABLE 1.2.3

Composition of cyclosporine insert formulations comprising surfactant

| | Hydrogel precursor mixture (pre-drying) | | |
|---|---|---|---|
| | Low Dose | Medium Dose | High Dose |
| Cyclosporine Concentration (% w/w) | 5.70% | 10.84% | 15.20% |
| 4a20K PEG SG Concentration (% w/w) | 7.87% | 7.45% | 7.08% |
| Sodium Phosphate Dibasic Concentration (% w/w) | 0.54% | 0.51% | 0.49% |
| TLA Concentration (% w/w) | 0.22% | 0.20% | 0.19% |
| NHS-Fluorescein Concentration (% w/w) | 0.07% | 0.07% | 0.06% |
| Sodium Phosphate monobasic Concentration (% w/w) | 0.21% | 0.20% | 0.19% |

TABLE 1.2.3-continued

Composition of cyclosporine insert formulations comprising surfactant

| | Hydrogel precursor mixture (pre-drying) | | |
|---|---|---|---|
| | Low Dose | Medium Dose | High Dose |
| Tween ® 20 Concentration (% w/w) | 0.053% | 0.051% | 0.049% |
| Solids content | 14.67% | 19.33% | 23.27% |
| 4a20K PEG SO Concentration (% w/w) | 9.23% | 9.23% | 9.23% |
| | Dried Insert | | |
| Drug Loading (% w/w) | 38.9% | 56.1% | 65.3% |

The three inserts of Runs 1 to 3 were prepared essentially in accordance with the manufacturing process as outlined for the study product inserts (see Example 1.5 below), except that Tween® 20 was used instead of tyloxapol. No vacuum degassing was conducted. Once casted, the hydrogel was cured, i.e. allowed to cross-link, and the strands of tubing were then stretched and dried in an incubator under a flow of nitrogen. The dried strand was removed from the flexible tubing and cut to length. No sterilization was conducted. The dimensional and physical properties were as follows:

TABLE 1.2.4

Dimensional and physical properties of inserts comprising surfactant

|  | Dry Length (mm) | Dry Diameter 1 (mm) | Dry Diameter 2 (mm) | Dry Diameter Ave (mm) | Dry Volume (mm³) | Dry Aspect Ratio (–) | Dry Mass (mg) | Density (mg/mm³) |
|---|---|---|---|---|---|---|---|---|
| Low Dose | 2.72 ± 0.03 | 0.47 ± 0.02 | 0.47 ± 0.02 | 0.47 ± 0.02 | 0.48 ± 0.04 | 0.98 ± 0.01 | 0.54 ± 0.05 | 1.13 |
| Medium Dose | 2.73 ± 0.02 | 0.57 ± 0.02 | 0.56 ± 0.01 | 0.56 ± 0.01 | 0.69 ± 0.04 | 0.95 ± 0.03 | 0.72 ± 0.04 | 1.05 |
| High Dose | 2.71 ± 0.03 | 0.64 ± 0.07 | 0.65 ± 0.05 | 0.64 ± 0.05 | 0.89 ± 0.14 | 0.92 ± 0.08 | 0.87 ± 0.14 | 0.98 |

The aspect ratios were all above 0.9 indicating round fibers. The dry fiber diameters increased with increasing dose. However, the dry fiber diameters were all slightly elevated which is likely related to the fiber densities, which decreased with increasing dose.

FIG. 1.2C shows dry and hydrated inserts produced in this run. As can be seen, the higher the drug concentration, the more agglomeration seems to take place.

Table 1.2.5 below shows the hydrated insert characteristics at 10 minutes and 24 hours after hydration with PBS at 37° C. As can be seen, both hydrated diameter and shrink factor decrease with increasing dose. This indicates that the drug content has significant adverse effects on rehydration rate.

TABLE 1.2.5

Hydration properties of Low, Medium and High Dose inserts

|  | Wet (10 min) | | | Wet equilibrium (24 hours) | | |
|---|---|---|---|---|---|---|
|  | Length (mm) | Diameter (mm) | Shrink Factor (%) | Length (mm) | Diameter (mm) | Shrink Factor (%) |
| Low Dose | 2.11 ± 0.09 | 1.65 ± 0.04 | 22.4% ± 2.8% | 2.14 ± 0.12 | 1.74 ± 0.05 | 21.5% ± 4.1% |
| Medium Dose | 2.49 ± 0.04 | 1.46 ± 0.03 | 8.7% ± 1.80 | 2.47 ± 0.03 | 1.49 ± 0.02 | 9.1% ± 1.70 |
| High Dose | 2.62 ± 0.05 | 1.37 ± 0.04 | 3.3% ± 1.9% | 2.56 ± 0.08 | 1.41 ± 0.06 | 5.4% ± 3.5% |

Surfactant Type

In order to address agglomeration, the effect of various surfactants on the particle size of cyclosporine was determined. Surfactants were tested at maximum surfactant concentration per FDA guidance.

Stock solutions containing 0.05% Tween® 20 (PEG-20 sorbitan monolaurate), 4% Tween® 80 (PEG-80 sorbitan monolaurate), 0.5% Cremophor RH 40 (PEG-40 hydrogenated castor oil) and 0.3% Tyloxapol (ethoxylated 4-tert-octylphenol/formaldehyde condensation polymer) were prepared by adding PBS to a known weight of surfactant in glass vials. The surfactant solutions were then vortexed and sonicated. Solutions containing about 9-10% (w/w) of Cyclosporine were prepared by adding approximately 1 mL of surfactant/buffer stock solutions to about 100 mg of Cyclosporine in a vial. Controls were prepared with distilled water (DIW) or phosphate buffered saline (PBS) and did not contain surfactant. This solution was then vortexed and the particle size was measured by laser diffraction using a Beckman Coulter LS 13 320 based on the optical model "Fraunhofer.rf780z" with an obscuration value ranging from 7 to 9%.

Table 1.2.6 shows the solution concentrations and particle size. As can be seen, the use of surfactants significantly decreased the particle size suggesting decreased agglomeration. Of the surfactants tested, Tyloxapol showed the greatest reduction in particle size. Additionally, the particle size measured using tyloxapol was closest to those provided by the supplier which indicated a D10, D50, and D90 of 0.5, 2.1, and 7.5 μm respectively.

TABLE 1.2.6

Effect of surfactants on particle size of cyclosporine

|  | Surfactant solution | | | | | | |
|---|---|---|---|---|---|---|---|
| Surfactant | ~ (DIw) | ~ (PBS) | Tween® 20 | Tween® 80 | Chemophor RH 40 | Tyloxapol | Cyclosp. Specific. |
| Surfactant Added (mg) | 0 | 0 | 4.1 | 201.87 | 36.7 | 11.16 |  |
| Surfactant Concentration (%) | 0.000% | 0.000% | 0.050% | 3.826% | 0.496% | 0.298% |  |
| Cyclosporine A Concentration (%) | 9.782% | 9.581% | 9.654% | 9.711% | 8.683% | 10.128% |  |
| D90 [Average] (μm) | 31.6 | 31.8 | 26.7 | 22.7 | 9.5 | 5.4 | 7.5 |
| D50 [Average] (μm) | 17.4 | 16.9 | 1..8 | 4 | 3 | 2.3 | 2.1 |
| D10 [Average] (μm) | 4 | 4.1 | 1.7 | 1.1 | 0.9 | 0.9 | 0.5 |
| D90 [StDev] (μm) | 2.8 | 2.4 | 1.7 | 13.4 | 0.1 | 0.1 |  |
| D50 [StDev] (μm) | 1.6 | 1.9 | 0 | 0.1 | 0.1 | 0.1 |  |
| D10 [StDev] (μm) | 0.6 | 0.8 | 0 | 0 | 0 | 0 |  |

I. Example 1.3: Evaluation of Vacuum Degassing

In order to evaluate the effect of vacuum degassing, 600 g dose cyclosporine inserts were prepared with a hydrogel precursor mixture concentration of 0.3% (w/w) for Tyloxapol as well as 9% (w/v) for the 4a20 k PEG-SG. The composition of the insert formulation is shown in Table 1.3.1 below.

TABLE 1.3.1

Composition of cyclosporine insert formulations for evaluating vacuum degassing

|  | Hydrogel precursor mixture (pre-drying) | Dry Insert |
|---|---|---|
| Cyclosporine Concentration (% w/w) | 15.34% | 64.825% |
| 4a.20K PEG SG Concentration (% w/w) | 7.10% | 30.013% |
| Sodium Phosphate Dibasic Concentration (% w/w) | 0.49% | 2.077% |
| TLA Concentration (% w/w) | 0.20% | 0.829% |
| NHS-Fluorescein Concentration (% w/w) | 0.06% | 0.271% |
| Sodium Phosphate monobasic Concentration (% w/w) | 0.18% | 0.759% |
| Tyloxapol Concentration (% w/w) | 0.290% | 1.225% |
| Solids Content | 23.67% | 100.000% |
| Dried Insert | | |
| Drug Loading (% w/w) | | 64.8% |

Three different sets of inserts were prepared using the same manufacturing process, except for the following details concerning the treatment of the hydrogel suspension pre-cursor syringe containing cyclosporine, tyloxapol and trilysine acetate/fluorescein after mixing its component and before further mixing with the PEG-containing hydrogel solution pre-cursor.

For the first set of inserts, the hydrogel suspension contained in the syringe was treated by (i) priming the syringe (as is customary done for all formulations), vortexing the suspension for 3 minutes and manually degassing. Manual degassing was conducted by pulling back the plunger of the syringe that has been closed with a cap in order to create vacuum and then uncapping the syringe, thus releasing the vacuum and collapsing large air bubbles. As a next step (ii), the hydrogel suspension pre-cursor was put in a vacuum chamber and degassed before mixing with the hydrogel solution pre-cursor. The hydrogel suspension pre-cursor for the second set of inserts was treated essentially in the same way, except that the hydrogel suspension pre-cursor was further sonicated in a step (iii) after step (ii). The hydrogel suspension pre-cursor of the third set of inserts was prepared in the same way as for the second set, except that step (ii) of degassing in the vacuum chamber was omitted. A summary of the preparation steps is given in Table 1.3.2 below

TABLE 1.3.2

Evaluation of vacuum degassing

| Steps | First set of Insert | Second set of Insert | Third set of Insert |
|---|---|---|---|
| (i) prime syringe, vortex 3 minutes, then manually degas | Yes | Yes | Yes |
| (ii) degassing in vacuum chamber | Yes | Yes | No |
| (iii) sonication | No | Yes | Yes |

The first set of inserts, obtained with merely vacuum degassing, had little to no agglomerates. The second set of inserts, obtained with both vacuum degassing and sonication, had many large agglomerates and would not fit in the cutting device. The third set of inserts obtained with sonication but no vacuum degassing had some agglomerates but looked otherwise good (FIG. 1.3).

II. Example 1.4: Evaluation of Drug Particle Size

Further inserts have been prepared to evaluate and to determine the optimal particle size of the drug substance.

Effect of Sieving Cyclosporine Large Particles

In order evaluate the effect of sieving to exclude larger particles, 400 μg dose cyclosporine inserts were prepared with a hydrogel precursor mixture concentrations of 0.3% (w/w) for Tyloxapol as well as 9% (w/v) for the 4a20 k PEG-SG. The composition of the formulation is shown in Table 1.4.1 below.

TABLE 1.4.1

Composition of cyclosporine insert formulations for evaluating sieving effect

|  | Hydrogel precursor mixture (pre-drying) | Dry Insert |
|---|---|---|
| Cydosporine Concentration (% w/w) | 9.818% | 53.010% |
| 4a20K PEG SG Concentration (% w/w) | 7.530% | 40.656% |
| Sodium Phosphate Dibasic Concentration (% w/w) | 0.525% | 7.833% |
| TLA Concentration (% w/w) | 0.206% | 1.110% |
| NHS-Fluorescein Concentration (% w/w) | 0.069% | 0.371% |
| Sodium Phosphate monobasic Concentration (% w/w) | 0.065% | 0.351% |
| Tyloxapol Concentration (% w/w) | 0.309% | 1.670% |
| Solids Content | 18.521% | 100.000% |
| Dried Insert | | |
| Drug Loading (% w/w) | | 53.01% |

The cyclosporine used was sieved and the particle size fractions indicated in Table 1.4.1 below were used. During manufacture, certain of the casted strands broke and could not be used, as summarized also in Table 1.4.2 below. The dry density and the drug load per insert is shown in FIG. 1.4A.

Table 1.4.2 Fractions of Particle size used and breakage failures of casted strands

TABLE 1.4.2

Fractions of Particle size used and breakage failures of casted strands

|  | Fraction 1 | Fraction 2 | Fraction 3 |
|---|---|---|---|
| Particle size fraction | 25-32 μm | 32-53 μm | 53-76 μm |
| Rate of breakage failure in casted strands | 1/2* | 1/6 | All strands broke |

*Other causes of breakage failure identified, e.g. air entrainment in the gel during casting It can thus be concluded that high particle size has severe negative impacts.

Effect of Cyclosporine Particle Size on Hydration, Dry Density and Mechanical Failure In order to evaluate the effect of different particle sizes, inserts were prepared using micronized cyclosporine particles with five different particle size distributions (PSDs). The composition of the five formulations is shown in Table 1.4.3 below.

TABLE 1.4.3

Composition of cyclosporine insert formulations

| | Hydrogel precursor mixture (pre-drying) | | | | |
|---|---|---|---|---|---|
| | Small 1 | Small 2 | Medium-small | Medium | Large |
| Cyclosporine Concentration (% w/w) | 9.88% | 14.01% | 9.78% | 9.86% | 9.89% |
| Multi-arm PEG | | | | | |
| 4a20K PEG SG | 7.58% | 3.79% | 3.77% | 3.77% | 3.78% |
| 4a20K PEG SAP Concentration (% w/w) | — | 3.97% | 3.79% | 3.77% | 3.78% |
| Sodium Phosphate Dibasic Concentration (% w/w) | 0.52% | 0.50% | 0.52% | 0.52% | 0.52% |
| TLA Concentration (% w/w) | 0.21% | 0.20% | 0.21% | 0.21% | 0.21% |
| NHS-Fluorescein Concentration (% w/w) | 0.07% | 0.07% | 0.07% | 0.07% | 0.07% |
| Sodium Phosphate monobasic Concentration (% w/w) | 0.07% | 0.06% | 0.07% | 0.07% | 0.07% |
| Tvioxapoi Concentration (% w/w) | 0.31% | 0.29% | 0.31% | 0.31% | 0.31% |
| Solids content | 22.34% | 72.34% | 18.66% | 18.58% | 18.63% |
| | | Dried Insert | | | |
| Drug Loading (% w/w) | 53.00% | 62.70% | 52.43% | 53.07% | 53.07% |

The d10, d50 and d90 values of the cyclosporine used are indicated in Table 1.4.4 below.

TABLE 1.4.4

Particle sizes of cyclosporine used

| | Small 1 | Small 2 | Medium-small | Medium | Large |
|---|---|---|---|---|---|
| d10 [μm] | 1.0 | 1.1 | 1.3 | 1.5 | 1.8 |
| d50 [μm] | 4.4 | 5.57 | 8.7 | 12.3 | 17.9 |
| d90 [μm] | 28.9 | 37.6 | 34.8 | 38.4 | 43.2 |

The following has been observed upon manufacturing: inserts prepared with larger CSI particles tended to have a larger dry diameter (see FIG. 1.4B) while the density decreases with CSI particle size (see FIG. 1.4Q). Smaller CSI particles resulted in smoother insert surface (see FIG. 1.4D showing microscopic images taken under a stereomicroscope with a camera). Inserts from small and small/medium particles on surface looked covered with PEG. Rough surface with significant irregularities and deformations were spotted on inserts prepared with medium and large particles. The medium particles led to the highest breakage rate during drying. Larger particles resulted in better hydration behavior and swelling (see FIG. 1.4E).

In conclusion, while larger particle improved the swelling and snap-back, it also led to more strand breakage. Additionally, high dose formulation demonstrated more breakage than low and medium dose formulations, and the removal of very large particulates (>45 microns) via sieving significantly improved breakage.

All in all, a particle size between "small" and "medium" balances both the density gains and fiber smoothness from small particles and the rehydration rates of medium particles which achieve reduced strand breakage.

III. Example 1.5: Preparation of Clinical Trial Supporting Inserts

In the following, the preparation process of the study product inserts will be described that are used in the human clinical study (Formulations 1, 2A, 2B and 3, see Example 4) and in the high dose beagle dog study (Formulations 4A and 4B, see Example 3.6). The study product inserts are based on a medium-persistent cyclosporine/hydrogel-formulation based on PEG-SG (Formulations 1 and 4A, designed to last approximately 2 to 3 months), a long-persistent cyclosporine/hydrogel-formulation based on PEG-SAP (Formulation 2A and 4B, designed to last approximately 3 to 4 months), and two hydrogel vehicle (HV) formulations without cyclosporine, serving as placebo, one long-persistent formulation based on PEG-SAP (Formulation 2B, designed to last approximately 3 to 4 months) and a short-persistent formulation based on PEG-SS (Formulation 3, designed to last approximately 1 week).

The cyclosporine-containing inserts had a target diameter of 0.55 mm+0.03 mm and a target length of 2.72 mm+0.08 mm, while the HV inserts had a target diameter of 0.41 mm±0.05 mm and a target length of 2.72 mm±0.08 mm. The composition of the formulations is shown in Table 1.5 below.

TABLE 1.5

Composition of cyclosporine study product insert formulations

| | Nominal Composition (μg, dry basis) | | | | | |
|---|---|---|---|---|---|---|
| Ingredient | Form. 1, SG | Form. 2A, SAP | Form. 2B, SAP | Form. 3, SS | Form. 4A SG | Form. 4B SAP |
| Cyclosporine | 384 | 390 | 0 | 0 | 773 | 772 |
| PEG | | | | | | |
| 4-arm 201K PEG SG | 295 | — | — | — | 389 | — |
| 4-arm 20K PEG SAP | — | 300 | 307 | — | — | 389 |
| 4-arm 20K PEG SS | — | — | — | 350 | — | — |
| Trilysine Acetate | 8 | 8 | 8 | 10 | 11 | 11 |
| Sodium Phosphate Dibasic, USP | 21 | 56 | 58 | 24 | 27 | 27 |
| Sodium Phosphate Monobasic, USP | 3 | 3 | 3 | 3 | 3 | |
| NHS-Fluorescein | 3 | 3 | 3 | 3 | 4 | 4 |
| Tyloapol, USP | 12 | 12 | 13 | 14 | 16 | 16 |
| TOTAL | 725 | 771 | 390 | 404 | 1222 | 1221 |

1. Brief Summary of Preparation Process

To form the polymer network of the cyclosporine-comprising inserts, two pre-cursor syringes were prepared: one hydrogel suspension pre-cursor syringe containing a cyclosporine suspension in a tyloxapol and trilysine acetate (TLA)/fluorescein solution, and a second hydrogel solution pre-cursor syringe containing a multi-arm PEG (4 arm 20K PEG based on a pentaerythritol core structure, containing amine reactive NHS groups) solution. The two syringes were mixed and then casted into a subset of flexible tubing pieces by injecting the liquid suspension before the material cross-links and solidifies. Once casted, the hydrogel was cured, i.e. allowed to cross-link. The strands of tubing containing the cyclosporine entrapped within the hydrogel network were then stretched and dried in an incubator under a flow of nitrogen. The dried strand was removed from the flexible tubing, cut to length, and stored in vials. The drug product was then packaged in a protective foam carrier which was heat-sealed under a nitrogen environment into a laminated foil pouch. The drug product was sterilized using e-beam radiation for cyclosporine containing formulations and gamma irradiation for HV formulations.

The HV placebo inserts were prepared in the same way, except that the amount of excipients used was adapted in accordance with the composition of Table 1 (variation in the multi-arm PEG), and in particular that no cyclosporine was used.

II. Preparation of Hydrogel Suspension Pre-Cursor Syringe

The same procedure and quantities are used for Formulations 1 and 2A with the exception of the type of multi-arm PEG and the amount of sodium phosphate dibasic used. For Formulations 4 and 5, the amount of cyclosporine was also adapted in accordance with the composition given in Table 1.5 above.

The hydrogel suspension pre-cursor syringe consisted of a mixture of two different additional pre-cursor syringes.

One syringe contained micronized cyclosporine suspended in a tyloxapol solution, prepared by weighing and suspending 704.8 mg±5.0 mg of micronized cyclosporine (d50: 5~8 µm, d100: ≤45 µm) in 2,775.0 mg±20.0 mg of a 0.8 wt-% solution of tyloxapol in water for injection (WFI). For the HV formulations (formulations 2B and 3), the syringe contained the 0.8 wt-% tyloxapol solution only.

Figure 2:
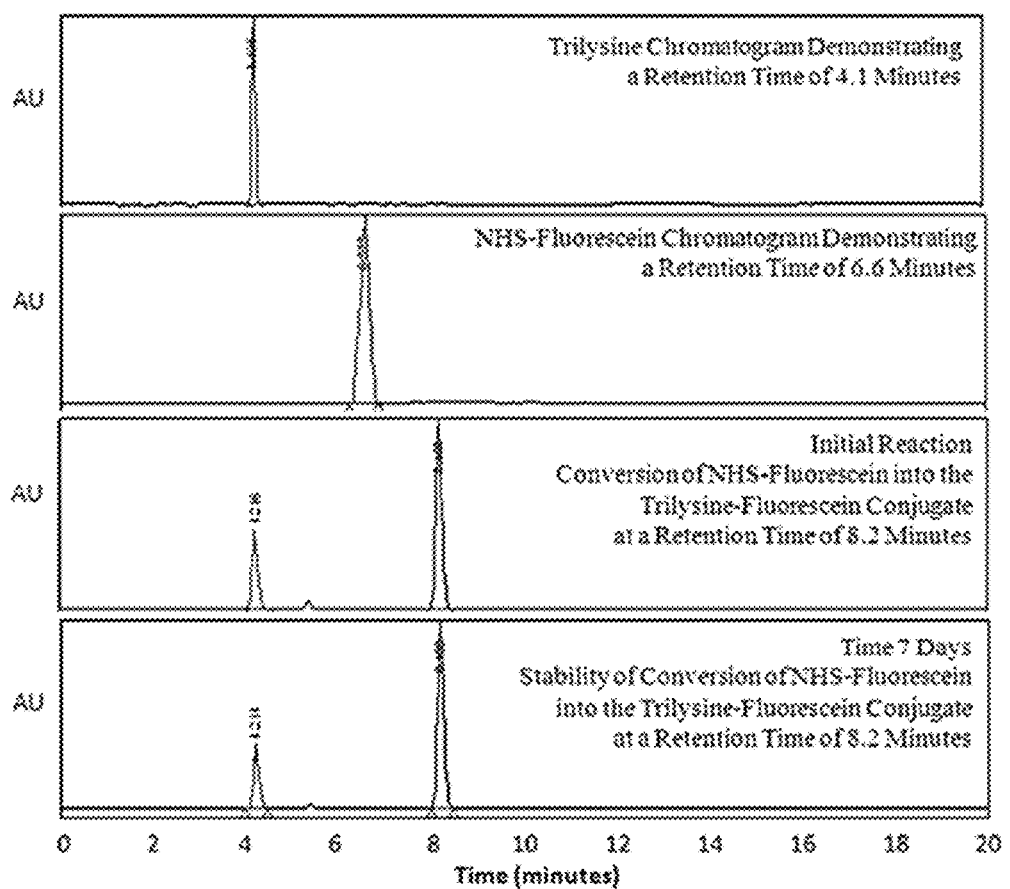
FIG. 2 depicts chromatograms illustrating the conversion of NHS-fluorescein into the fluorescein-trilysine conjugate.

The other syringe contained a trilysine-fluorescein conjugate solution buffered with sodium phosphate dibasic, prepared by (i) mixing 25.0 mg±0.5 mg NHS-fluorescein with 8,025.0 mg±5.0 mg of a solution comprising 97.5 mg-±2.5 mg trilysine acetate and 243.75 mg±2.5 mg (Formulations 1 and 3) or 690 mg±5.0 mg (Formulations 2A and 2B) sodium phosphate dibasic in 9,750.0±10.0 mg WFI, (ii) allowing the resulting mixture to react for 1 to 24 hours at room temperature, (iii) filtering the solution and (iv) filling syringes with portions of 1,575.0 mg±10.0 mg of the obtained solution per syringe. Completion of the reaction in step (ii) was confirmed by a reversed-phase (RP) HPLC method using UV detection which allows discriminating between the unreacted components and the product amide by retention time (RT). After step (ii), no quantifiable peak remained with a RT consistent with NHS-fluorescein (RT≈6.6 min) and a new peak created by the formation of the product amide emerged at a higher RT (RT~8.2 minutes). In an initial study, results demonstrated conversion to the amide after 1 hour and showed that the reaction product was stable at up to 7 days in solution (FIG. 2).

The two additional pre-cursor syringes were connected with a female-to-female luer lock connector, and their content was mixed together by passing back and forth between each syringe for a total of 25 times, to form the hydrogel suspension pre-cursor syringe. Tyloxapol, USP is added to the solution used to suspend the cyclosporine to aid in dispersing the cyclosporine and reducing any agglomeration as cyclosporine is highly insoluble in water and prone to agglomeration, as well as in preventing adhesion of the hydrogel mixture to the inner wall of the tubes which is believed to be a cause for flat-shaped inserts with low aspect ratio.

III. Preparation of Hydrogel Solution Pre-Cursor Syringe

The hydrogel solution pre-cursor syringe contained a buffered solution of PEG prepared by combining 1,565.0 mg±10.0 mg of a solution comprising 24.5 mg±1.0 mg sodium phosphate monobasic in 7,985.0 mg±50.0 mg WFI with 542.0 mg±5.0 mg of the 4a20K PEG-SG (a 20 kDa PEG with 4 arms with a N-hydroxysuccinimidyl glutarate end group, employed for Formulation 1) or of the 4a20K PEG-SAP (a 20 kDa PEG with 4 arms with a N-hydroxysuccinimidyl adipate end group, employed for Formulation 2A).

IV. Casting, Stretching and Drying

To form the hydrogel/cyclosporine suspension, the hydrogel suspension pre-cursor syringe comprising cyclosporine, tyloxapol and the trilysine-fluorescein conjugate, as well as the hydrogel solution pre-cursor syringe comprising the 4a20 k PEG-SG, the 4a20 k PEG-SAP or the 4a20 k PEG-SS were first degassed by placing into a vacuum chamber and exposing to a programed vacuum cycle and then connected with a female-to-female luer lock connector. The content of the pre-cursor syringes was mixed together by passing back and forth between each syringe for a total of 25 times, and the thus created suspension of hydrogel/cyclosporine was transferred into a single syringe.

The hydrogel/cyclosporine suspension syringe was then connected to the barb fitting on an autoclave-sterilized polyurethane tubing with 2.0 mm inner diameter and 2.8 mm outer diameter, cut to appropriate length, and the suspension was casted through the prepared tubing before the material cross-links and solidifies.

Once the tubing was full, the tubing was removed from the syringe and the barb fitting on the tube was capped. Gelling time was confirmed by performing a gel tap test. For the gel tap test, a small amount of remaining hydrogel/cyclosporine suspension was placed on a glass slide and tapped with a pipette tip until the suspension began to strand, indicating that polymerization has started (i.e., remains connected to the pipette tip during a complete tapping cycle) in approximately 2-8 minutes when the suspension gels.

The filled tube containing the hydrogel/cyclosporine suspension, in the following referred to as "casted strands", were placed vertically and stored in a curing chamber (ambient temperature and humidity) for 3 to 6 hours to allow the gel to cure.

Once the cure time has elapsed, the casted strands were placed in the stretching fixture and secured in place with dynamic clamps. The casted strands were stretched to the fixed length of the stretching fixture which was about 2.7 times the original tubing length. The stretching fixtures were then moved and placed vertically within an incubator set to 32.0±2.0° C. with a nitrogen flow rate of 53±3 SCFH (standard cubic feet per hour) for drying. The casted strands remained in the incubator for several days to allow them to dry completely.

V. Cutting, Packaging, Sterilization and Inspection

The dried casted strands were removed from the tubing and cut into approximately 2.7 mm lengths. A 100% in-process visual and dimensional inspection of inserts was performed using a Vision System under 10× magnification (acceptance criteria: particulate, cylindrical shape, free of visible surface defects, 0.55 mm+0.03 mm diameter for the cyclosporine-containing inserts, 0.41 mm±0.05 mm diameter for the HV-inserts, and 2.72 mm±0.08 mm length for all inserts).

Inserts that met all in-process specifications were packaged with a single insert in a foam carrier and sealed in an aluminum-LDPE foil pouch that can be peeled open by the user. To hold the insert, the foam carrier had a V-notch with an opening at the bottom, into which an insert was placed with forceps with a portion of the insert protruding for easy removal. The foam carrier with insert was placed into a foil pouch. The unsealed foil pouch was transferred into a glovebox providing an inert nitrogen environment to reduce residual moisture from the foam and pouch material, stored therein for a minimum duration of 16 hours and not to exceed 96 hours, and then sealed within the glovebox using a pouch sealer to create a complete, continuous seal on the pouch. The pouch seal was inspected and the packages stored at 2-8° C. until sterilization.

The packaged inserts were e-beam or gamma irradiation sterilized and stored at 2-8° C. until final quality inspection.

Once the pouched inserts were sterilized, a final quality inspection was performed on the drug product.

Example 2: Insert Specifications

The obtained inserts were characterized by way of a visibility test, microscopy analysis, HPLC analysis, as well as a storage stability test.

I. Visibility Test

The inserts were visually inspected in order to confirm that the inserts can be visually seen through a surrogate test model when illuminated with a blue light.

II. Microscopy Analysis

The inserts were inspected microscopically using a Unitron Z850/NSZ-606 microscope to confirm product dimensions in dry state, as well as in hydrated state after 10 minutes (Expansion state) and 24 hours (Equilibrium state) hydration in phosphate-buffered saline at a pH of 7.4 at 37° C. (Table 2.1).

TABLE 2.1

Results of microscopy analysis for the different formulations

| | | Batch analysis | | | |
|---|---|---|---|---|---|
| | Target specification | Form. 1 SG | Form. 2A SAP | Form. 2B SAP | Form. 3 SS |
| Dimensions | | | | | |
| Dried | | | | | |
| Diameter | ≤0.62 mm | Passes | Passes | Passes | Passes |
| Length | 2.5-2.90 mm | Passes | Passes | Passes | Passes |
| Hydrated (Expansion, 10 min.) | | | | | |
| Diameter | ≥1.00 mm | Passes | Passes | Passes | Passes |
| Length | To be reported | | | | |
| Hydrated (Equilibrium, 24 hours) | | | | | |
| Diameter | ≥1.30 mm | Passes | Passes | Passes | Passes |
| Length | To be reported | | | | |

III. Further Product Specification Tests

Further product specification has been tested and reported in accordance with Table 2.2 below.

TABLE 2.2

Results of further product specification tests

| | | Batch analysis | | | |
|---|---|---|---|---|---|
| Product specification test | Target specification | Form. 1 SG | Form. 2A SAP | Form. 2B SAP | Form. 3 SS |
| HPLC: | | | | | |
| Identity | RT ± 0.5 minutes* | Pass | Pass | N/A | N/A |
| Assay (%) | 85.0 to 115.0% | 96% | 101% | N/A | N/A |
| Assay (absolute) | 306-414 μg (target: 360 μg) | 346 μg | 362 μg | N/A | N/A |
| Impurities | As specified below** | Pass | Pass | N/A | N/A |
| Water content (Karl Fischer—USP <921>) | <1.0% | 0.37% | 0.58% | 0.30% | 0.49% |
| Subvisible Particulate Matter (Light Obscuration—USP <788>) | ≥10 μm: NMT 6000 particles/insert | 78 | 128 | 22 | 81 |
| | ≥25 μm: NMT 600 particles/insert | 4 | 10 | 2 | 44 |
| Visible Particulate matter (Visual—USP <790>) | Solutions of inserts essentially free of visible particulates | Pass | Pass | Pass | Pass |

TABLE 2.2-continued

Results of further product specification tests

| Product specification test | Target specification | Batch analysis | | | |
|---|---|---|---|---|---|
| | | Form. 1 SG | Form. 2A SAP | Form. 2B SAP | Form. 3 SS |
| Endotoxin (Kinetic Chromogenic LAL— USP <85>) | ≤0.5 EU/insert | Pass | Pass | Pass | Pass |
| Sterility USP <71> | No microbial growth | Pass | Pass | Pass | Pass |

*RT (retention time) of cyclosporine peak corresponds to reference standard ± 0.5 minutes
**Target specification for the impurities were as follows:
Isocyclosporine A, ≤1.0%
Cyclosporine C, ≤1.0%
Cyclosporine B, ≤1.0%
DihydrocyclosporineA/Geclosporine, ≤1.4%
Cyclosporine D, ≤1.0%
Any individual impurity: ≤1.0%
Total impurities: ≤6.0%

IV. Storage Stability Test

The stability of cyclosporine-containing inserts in accordance with formulations 1 and 2A has been evaluated over 12 months under refrigerated conditions (2-8° C.).

Results of the storage stability test can be found in Tables 2.3.1 and 2.3.2 (Formulation 1) as well as 2.3.3 and 2.3.4 (Formulation 2A).

TABLE 2.3.1

Results Storage Stability Test: Appearance, Dimensions, assay and identity (Formulation 1)

| Test Description | Acceptance Criteria | Time Point (Months) | | | | | | |
|---|---|---|---|---|---|---|---|---|
| | | 0 | 3 | 6 | 9 | 12 | 18 | 24 |
| Appearance | Light yellow to yellow/orange, essentially free of visible particulates | Pass | Pass | Pass | Pass | Pass | — | — |
| Dry Dimensions | Diameter: ≤0.62 mm | Diameter (mm) Avg: 0.55 Min: 0.53 Max: 0.57 | Diameter (mm) Avg: 0.56 Min: 0.52 Max: 0.59 | Diameter (mm) Avg: 0.54 Min: 0.49 Max: 0.58 | Diameter (mm) Avg: 0.55 Min: 0.50 Max: 0.57 | Diameter (mm) Avg: 0.54 Min: 0.51 Max: 0.57 | — | — |
| | Length: 2.50-2.90 mm | Length (mm) Avg: 2.68 Min: 2.57 Max: 2.76 | Length (mm) Avg: 2.68 Min: 2.62 Max: 2.76 | Length (mm) Avg: 2.70 Min: 2.64 Max: 2.75 | Length (mm) Avg: 2.72 Min: 2.67 Max: 2.76 | Length (mm) Avg: 2.66 Min: 2.62 Max: 2.69 | — | — |
| Expansion | Diameters: ≥1.00 mm | Diameter (mm) Avg: 1.29 Min: 1.21 Max: 1.36 | Diameter (mm) Avg: 1.27 Min: 1.20 Max: 1.36 | Diameter (mm) Avg: 1.26 Min: 1.19 Max: 1.35 | Diameter (mm) Avg: 1.26 Min: 1.21 Max: 1.33 | Diameter (mm) Avg: 1.23 Min: 1.17 Max: 1.30 | — | — |
| Equilibrium Diameter | Diameter: Report Results | Diameter (mm) Avg: 1.47 Min: 1.39 Max: 1.51 | Diameter (mm) Avg: 1.40 Min: 1.34 Max: 1.48 | Diameter (mm) Avg: 1.39 Min: 1.31 Max: 1.50 | Diameter (mm) Avg: 1.35 Min: 1.30 Max: 1.40 | Diameter (mm) Avg: 1.39 Min: 1.32 Max: 1.50 | — | — |
| | Length: Report Results | Length (mm) Avg: 2.48 Min: 2.35 Max: 2.63 | Length (mm) Avg: 2.56 Min: 2.42 Max: 2.63 | Length (mm) Avg: 2.56 Min: 2.47 Max: 2.62 | Length (mm) Avg: 2.61 Min: 2.53 Max: 2.66 | Length (mm) Avg: 2.57 Min: 2.48 Max: 2.65 | — | — |
| Visibility | Insert can be visually seen through a surrogate test model when illuminated with a blue light | Pass | Pass | Pass | Pass | Pass | — | — |
| Assay | Cyclosporine Content 360 ± 54 μg | 360 | 360 | 354 | 355 | 360 | — | — |

TABLE 2.3.1-continued

Results Storage Stability Test: Appearance, Dimensions, assay and identity (Formulation 1)

| Test Description | Acceptance Criteria | Time Point (Months) | | | | | | |
|---|---|---|---|---|---|---|---|---|
| | | 0 | 3 | 6 | 9 | 12 | 18 | 24 |
| Identity | Retention time of cyclosporine peak corresponds to reference standard ± 2 minutes | Pass | Pass | Pass | Pass | Pass | — | — |

TABLE 2.3.2

Results Storage Stability Test; impurities and further specifications (Formulation 1)

| Test Description | Acceptance Criteria | Time Point (Months) | | | | | | |
|---|---|---|---|---|---|---|---|---|
| | | 0 | 3 | 6 | 9 | 12 | 18 | 24 |
| Impurities | Total impurities: NMT 3.0% | 1.6% | 1.6% | 1.9% | 1.9% | 1.8% | — | — |
| | Isocyclosporine A (RRT 0.53): NMT 1.0% | 0.1% | 0.4% | 0.4% | 0.3% | 0.4% | — | — |
| | Cyclosporine C (RRT 0.87): NMT 1.0% | NR | NR | NR | NR | NR | — | — |
| | Cyclosporine B (RRT 0.90): NMT 1.0% | ND | NR | NR | 0.3% | 0.3% | — | — |
| | Dihydrocyclosporine A/Geclosporine (RRT 1.07): NMT 1.0% | 0.6% | 0.6% | 0.5% | 0.6% | 0.5% | — | — |
| | Cyclosporine D (RRT 1.11): NMT 1.0% | 0.3% | 0.2% | 0.3% | 0.3% | 0.3% | — | — |
| | Unknown (RRT 0.55): NMT 1.0% | 0.1% | ND | ND | ND | ND | — | — |
| | Unknown (RRT 0.67): NMT 1.0% | ND | 0.1% | 0.1% | 0.1% | ND | — | — |
| | Unknown (RRT 0.95) NMT 1.0% | 0.2% | ND | 0.3% | ND | ND | — | — |
| | Unknown D (RRT 1.31): NMT 1.0% | 0.3% | 0.3% | 0.3% | 0.3% | 0.3% | — | — |
| In Vitro Release | Report Results at 4 Hours and Days 1, 2, 3, 4, 7, 8, 9[1] | Day 1: 32% Day 2: 51% Day 3: 64% Day 4: 81% Day 7: 96% Day 8: 102% Day 10: 102% Day 11: 103% | Day 1: 25% Day 2: 43% Day 3: 55% Day 6: 84% Day 7: 92% Day 8: 95% | * | 4 Hours: 13% Day 1: 26% Day 2: 36% Day 3: 46% Day 4: 54% Day 7: 73% Day 8: 84% Day 9: 96% | 4 Hours: 10% Day 1: 22% Day 2: 32% Day 3: 42% Day 4: 49% Day 7: 58% Day 8: 66% Day 9: 70% | — | — |
| Water Content | NMT 1% | 0.41% | 0.34% | 0.37% | 0.40% | 0.46% | — | — |
| Endotoxin | ≤0.5 EU/insert | <0.1 EU/Insert | | | | | | |
| Sterility | No Microbial Growth | Conforms | | | | | | |
| Seal Strength | Foil pouch must have a minimum seal strength of 1.0 lbf | Pass | | | | | | |
| Whole Package Integrity | Foul pouch must withstand bubble emission while pressurized at 10 ± 2 inches H2O. | Pass | | | | | | |

[1] T = 0 and T = 3 data reported prior to specification finalization;
T = 3, 4 hour interval and 9 day samples not pulled
*no data available, samples inadvertently not tested at 6 mos.
NMT: No more than
NR: Not reportable
ND: None detected
TBD: to be determined
— Not yet tested

TABLE 2.3.3

Results Storage Stability Test: Appearance, Dimensions, assay and identity (Formulation 2A)

| Test Description | Acceptance Criteria | Time Point (Months) | | | | | | |
|---|---|---|---|---|---|---|---|---|
| | | 0 | 3 | 6 | 9 | 12 | 18 | 24 |
| Appearance | Light yellow to yellow/orange, essentially free of visible particulates | Pass | Pass | Pass | Pass | Pass | — | — |
| Dry Dimensions | Diameter: ≤0.62 mm | Diameter (mm) Avg: 0.54 Min: 0.51 Max: 0.57 | Diameter (mm) Avg: 0.56 Min: 0.53 Max: 0.58 | Diameter (mm) Avg: 0.54 Min: 0.49 Max: 0.56 | Diameter (mm) Avg; 0.55 Min: 0.53 Max: 0.57 | Diameter (mm) Avg 0.55 Min: 0.50 Max: 0.57 | — | — |

TABLE 2.3.3-continued

Results Storage Stability Test: Appearance, Dimensions, assay and identity (Formulation 2A)

| Test Description | Acceptance Criteria | Time Point (Months) | | | | | | |
|---|---|---|---|---|---|---|---|---|
| | | 0 | 3 | 6 | 9 | 12 | 18 | 24 |
| Expansion | Length: 2.50-2.90 | Length (mm) Avg: 2.70 Min: 2.66 Max: 2.74 | Length (mm) Avg: 2.68 Min: 2.61 Max: 275 | Length (mm) Avg: 2.71 Min: 2.65 Max: 2.79 | Length (mm) Avg: 2.68 Min: 2.63 Max: 2.73 | Length (mm) Avg 2.65 Min: 2.61 Max: 2.69 | — | — |
| | Diameter: ≥1.00 mm | Diameter (mm) Avg: 1.25 Min: 1.16 Max: 1.32 | Diameter (mm) Avg: 1.24 Min: 1.16 Max: 1.30 | Diameter (mm) Avg: 1.20 Min: 1.14 Max: 1.26 | Diameter (nun) Avg: 1.20 Min: 1.11 Max: 1.33 | Diameter (mm) Avg 1.17 Min: 1.12 Max: 1.22 | — | — |
| Equilibrium Diameter | Diameter: Report Results | Avg: 1.54 Min: 1.47 Max: 1.63 | Avg: 1.45 Min: 1.39 Max: 1.51 | Avg: 1.44 Min: 1.35 Max: 1.54 | Avg: 1.40 Min: 1.34 Max: 1.52 | Avg: 1.36 Min: 1.30 Max: 1.50 | | |
| | Length: Report Results | Length (mm) Avg: 2.48 Min: 2.31 Max: 2.61 | Length (mm) Avg: 2.53 Min: 2.37 Max: 2.67 | Length (mm) Avg: 2.58 Min: 2.35 Max: 2.70 | Length (mm) Avg: 2.62 Min: 2.55 Max: 2.69 | Length (mm) Avg: 2.58 Min: 2.50 Max: 2.68 | | |
| Visibility | Insert can be visually seen through a surrogate test model when illuminated with a blue light | Pass | Pass | Pass | Pass | Pass | — | — |
| Assay | Cyclosporine Content 360 ± 54 μg | 360 | 350 | 345 | 348 | 356 | — | — |

TABLE 2.3.4

Restults Storage Stability Test: impurities and further specifications (Formulation 2A)

| Test Description | Acceptance Criteria | Time Point (Months) | | | | | | |
|---|---|---|---|---|---|---|---|---|
| | | 0 | 3 | 6 | 9 | 12 | 18 | 24 |
| Identity | Retention time of cyclosporine peak corresponds to reference standard ± 2 minutes | Pass | Pass | Pass | Pass | Pass | — | — |
| Impurities | Total impurities: NMT 3.0% | 1.4% | 1.5% | 1.9% | 1.8% | 1.7% | — | — |
| | IsocyClosporine A (RRT 0.53): NMT 1.0% | 0.1% | 0.3% | 0.4% | 0.4% | 0.4% | — | — |
| | Cyclosporine C (RRT 0.87): NMT 1.0% | NR | NR | NR | NR | NR | — | — |
| | Cyclosporine B (RRT 0.90): NMT 1.0% | ND | ND | 0.1% | 0.2% | 0.2% | — | — |
| | Dihydrocyclosporine A/Geclosporine (RRT 1.07): NMT 1.0% | 0.6% | 0.6% | 0.5% | 0.6% | 0.5% | — | — |
| | Cyclosporine D (RRT 1.11): NMT 1.0% | 0.3% | 0.2% | 0.3% | 0.3% | 0.3% | — | — |
| | Unknown (RRT 0.55): NMT 1.0% | 0.1% | ND | ND | NR | ND | — | — |
| | Unknown (RRT 0.66): NMT 1.0% | ND | 0.1% | 0.1% | ND | ND | — | — |
| | Unknown (RRT 1.04) NMT 1.0% | ND | 0.1% | NR | ND | ND | — | — |
| | Unknown D (RRT 1.31): NMT 1.0% | 0.3% | 0.3% | 0.3% | 0.3% | 0.3% | — | — |
| In Vitro Release | Report Results at 4 Hours and Days 1, 2, 3, 4, 7, 8, 9[1] | Day 1: 37% Day 2: 61% Day 3: 74% Day 4: 88% Day 7: 97% Day 8: 98% Day 10: 95% Day 11: 98% | Day 1: 32% Day 2: 53% Day 3: 66% Day 6: 89% Day 7: 94% Day 8: 96% Day 9: 96% | * | 4 Hours: 16% Day 1: 33% Day 2: 47% Day 3: 59% Day 4: 69% Day 7: 80% Day 8: 89% Day 9: 93% | 4 Hours: 13% Day 1: 31% Day 2: 42% Day 3: 54% Day 4: 63% Day 7: 69% Day 8: 77% Day 9: 80% | — | — |
| Water Content | NMT 1% | 0.59% | 0.61% | 0.58% | 0.60% | 0.68% | — | — |
| Endotoxin | ≤0.5 EU/Insert | <0.1 EU/Insert | | | | | | |
| Slerility | No Microbial Growth | Conforms | | | | | | |
| Seal Strength | Foil pouch must have a minimum seal strength of 1.0 lbf | Pass | | | | | | |
| Whole Package Integrity | Foil pouch must withstand bubble emission while pressurized at 10 ± 2 inches TI2O | Pass | | | | | | |

[1]T = 0 and T = 3 data reported prior to specification finalization.
*no data available, samples inadvertently not tested at 6 mos.
NMT: No More than, NR: Not reportable, ND: None detected, TBD: to be determined,
— Not yet tested Stability data obtained through 12 months continue to meet the predetermined stability specifications. In accordance with the ICH Q1E, for refrigerated products, where the long-term data shows little or no change over time and shows little or no variability, the proposed shelf life can be up to two times but should not be more than 12 months when the proposal is backed by the result of the analysis and relevant supporting data. The real time long term stability data was trended against the upper and lower limits of the stability specifications with 95% Confidence Intervals (CI). Overall there were minimal to no trends observed in the quantitative data. The statistical analysis demonstrate that the product will meet a 23 month shelf life based on the degradation analysis of assay showing a possible intercept at 23 months. All other stability indicating parameters show possible intercepts beyond 36 months. Therefore, a shelf life of at least 23 months can be expected.

Example 3: Evaluation of Cyclosporine Inserts in Beagle Dogs

In order to study the pharmacokinetics of cyclosporine-containing inserts, different formulations have been tested in beagle dog pharmacokinetic studies.

Six different beagle dog studies were conducted, wherein the amount of drug released from the insert and/or the concentrations of cyclosporine in the tear fluid over the study durations has been determined. An overview of the studies and the formulations is given in Table 3.

TABLE 3

Overview of beagle studies

| Beagle Study | Study design |
| --- | --- |
| Example 3.1: Proof-of-Concept PK study | N = 4 Beagles<br>0.7 mg cyclosporine dose in 12.7% (w/v) 4a20K SAZ/trilysine PEG hydrogel<br>10-week bilateral dosing<br>Tear fluid sampling at weeks 2, 4, 6, 8 and 10<br>Subset of inserts removed at 6 weeks |
| Example 3.2: Proof-of-Concept PK study | N = 20 Beagles<br>0.44 mg cyclosporine dose in 9% (w/v) 4a20K SG/trilysine PEG hydrogel<br>28-day bilateral dosing<br>Tear fluid at days 1, 7, 14, 21 and 28<br>Removed inserts at day 32 |
| Example 3.3: Proof-of-Concept PK study | N = 11 Beagles<br>0.67 mg cyclosporine dose in 9% (w/v) 4a20K SG/trilysine PEG hydrogel<br>28 and 50-day dosing<br>Removed inserts at days 28 and 50 |
| Example 3.4: Dry eye model study | N = 12 Beagles<br>12 eyes per arm<br>0.36 mg cyclosporine dose in 9% (w/v) 4a20K SG/trilysine<br>Formulation I<br>28-day bilateral dosing<br>Group 1: Surgical dry eye is right eye (OD)<br>Group 2: Healthy eye is left eye (OS) |
| Example 3.5: PK study | N = 24 Beagles<br>12 per group<br>0.36 mg cyclosporine dose<br>Formulations 1 and 2A<br>12-week bilateral dosing<br>Group 1: Formulation I inserts (9% (w/v) 4a20K SG/trilysine)<br>Group 2: Formulation 2A inserts (9% (w/v) 4a20K SAP/trilysine) |
| Example 3.6: High dose study | N = 54 Beagles<br>12 M/12 F active, 12 M/12 F control, 3 M/3 F sham<br>90-Day Dosing<br>0.7 mg cyclosporine dose |
| | Formulation 4A inserts in OD eyes (9% (w/v) 4a20K SG/trilysine)<br>Formulation 4B inserts in OS eyes (9% (w/v) 4a20K SAP/trilysine) |

Example 3.1: Proof of Concept PK Study

Inserts with a nominal dose of 0.7 mg cyclosporine were administered to beagle dogs as summarized in Table 3.

The amount of drug released from the inserts was evaluated over time and the concentrations of cyclosporine in the tear fluid were determined over the study duration.

The median tear fluid concentrations of cyclosporine ranged from 1.1 to 1.9 sg/over the study duration, see Table 3.1 below. A subset of inserts was removed at 6 weeks to determine the amount of remaining drug compared to the administered dose. The average amount of cyclosporine released in 6 weeks was 0.37 mg. This calculates to an estimated daily delivered dose of 8.8 sg/day assuming consistent daily release rates over that dosing period as supported by the tear fluid concentration which remained relatively constant.

TABLE 3.1

Cyclosporine Tear Fluid Concentrations in Beagle Eyes

| Time | Median (µg/mL) | SD (µg/mL) |
| --- | --- | --- |
| 2 weeks | 1.5 | 0.7 |
| 4 weeks | 1.2 | 0.6 |
| 6 weeks | 1.4 | 0.9 |
| 8 weeks | 1.9 | 1.4 |
| 10 weeks | 1.1 | 0.5 |

Example 3.2: Proof of Concept PK Study

Inserts with a nominal dose of 0.44 mg cyclosporine were administered to beagle dogs as summarized in Table 3.

The amount of drug released from the inserts was evaluated over time and the concentrations of cyclosporine in the tear fluid were determined over the study duration.

The mean tear fluid concentrations of cyclosporine ranged from 1.1 to 2.8 µg over the study duration, see Table 3.2 below. Inserts were removed at 32 days to determine the amount of remaining drug compared to the administered dose. The average amount of cyclosporine released in 32 days was 0.2 mg. This calculates to an estimated daily delivered dose of 6.3 µg/day assuming consistent daily release rates over that dosing period.

TABLE 3.2

Cyclosporine Tear Fluid Concentrations in Beagle Eyes

| Time | Mean (µg/mL) | SD (µg/mL) |
| --- | --- | --- |
| 1 day | 2.7 | 1.8 |
| 7 days | 2.1 | 1.8 |
| 14 days | 2.8 | 1.5 |

TABLE 3.2-continued

Cyclosporine Tear Fluid Concentrations in Beagle Eyes

| Time | Mean (µg/mL) | SD (µg/mL) |
|---|---|---|
| 21 days | 1.7 | 1.4 |
| 28 days | 1.1 | 0.3 |

Example 3.3: Proof of Concept PK Study

The initial cyclosporine dose in the insert prior to administration was 671±13 µg (mean and standard deviation) for n=10 total samples. Four and five inserts were removed at 28 and 50 days, respectively, and the cyclosporine content was analyzed. Left and right eyes provided similar results, thus a mean over all removed inserts was calculated, resulting in a released amount (initial amount minus the amount left in the removed insert of 576±18 µg and 494±32 µg, respectively) of 3.4 and 3.5 µg, respectively, as shown in Table 3.3. The average daily release rate was determined by comparing the initial dose to the released dose. Study results demonstrate that over 28 and 50 days the daily estimated delivered dose was approximately 3.5 µg/day. The range of drug release for the inserts over the study period was from a low of 2.7 to a high of 4.4 µg/day.

3.3: Cyclosporine Released from Inserts in Beagles

| Day | Cyclosporine per insert OD | Cyclosporine per insert OS | Cyclosporine per insert Mean ± SD [µg] | Cyclosporine Released per Day Mean (Min, Max) [µg] |
|---|---|---|---|---|
| 28 | | 578 | 576 ± 18 | 3.4 (2.7, 4.2) |
|  | | 579 | | |
|  | 596 | | | |
|  | | 553 | | |
| 50 | 451 | | 494 ± 32 | 3.5 (3.0, 4.4) |
|  | | 507 | | |
|  | 520 | | | |
|  | | 471 | | |
|  | 521 | | | |

Example 3.4: Dry Eye Model Study

Inserts with a nominal dose of 0.36 mg cyclosporine and 1.5 mm hydrated diameter and 2.5 mm hydrated length were administered to beagle dogs as summarized in Table 3.

The lacrimal glands on the right eye were previously surgically removed in the beagles to create an artificial dry eye model. The left eye remained untreated and thus served as a healthy control. Tear production was followed over time by Schirmer's Tear Test and showed that tear production in the right eyes decreased to near zero, providing proof of concept for the dry eye model (see FIG. 3.1). The amount of drug released from the inserts was evaluated over time and the concentrations of cyclosporine in the tear fluid was determined over the study duration.

The mean tear fluid concentrations of cyclosporine ranged from 0.8 to 1.4 µg/mL in healthy eyes and ranged from 1.4 to 4.8 µg/mL in dry eyes, see Table 3.4 below. The higher tear fluid cyclosporine concentration in the beagle dry eye model (compared to the healthy eyes) demonstrates both that cyclosporine can be successfully transported into the tear fluid and most likely the ocular surface from the insert under dry eye-conditions and that concentrations of cyclosporine on the ocular surface may be higher under dry eye-conditions when compared to cyclosporine concentrations observed in healthy eyes due to reduced tear volume (as resulting from the reduced tear production) and thus lower drug dilution.

TABLE 3.4

Cyclosporine Tear Fluid Concentrations in Beagles in Dry and Healthy Eyes

| Eye | Time | N | Mean (µg/mL) | Min (µg/mL) | Median (µg/mL) | Max (µg/mL) | SD (µg/mL) | CV | 95% CI (µg/mL) |
|---|---|---|---|---|---|---|---|---|---|
| Dry Eye (OD) | 3 hours | 12 | 1.4 | 0.0 | 1.4 | 3.5 | 0.9 | 63% | 0.5 |
|  | 1 day | 12 | 3.3 | 0.3 | 1.8 | 19.9 | 5.3 | 163% | 3.0 |
|  | 7 days | 12 | 4.8 | 0.0 | 2.3 | 18.5 | 6.1 | 125% | 3.4 |
|  | 14 days | 10 | 2.8 | 0.3 | 1.3 | 12.3 | 3.8 | 135% | 2.3 |
|  | 28 days | 5 | 4.8 | 0.8 | 5.4 | 8.5 | 3.1 | 65% | 2.7 |
| Healthy Eye (OS) | 3 hours | 12 | 1.4 | 0.5 | 1.0 | 3.1 | 0.8 | 61% | 0.5 |
|  | 1 day | 12 | 1.1 | 0.5 | 1.0 | 2.2 | 0.5 | 49% | 0.3 |
|  | 7 days | 11 | 0.8 | 0.3 | 0.6 | 2.8 | 0.7 | 85% | 0.4 |
|  | 14 days | 11 | 0.9 | 0.4 | 0.7 | 2.5 | 0.7 | 72% | 0.4 |
|  | 28 days | 7 | 1.1 | 0.4 | 0.6 | 3.3 | 1.0 | 92% | 0.8 |

Example 3.5: Pharmacokinetic Study

Inserts of formulations 1 and 2A (PEG-SG and PEG-SAP hydrogels, 0.36 mg cyclosporine) were administered bilaterally in 24 beagle dogs, as summarized in Table 3. Tear fluid samples were taken post-dose at 1, 3, and 6 hours, days 1 and 3, weeks 1, 2, 4, 6, 8, 10 and 12. Results are shown in Table 3.5 as well as in FIGS. 3.2A and 3.2B below. Cyclosporine was released from the inserts into the tear fluid of the beagles over 12 weeks for both Formulation 1 (Group 1) as well as Formulation 2A (Group 2). The results demonstrate a comparable maximum of tear fluid concentration of 2.7 µg/mL occurring at about 3 hours between the two formulations. The drug release profile and tear fluid concentrations appear comparable (within the 95% confidence interval) between the two formulations over the first six weeks.

A potential reduction in cyclosporine tear fluid concentrations in beagles is noted in the SG hydrogel relative to the SAP hydrogel formulation between weeks 8 to 12. This difference could be due to the faster degradation of the SG hydrogel compared to the SAP hydrogel.

3.5 Cyclosporine Tear Fluid Concentrations in Beagles

|  | Mean ± 95% CI (μg/mL) | |
| --- | --- | --- |
| Time | Formulation 1 inserts | Formulation 2 inserts |
| 1 hour | 1.4 ± 0.4 | 2.4 ± 1.1 |
| 3 hours | 2.7 ± 0.5 | 2.7 ± 0.9 |
| 6 hours | 2.1 ± 1.0 | 2.5 ± 1.0 |
| 1 day | 1.5 ± 0.4 | 1.1 ± 0.2 |
| 3 days | 1.2 ± 0.3 | 1.3 ± 0.4 |
| 1 week | 1.1 ± 0.3 | 1.8 ± 0.9 |
| 2 weeks | 1.1 ± 0.4 | 1.6 ± 0.5 |
| 4 weeks | 1.0 ± 0.2 | 2.4 ± 1.4 |
| 6 weeks | 1.3 ± 0.7 | 0.9 ± 0.3 |
| 8 weeks | 0.4 ± 0.2 | 1.0 ± 0.5 |
| 10 weeks | 0.3 ± 0.1 | 0.8 ± 0.5 |
| 12 weeks | 0.5 ± 0.4 | 1.3 ± 0.5 |

Example 3.6: High Dose Study

Inserts with an elevated dose (0.7 mg cyclosporine) in accordance with the two hydrogel formulations 4A and 4B (PEG-SG and PEG-SAP) were assessed for pharmacokinetics in a GLP compliant toxicology study, as summarized in Table 3.

Tear fluid samples were taken pre-dose and post-dose at 1 h, 2 h, 4 h, 24 h and days 7, 30, 60, 90 and 104 days. Cyclosporine concentrations in tear fluid are shown in Table 3.6.1 as well as FIG. 3.3. Results demonstrate comparable (within 95% confidence intervals) tear fluid concentrations in this beagle study between the two formulations over the study duration and drug levels are below the lower limit of quantitation (LLOQ=30 ng/mL) in the recovery animals (test articles were removed two weeks prior to sampling at 104 days).

The pharmacokinetic profile is comparable between the two formulations and demonstrates a continual steady state dose exposure over the study duration. No true maximum concentration is evident as the tear fluid concentrations reach an apparent steady state within one hour of dose exposure over the study duration during the dosing period.

3.6.1 Cyclosporine Tear Fluid Concentrations in Beagles

|  | Mean ± 95% CI (μg/mL) | |
| --- | --- | --- |
| Time | Formulation 4A inserts | Formulation 4B inserts |
| Pre-dose | Not detected | Not detected |
| 1 hour | 2.9 ± 1.2 | 3.1 ± 1.7 |
| 2 hours | 3.1 ± 1.0 | 2.9 ± 0.9 |
| 4 hours | 2.7 ± 0.7 | 2.7 ± 1.0 |
| 1 day | 3.5 ± 1.0 | 3.4 ± 1.4 |
| 7 days | 2.4 ± 0.7 | 7.2 ± 0.7 |
| 30 days | 3.1 ± 0.9 | 3.1 ± 0.6 |
| 60 days | 2.3 ± 0.8 | 2.3 ± 0.8 |
| 90 days | 3.3 ± 1.1 | 4.1 ± 1.1 |
| 104 days | <LLOQ | <LLOQ |

Example 4: Randomized, Multi-Center, Double-Masked, Vehicle-Controlled, Human Phase 1/2 Clinical Study A randomized, multi-center, double-masked, vehicle-controlled, phase 1/2 clinical study was designed to evaluate the safety, tolerability, and efficacy of the cyclosporine inserts for intracanalicular use for the treatment of subjects with DED, comprising 145 subjects (290 eyes) enrolled in two cohorts, i.e. Cohort 1, an open-label group consisting of approximately 5 subjects (10 eyes) treated with formulation 2A hydrogel/cyclosporine inserts, and Cohort 2, a randomized, double-masked group consisting of approximately 140 subjects, treated with the 2 different formulations 1 and 2A hydrogel/cyclosporine inserts as well as the 2 different formulations 2B and 3 HV inserts.

Both eyes are treated with the same treatment/formulation. If both eyes qualify in terms of dry eye symptoms, the eye having the higher total corneal fluorescein staining score is designated as the study eye and the other eye designated as the non-study eye. If both eyes have the same total corneal fluorescein staining score, the study eye is determined by the biostatistician prior to the analysis. If only one eye qualifies, that eye will be the study eye, but both eyes will still receive the same treatment/formulation.

The treatment is summarized in Table 4 below.

TABLE 4

Treatment summary (HV = Hydrogel Vehicle)

| Cohort Number | Number of Subjects | Treatment | Formulation Number |
| --- | --- | --- | --- |
| 1 Open-label | 5 | Hydrogel/Cyclosporine | 2A |
| 2 Randomized, double-masked | 40 | Hydrogel/Cyclosporine | 1 |
|  | 40 | Hydrogel/Cyclosporine | 2A |
|  | 40 | HV (Placebo) | 2B |
|  | 20 | HV (Placebo) | 3 |

I. Study Schedule

Both Cohort groups follow essentially the same study schedule. Subjects were eligible in case of:
- a self-reported history or clinically confirmed diagnosis of dry eye disease by an eye care professional in both eyes for ≥6 months,
- ongoing dry eye disease in the study eye at screening visit as defined by a visual analogue scale (VAS) eye dryness severity score of ≥30, and
- a total Corneal Fluorescein Staining (tCFS) score of ≥6 and ≤15 (NEI scale, see Assessments section below) and a Schirmer's score (unanesthetized) of >0 mm and ≤10 mm wetting at 5 minutes, in the same qualifying eye or in both eyes, wherein Further inclusion and exclusion criteria apply.

The subjects undergo Screening 14 days prior to Insertion/Day 1 (Visit 2) and eligibility is confirmed at Visit 2 (Insertion/Day 1). Subjects in Cohort 2 are randomly assigned to one of the four treatment arms in a 2:2:2:1 ratio at Visit 2. Further treatment follow-up visits (Visits 3 to 8) are scheduled from Week 2 to Week 16 in regular intervals for all subjects in order to inter alia determine insert presence, wherein the presence of the inserts is assessed in a non-invasive manner by irradiating corresponding regions with a blue light and using a yellow filter.

For both cohorts, if the insert is visualized at Week 16 (Visit 8) the subject returns to the clinic in 30 days (t 10 days; Visit 9) and continues returning to the clinic every 30 days as needed until the insert can no longer be visualized and the physician has determined that there is no evidence of biological activity. If the insert cannot be visualized at Week 16 (Visit 8) and the physician has determined that there is no evidence of biological activity, the subject exits the study.

Figure 4A:
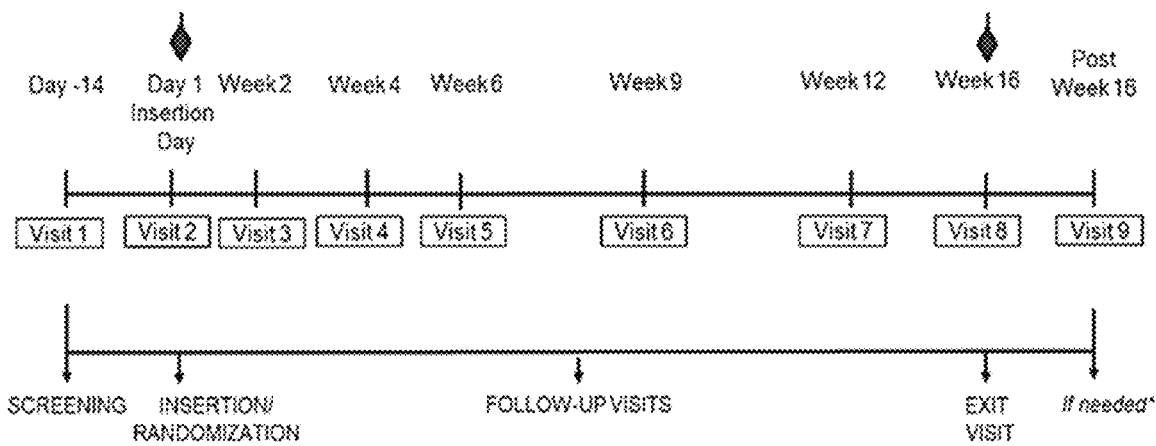
FIG. 4A depicts a general schematic of the human clinical study outline of Example 4.
Figure 4B:
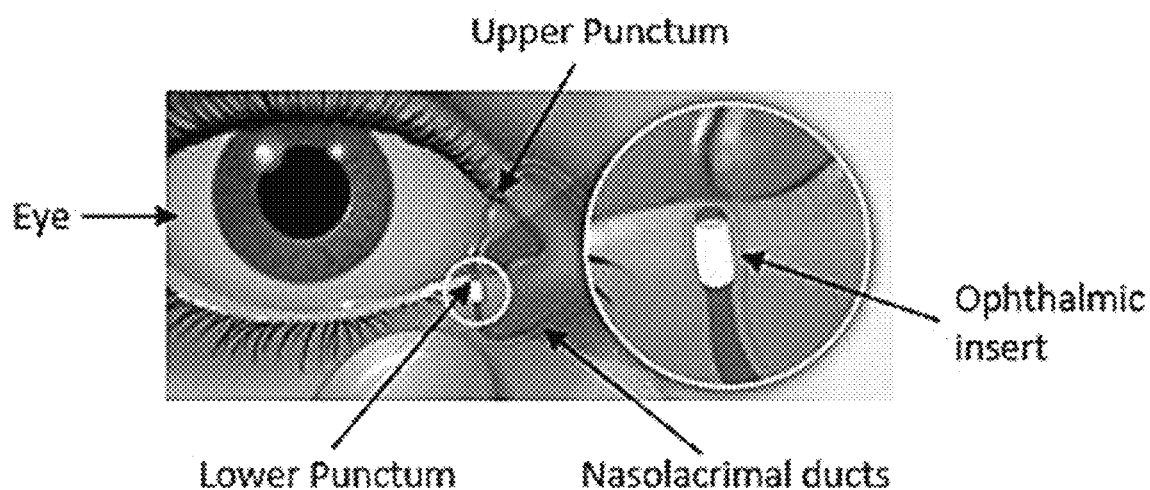
FIG. 4B depicts an exemplary general schematic of the insert placement within the canaliculus of a human eye.

A general schematic of the study is represented in FIG. 4A.

Various assessments are conducted at each Visit. In particular, all ophthalmic assessments outlined under point III below are conducted at all Visits 1 to 8 as well as Visit 9 (in case Visit 9 takes place for the individual patient), except the TBUT assessment (which takes place only at Visits 1, 2, 5 and 7).

The occurrence of any adverse event is likewise assessed at each visit from insertion day/day 1 onward (any signs, symptoms and conditions occurring prior to insertion on Day 1 being captured as medical history) in accordance with point III below.

II. Insert Placement

Figure 5A:
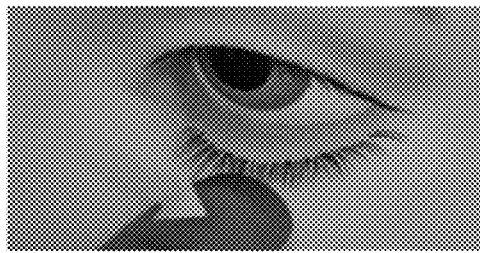
FIGS. 5A to 5D depict an exemplary schematic of the steps needed for insert placement within the canaliculus of a human eye.
Figure 5B:
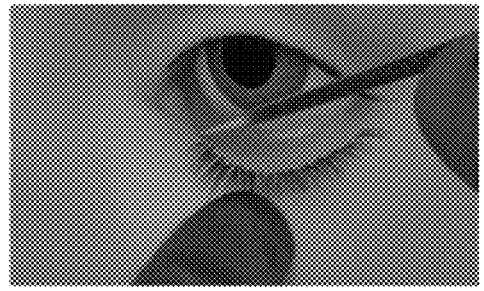

The ophthalmic inserts are placed in the vertical part of the canaliculus (see FIG. 5B). In the clinical studies disclosed herein, the inserts were placed in the lower punctum.

To place the inserts in the canaliculus, lateral pressure was applied to elongate the canalicular system, and the skin was pulled down temporally near the punctum (FIG. 5A). The lower punctum was dilated using a punctal dilator in towards the nose, ensuring the system was elongated, and the canaliculus was dilated deeper through the punctum for depth, as well as width, rotating the dilator in a spinning motion to help with the dilating process, if necessary (FIG. 5B).

Figure 5C:
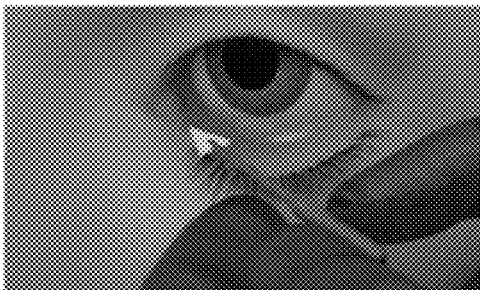

The surface around the punctal opening was dried using an ophthalmic sponge (FIG. 5C).

Figure 5D:
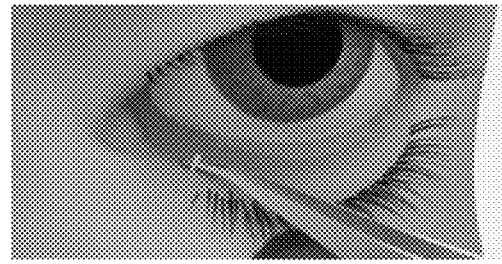

The hydrogel/cyclosporine or HV inserts were inserted with forceps at a slight angle towards the nose (FIG. 5D), aiming for 70% of insertion within the first motion, and using the forceps to tap or push insert the remainder of the way in, avoiding excessive squeezing of the insert to prevent deformation. The insert was confirmed to be localized slightly beneath the punctal opening.

In case the insert hydrated before placement slightly below the punctal opening (resembling a trumpet shape), or hydrated before ideal positioning or in case a portion of the insert was protruding and unable to be inserted, the insert was discarded and a new insert was used.

The level of ease of insertion of the ophthalmic insert was graded as "easy" (1), "moderate" (2) or "difficult" (3).

III. Assessments

The study employed the following assessments:

Schirmer's Tear Test

The Schirmer's test determines the amount of tears produced and works by capillary action, which allows the tear liquid to travel along the length of the paper test strip. The rate of travel along the test strip is proportional to the rate of tear production. The subject is asked to look up and the bent end of the test strip is applied such that it rests between the inferior palpebral conjunctiva of the lower eyelid and the bulbar conjunctiva of the eye. After five minutes, the patient is asked to open both eyes and look upward and the test strips are removed. The Schirmer's test score is determined by the length of the moistened area of the strips. Both eyes are tested at the same time. When anesthetized, only basal tear secretion is being measured.

A Schirmer's score of ≥10 mm wetting is considered normal, while a score of <5 mm indicates tear deficiency.

Tear Film Break Up Time (TBUT) and Total Corneal Fluorescein Staining (tCFS)

The time required for the tear film to break up following a blink is called TBUT. It is a quantitative test for measurement of tear film stability. The normal time for tear film breakup is over 15 seconds. To assess TBUT, a fluorescein strip is moistened with saline and applied to the inferior cul-de-sac. After a couple of blinks, the tear film is examined using a broad-beam of slit lamp with a blue filter for the appearance of the first dry spots on the cornea.

TBUT values of less than 5-10 seconds indicate tear instability and are observed in patients with mild to moderate dry eye disease.

The total Corneal Fluorescein Staining (tCFS) value is measured to assess the condition of the cornea Damages such as abrasions on the corneal surface, which may result e.g. from dry eyes, are made visible by a fluorescein dye staining.

To assess tCFS, a fluorescein strip is wetted with saline solution/eye wash, the subject is asked to look up and the moistened strip is applied to the inferior palpebral conjunctiva without touching the strip to the bulbar conjunctiva Since TBUT is also assessed by applying fluorescein, if the tCFS measurement is done closely following the TBUT, then an additional application of fluorescein dye is not required. The subject is asked to blink several times to distribute the fluorescein dye, and after 2 to 3 minutes wait time, the cobalt blue illumination and the Wratten yellow filter is used to assess the corneal staining for each of the 5 regions of the cornea, central, inferior, nasal, temporal, and superior using the NEI (National Eye Institute) 0-3 scoring scale (0=No Staining, 1=Mild Staining, 2=Moderate Staining, 3=Severe Staining), wherein the CFS total score is the sum of the five areas (0 to 15).

The higher the tCFS score, the higher the damages on the corneal surface.

Conjunctival Lissamine Green Staining (LGS)

The LGS value is measured to assess the condition of the conjunctiva. A Lissamine strip is wetted with saline solution/eye wash, the subject is asked to look up and the moistened strip is applied to the inferior palpebral conjunctiva without touching the strip to the bulbar conjunctiva. The subject is asked to blink several times to distribute the lissamine dye, and after 1 to 4 minutes wait time, the moderate illumination is used to assess the conjunctival staining for each of the 6 regions of the conjunctiva, temporal, superior temporal, inferior temporal as well as superior nasal, inferior nasal, and nasal using the NEI 0-3 scoring scale, wherein the LGS total score is the sum of the six areas (0 to 18).

The staining produced by an elevated pinguecula may not improve. The staining associated with the pinguecula may be consistently excluded from the total Lissamine score.

The higher the LGS score, the higher the damages on the conjunctival surface.

Best Corrected Visual Acuity BCVA

Visual acuity testing should precede any examination requiring contact with the eye or instillation of study dyes. Log MAR visual acuity must be assessed using an Early Treatment Diabetic Retinopathy Study (ETDRS) or modified ETDRS chart, consisting of lines of five letters each, each line representing a 0.1 log unit of the minimum angle of resolution (log MAR) at a given test distance.

Visual acuity testing is performed using an Early Treatment Diabetic Retinopathy Study (ETDRS) or modified ETDRS chart with best correction using subject's own corrective lenses (spectacles only) or pinhole refraction. The ETDRS or modified ETDRS chart consists of lines of five letters each, each line representing a 0.1 log unit of the minimum angle of resolution (log MAR) at a given test distance.

Visual acuity (VA) is scored as a log MAR value, wherein the last line in which a letter is read correctly will be taken as the base log MAR reading, to which N×0.02 is added, with N being the total number of letters missed up to and included in the last line read. This total sum (base log MAR+N×0.02) represents the BCVA for that eye.

The lower the BCVA score, the better the visual acuity.
Eye Dryness Score/Visual Analogue Scale VAS In order to assess the eye dryness score the subject is asked to rate the severity and the frequency of symptom of eye dryness in percent by placing a vertical mark on a horizontal line (representing values from 0 to 100%) to indicate the level of eye discomfort that they are experiencing in both eyes currently and how often the eye dryness is experienced, wherein 0% corresponds to "no discomfort" and 100% corresponds to "maximal (the most) discomfort".
Ocular Surface Disease Index OSDI©

The OSDI allows to quickly assess the symptoms of ocular irritation in dry eye disease based on a 12-item questionnaire assessing dry eye symptoms and the effects it has on vision-related function in the past week of the subject's life (see e.g. by R. M. Schiffman et al. in *Arch Ophthalmol.* 2000; 118(5):615-621 hereby incorporated by reference).

The higher the final score, the greater the disability.
Standard Patient Evaluation of Eye Dryness (SPEED) Evaluation The SPEED questionnaire (see Korb and Blackie, *Ocular Surgery News* Europe Edition, 2012 hereby incorporated by reference) is another assessment for monitoring dry eye symptoms over time, with a score from 0 to 28 resulting from 8 items that assess frequency and severity of symptoms including dryness, grittiness, scratchiness, irritation, burning, watering, soreness, and eye fatigue.

Higher scores indicate greater disability.

IV. Adverse Events

An adverse event (AE) is any untoward medical occurrence in a patient or clinical investigation subject administered a pharmaceutical product and that does not necessarily have a causal relationship with this treatment. An AE can therefore be any unfavorable and unintended sign (including an abnormal laboratory finding), symptom, or disease temporally associated with the use of a medicinal (investigational) product, whether or not related to the medicinal (investigational) product.

A serious adverse event (SAE) is any untoward medical occurrence that at any dose:
Results in death
Is life-threatening (referring to an event in which the subject was at risk of death at the time of the event, but not an event which hypothetically might have caused death if it were more severe)
Requires in-patient hospitalization or prolongation of existing hospitalization. (hospitalizations for elective surgeries do not constitute an SAE)
Results in persistent or significant disability/incapacity.
Is a congenital abnormality/birth defect.

During each visit, the subjects are questioned about adverse events using an open question taking care not to influence the subject's answers.

Any AE as well as SAE experienced by the subject from Visit 2 (Insertion/Day 1) through Visit 9 (30-day follow-up visit) is recorded regardless of the severity of the event or its relationship to study treatment.

Any AEs already documented at a previous assessment and designated as ongoing, is reviewed at subsequent visits as necessary, and if these have resolved, this is documented.

Changes in intensity or frequency of AEs are recorded as separate events (i.e., a new record is started).

Any SAE ongoing when the subject completed the study or discontinued from the study is followed until the event has resolved, stabilized, or returned to baseline status.

All events are assessed to determine whether the event meets the criteria for an SAE, the severity of the event as well as the relationship of the event to study treatment.

Example 4.1: Cohort 1—Open Label, Single-Center Phase 1 Study

Cohort 1 was an open-label phase 1 study intended to evaluate safety, tolerability, durability and biological activity of the hydrogel/cyclosporine insert, and treatment assignment was known to the sponsor, investigator and subjects and the study schedule as outlined above under 1. Study Schedule was followed. All 5 enrolled subjects (10 eyes) in Cohort 1 received Formulation 2A inserts at Visit 2 in accordance with the procedure as outlined above under II. Insert placement after eligibility was confirmed.

I. Safety and Tolerability

All subjects completed the 16-week study period with no drop-outs. No serious adverse effects were reported. The inserts were observed to be well-tolerated, and there were no adverse events of stinging, irritation, blurred vision or tearing reported or observed. No replacement inserts were required. The level of ease of insertion of the insert was rated as follows:
8 eyes: Easy
1 eye: Moderate
1 eye: Difficult The moderate and difficult rating was for the same subject's right and left eye. This shows that the overall insert dimensions and swelling behavior were excellently adjusted for an easy administration of the insert.

II. Durability

All inserts were last visualized at Visit 8.

III. Biological Activity/Efficacy

Efficacy of the insert treatment was evaluated based on the ophthalmic assessments conducted at each visit.

Figure 6A:
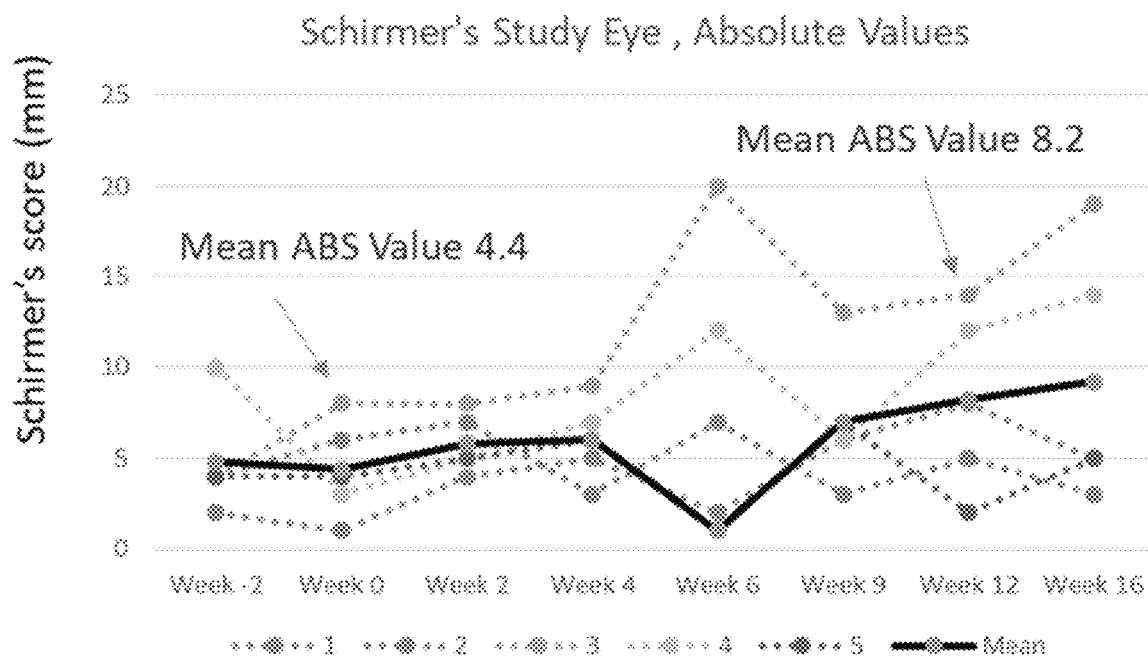
FIGS. 6A and 6B depict the results of tear production as followed over time by a Schirmer's Tear Test of Example 4.1 for the study (FIG. 6A) and the non-study eye (FIG. 6B). The solid black line represents the mean Schirmer's score for all individuals analyzed, wherein the dashed lines represent the Schirmer's score for the single individuals.
Figure 6B:
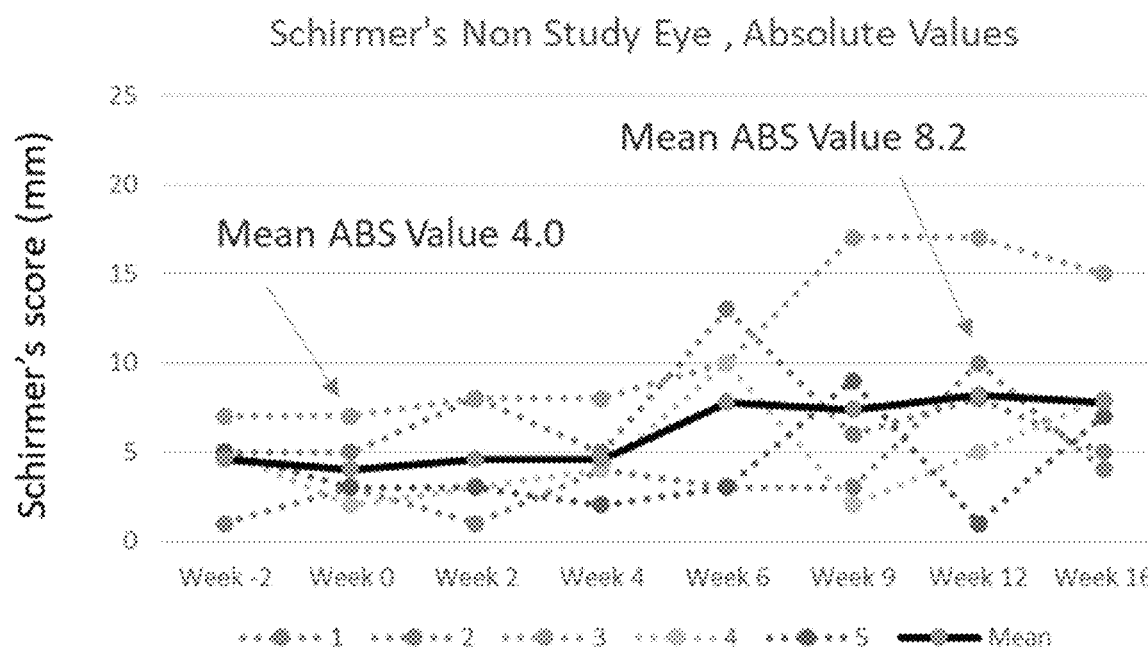

Tear production as measured by the Schirmer's test (unanesthetized) improved from a mean value of 4.2 mm at baseline to 8.2 mm at Week 12, wherein one of five (20%) subjects had a ≥10 mm increase in Schirmer's score at Week 12 from baseline (see FIGS. 6A and 6B).

Figure 7A:
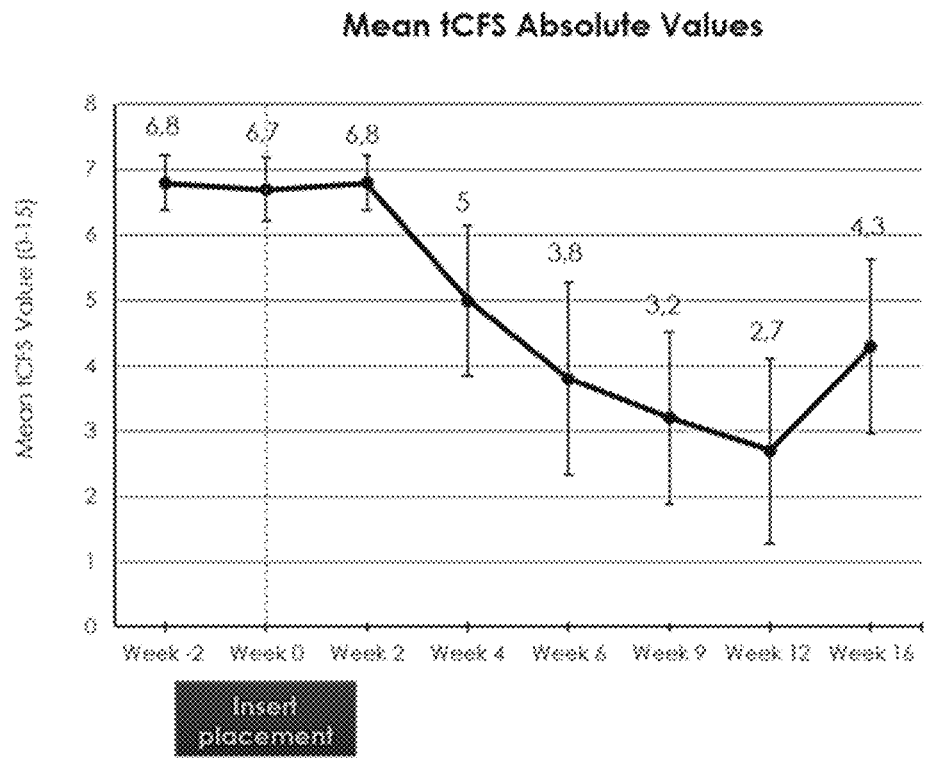
FIGS. 7A and 7B depict the total Corneal Fluorescein Staining (tCFS) values (mean values over all eyes) in terms of absolute values as well as in terms of change from baseline followed over time of Example 4.1.
Figure 7B:
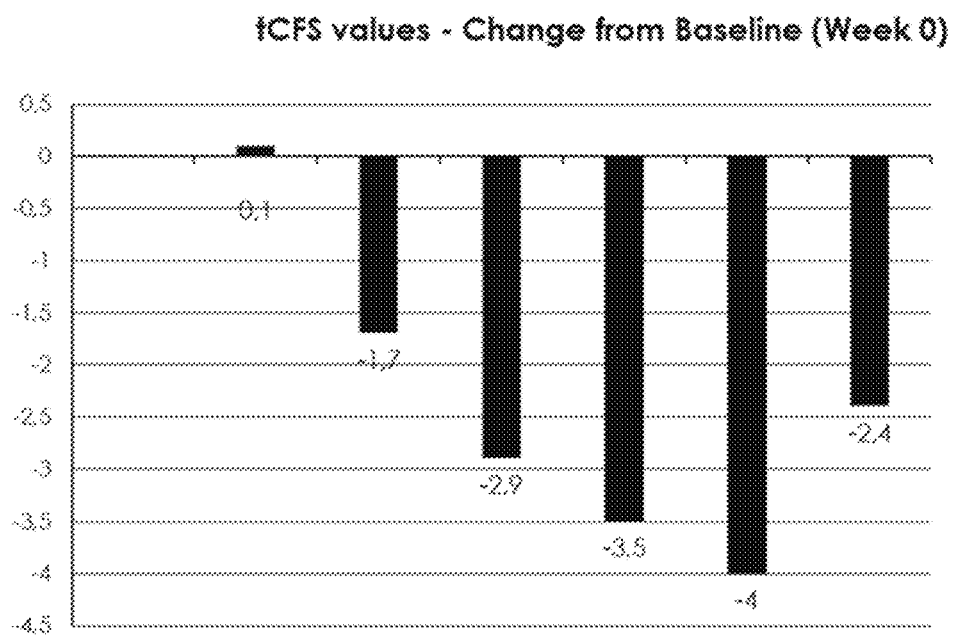

The subjects demonstrated an improvement in signs of Dry Eye Disease (DED) as measured by tCFS. The tCFS improved from a mean value of 6.7 at baseline to a mean value of 2.7 at Week 12 (see FIG. 7A), resulting in a Change from Baseline (CFB) of −4.0 at Week 12 (see FIG. 7B).

Figure 8A:
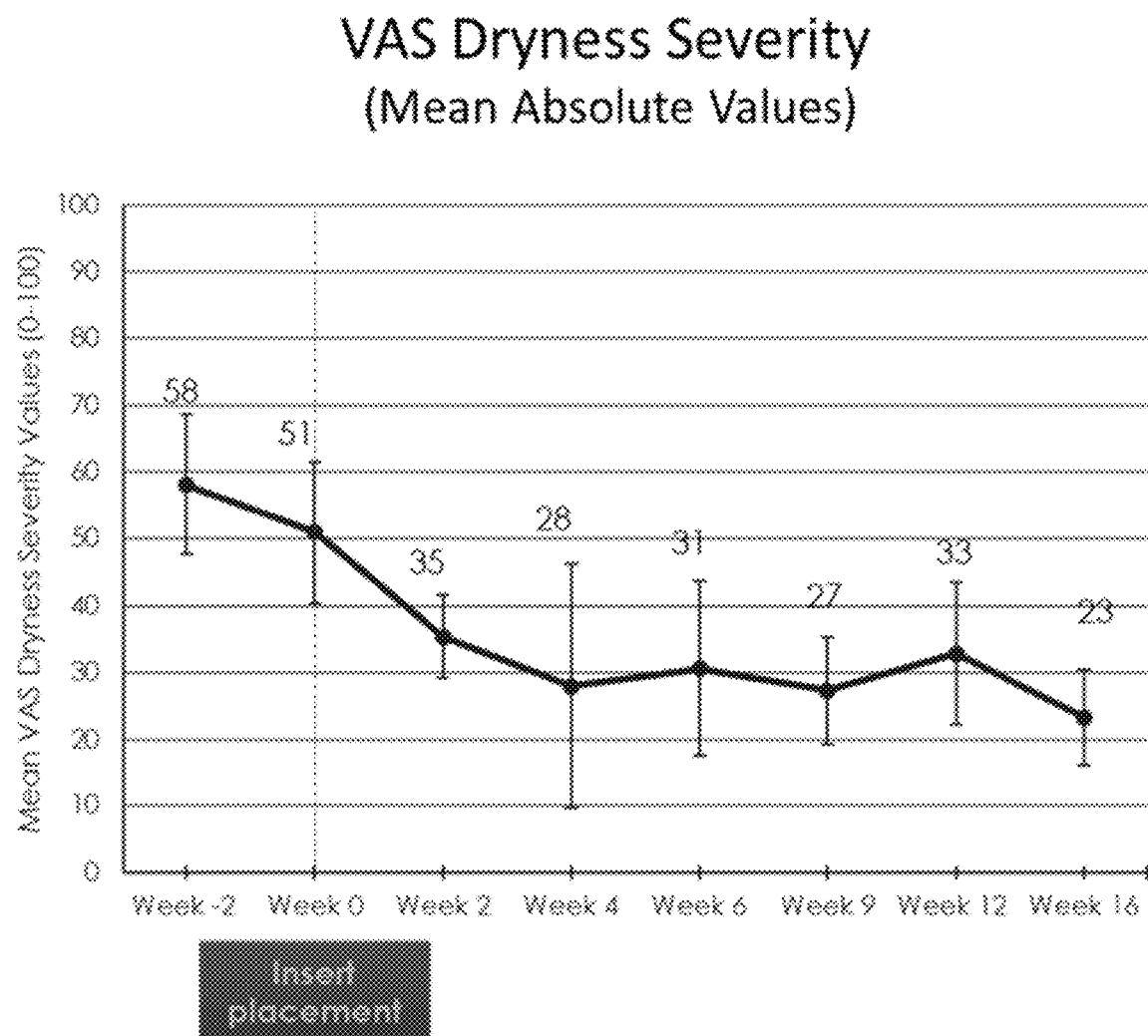
FIGS. 8A and 8B depict the results of eye dryness severity score on a visual analogue scale (VAS) in terms of absolute values as well as in terms of change from baseline followed over time of Example 4.1.
Figure 8B:
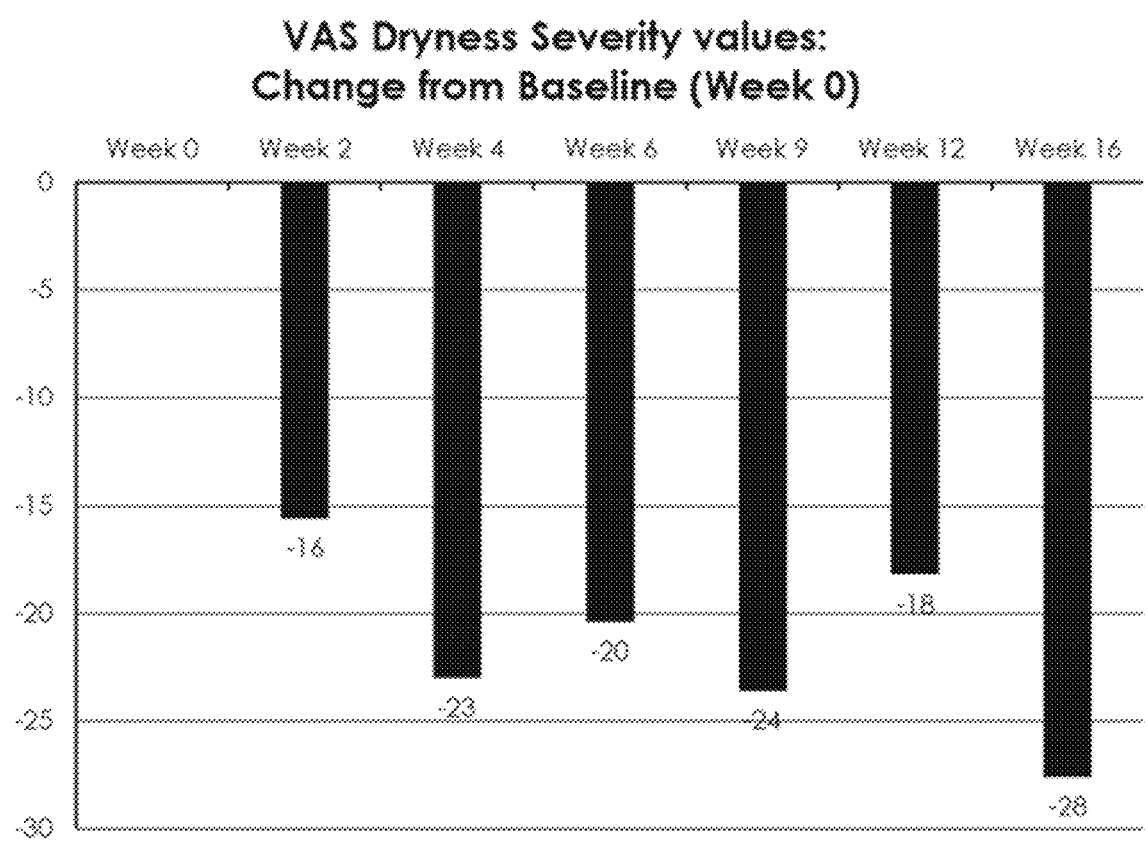
Figure 9:
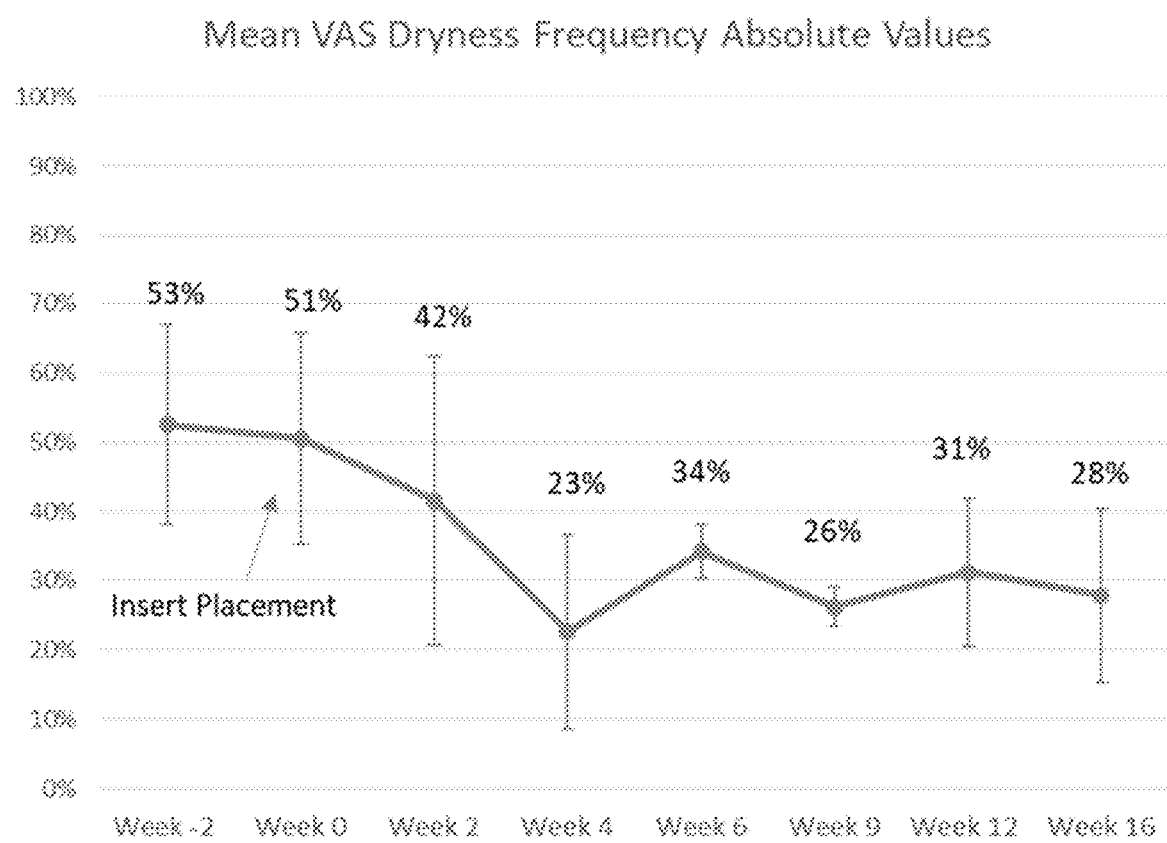
FIG. 9 depicts the results of eye dryness frequency score on a visual analogue scale (VAS) in terms of absolute values followed over time of Example 4.1.

The symptoms of DED also improved, as measured by
(i) the visual analog scale (VAS) eye dryness severity score, which improved from a mean value of 51 at baseline to a mean value of 33 at Week 12 (see FIGS. 8A and 8B), and (ii) the VAS dry eye frequency score, which improved from a mean value of 51 at baseline, to a mean value of 31 at Week 12 (see FIG. 9).

The onset of action of the inserts was seen as early as two weeks for both signs and symptoms of DED (as measured by the VAS eye dryness severity and frequency score), and continued over the 16 week study period.

Figure 10:
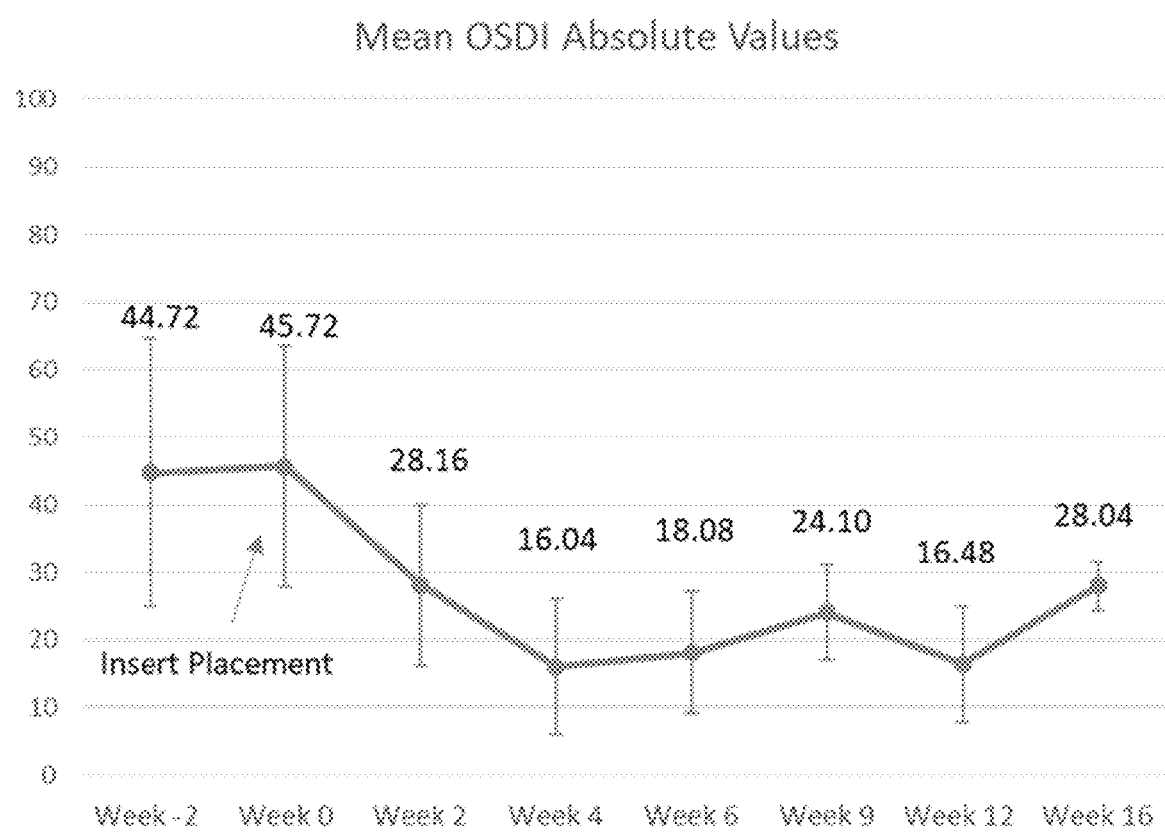
FIG. 10 depicts the results of OSDI in terms of mean absolute values followed over time of Example 4.1.
Figure 11:
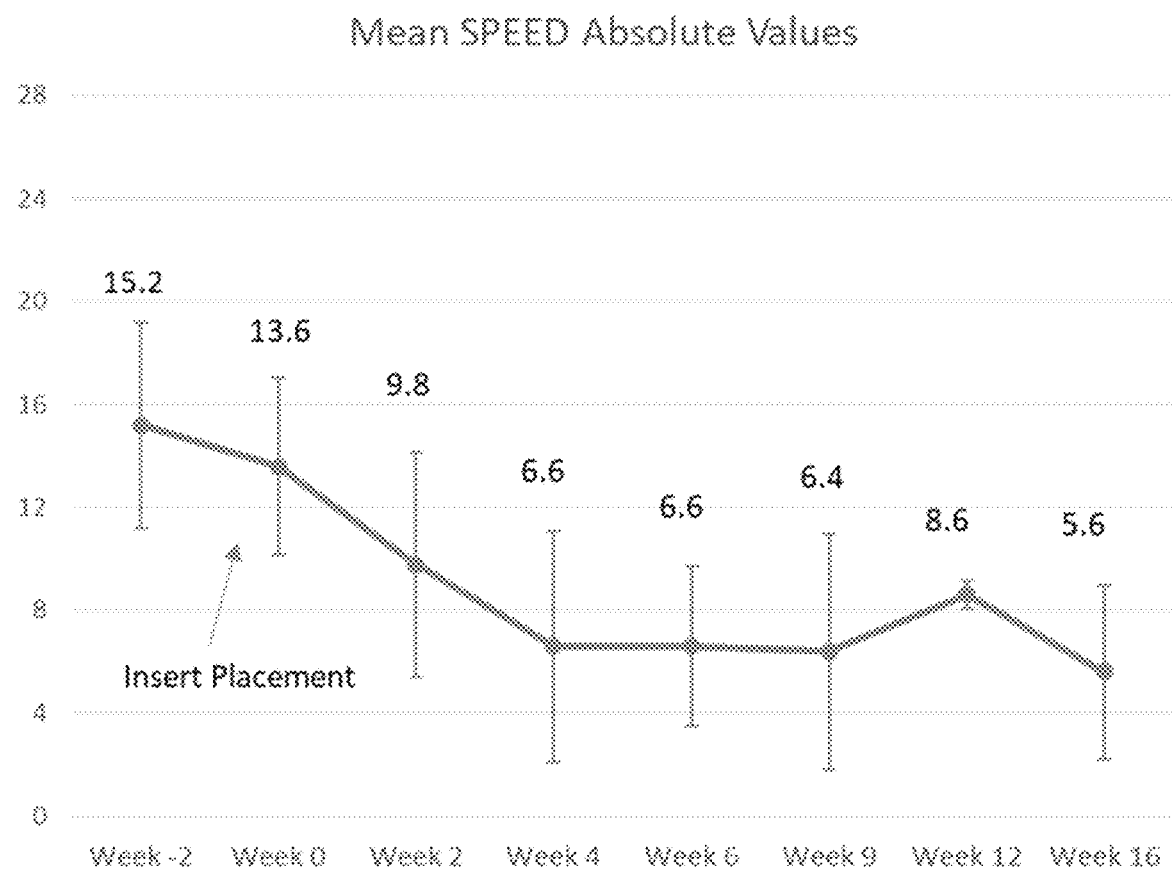
FIG. 11 depicts the results of SPEED score in terms of mean absolute values followed over time of Example 4.1.

In addition, both the ocular surface disease index (OSDI) and standard patient evaluation of eye dryness (SPEED) score decreased across the 16-week period (See FIGS. 10 and 11).

Example 4.2: Cohort 2—Randomized, Multi-Center, Double-Masked, Vehicle-Controlled, Phase 2 Study Cohort 2 is an ongoing randomized double-masked vehicle-controlled phase 2 study intended to evaluate safety, tolerability and efficacy of the hydrogel/cyclosporine insert, and treatment assignment was masked to subjects as well as investigators and their staff and Sponsor's personnel, and the study schedule as outlined above under 1. Study Schedule was followed.

A randomization schedule was computer-generated by a qualified biostatistician independent of the study conduct or project team and the hydrogel/cyclosporine as well as HV inserts administered to subjects at randomization in the double-masked treatment phase was comparable in appearance. Study subjects as well as investigators and their staff are masked to the identity of treatment until the final database is locked, and the Sponsor's personnel involved with the conduct and monitoring of the study remains masked until completion of the study and database lock.

At visit 2, the 140 enrolled subjects in Cohort 2 received one of the inserts (Formulations 1, 2A, 2B and 3) in accordance with the randomization schedule at Visit 2, after eligibility was confirmed. The procedure as outlined above under 11. Insert placement was followed for insert administration.

If unmasking is required, the integrity of the study assessments and objectives are maintained by limiting access to the unmasked data to two individuals (Sponsor Medical Monitor and Sponsor Statistician) who are not involved in the study conduct or directly by the investigator if required in an emergency.

IV. Safety and Tolerability

Adverse events including the occurrence of stinging, irritation, blurred vision or tearing were continuously assessed.

V. Durability

The durability of the inserts is assessed by monitoring the presence of the inserts.

VI. Biological Activity/Efficacy

Efficacy of the insert treatment is evaluated based on the ophthalmic assessments conducted at each visit. The efficacy endpoints are determined as follows:
Primary Endpoint
    Change from baseline (CFB) and absolute value at week 12 in Schirmer's test (unanesthetized)
Secondary Endpoints
Signs:
    Percent of subjects with ≥10 mm increase in Schirmer's score at Week 12
    CFB and absolute values of total Corneal Fluorescein Staining (tCFS) using NEI scale at each post-baseline study visit
    CFB and absolute values of Corneal Fluorescein Staining sub-regions using NEI scale, at each post-baseline visit.
    CFB and absolute values of Conjunctival Lissamine Green Staining using NEI Scale, at each post-baseline visit.
Symptoms (Subject-reported):
    CFB and absolute values of Eye Dryness Score (VAS) at each post-baseline study visit
    CFB and absolute values of Ocular Surface Disease Index (OSDI© total score, each of the three domains, and individual questions), at each post-baseline visit.
    CFB of SPEED questionnaire (overall score and individual questions), at each post-baseline visit.
Exploratory:
    CFB of Tear Film Break Up Time (TBUT) at Week 12
    Presence of insert at all post-baseline visits
    Ease of insertion as assessed by the Investigator
    Ease of visualization as assessed by the Investigator While having described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

Throughout this application various references are cited. The disclosures of these references are hereby incorporated by reference into the present disclosure.

The Invention Relates in Particular to the Following Further Embodiments

1. A sustained release biodegradable intracanalicular insert comprising a hydrogel and cyclosporine, wherein the cyclosporine is in the form of particles and wherein the cyclosporine particles are dispersed within the hydrogel.
2. The sustained release biodegradable intracanalicular insert of Embodiment 1, wherein the cyclosporine particles are uniformly dispersed within the hydrogel.
3. The sustained release biodegradable intracanalicular insert of Embodiment 1 or 2, wherein the cyclosporine particles have a d50 value of less than about 50 μm.
4. The sustained release biodegradable intracanalicular insert of Embodiment 3, wherein the cyclosporine particles have a d50 value ranging from 3 to 17 sm.
5. The sustained release biodegradable intracanalicular insert of Embodiment 4, wherein the cyclosporine particles have a d50 value ranging from 4 to 12 μm.
6. The sustained release biodegradable intracanalicular insert of Embodiment 5, wherein the cyclosporine particles have a d50 value ranging from 5 to 8 μm.
7. The sustained release biodegradable intracanalicular insert of any one of Embodiments 1 to 6, wherein the cyclosporine particles have a d90 value of less than 43 μm.
8. The sustained release biodegradable intracanalicular insert of any one of Embodiments 1 to 7, wherein the cyclosporine particles have a d100 value of less than 45 μm.

9. The sustained release biodegradable intracanalicular insert of any one of Embodiments 1 to 8, comprising the cyclosporine in an amount ranging from about 100 μg to about 800 μg.
10. The sustained release biodegradable intracanalicular insert of Embodiment 9, comprising the cyclosporine in an amount ranging from 100 μg to 300 μg.
11. The sustained release biodegradable intracanalicular insert of Embodiment 9, comprising the cyclosporine in an amount ranging from 300 μg to 450 μg.
12. The sustained release biodegradable intracanalicular insert of Embodiment 9, comprising the cyclosporine in an amount ranging from about 500 μg to about 800 μg.
13. The sustained release biodegradable intracanalicular insert of Embodiment 9, comprising the cyclosporine in an amount of about 250 μg.
14. The sustained release biodegradable intracanalicular insert of Embodiment 9, comprising the cyclosporine in an amount of about 360 μg.
15. The sustained release biodegradable intracanalicular insert of Embodiment 9, comprising the cyclosporine in an amount of about 600 μg.
16. The sustained release biodegradable intracanalicular insert of Embodiment 9, comprising the cyclosporine in an amount of about 670 μg.
17. The sustained release biodegradable intracanalicular insert of any one of Embodiments 1 to 16, wherein the insert is for insertion into the lower and the upper canaliculus.
18. The sustained release biodegradable intracanalicular insert of any one of Embodiments 1 to 16, wherein the insert is for insertion into the lower canaliculus.
19. The sustained release biodegradable intracanalicular insert of any one of Embodiments 1 to 16, wherein the insert is for insertion into the upper canaliculus.
20. The sustained release biodegradable intracanalicular insert of any one of Embodiments 17 to 19, wherein the insert is for insertion into the vertical part of the canaliculus.
21. The sustained release biodegradable intracanalicular insert of any one of Embodiments 1 to 20, wherein the insert is in a dried state prior to insertion and becomes hydrated once inserted into the eye.
22. The sustained release biodegradable intracanalicular insert of any one of Embodiments 1 to 21, wherein the hydrogel comprises a polymer network.
23. The sustained release biodegradable intracanalicular insert of Embodiment 22, wherein the hydrogel comprises a polymer network comprising one or more units of polyethylene glycol, polyethylene oxide, polypropylene oxide, polyvinyl alcohol, poly (vinylpyrrolidinone), polylactic acid, polylactic-co-glycolic acid, random or block copolymers or combinations or mixtures of any of these, or one or more units of polyaminoacids, glycosaminoglycans, polysaccharides, or proteins.
24. The sustained release biodegradable intracanalicular insert of Embodiment 22 or 23, wherein the hydrogel comprises a polymer network that comprises crosslinked polymer units that are identical or different.
25. The sustained release biodegradable intracanalicular insert of Embodiment 24, wherein the crosslinked polymer units are one or more crosslinked polyethylene glycol units.
26. The sustained release biodegradable intracanalicular insert of any one of Embodiments 22 to 25, wherein the polymer network comprises polyethylene glycol units having an average molecular weight in the range from about 2,000 to about 100,000 Daltons.
27. The sustained release biodegradable intracanalicular insert of Embodiment 26, wherein the polyethylene glycol units have an average molecular weight in the range from about 10,000 to about 60,000 Daltons.
28. The sustained release biodegradable intracanalicular insert of Embodiment 27, wherein the polyethylene glycol units have an average molecular weight in the range from about 20,000 to about 40,000 Daltons.
29. The sustained release biodegradable intracanalicular insert of Embodiment 28, wherein the polyethylene glycol units have an average molecular weight of about 20,000 Daltons.
30. The sustained release biodegradable intracanalicular insert of any one of Embodiments 22 to 29, wherein the polymer network comprises one or more crosslinked multi-arm polymer units.
31. The sustained release biodegradable intracanalicular insert of Embodiment 30, wherein the multi-arm polymer units comprise one or more 2- to 10-arm polyethylene glycol units.
32. The sustained release biodegradable intracanalicular insert of Embodiment 31, wherein the multi-arm polymer units comprise one or more 4- to 8-arm polyethylene glycol units.
33. The sustained release biodegradable intracanalicular insert of Embodiment 32, wherein the multi-arm polymer units comprise one 4-arm polyethylene glycol units.
34. The sustained release biodegradable intracanalicular insert of Embodiment 33, wherein the four arms of the 4-arm polyethylene glycol units are connected to a core molecule of pentaerythritol.
35. The sustained release biodegradable intracanalicular insert of any one of Embodiments 22 to 34, wherein the polymer network further comprises one or more cross-linking units.
36. The sustained release biodegradable intracanalicular insert of any one of Embodiments 22 to 35, wherein the polymer network is formed by reacting an electrophilic group-containing multi-arm-polymer precursor with a nucleophilic group-containing cross-linking agent.
37. The sustained release biodegradable intracanalicular insert of Embodiment 36, wherein the electrophilic group is an activated ester group.
38. The sustained release biodegradable intracanalicular insert of Embodiment 37, wherein the electrophilic group is an N-hydroxysuccinimidyl (NHS) ester group.
39. The sustained release biodegradable intracanalicular insert of Embodiment 38, wherein the electrophilic group is selected from the group consisting of succinimidylmalonate group, succinimidylsuccinate (SS) group, succinimidylmaleate group, succinimidylfumarate group, succinimidylglutarate (SG) group, succinimidyladipate (SAP) group, succinimidylpimelate group, succinimidylsuberate group and succinimidylazelate (SAZ) group.
40. The sustained release biodegradable intracanalicular insert of any one of Embodiments 36 to 39, wherein the nucleophilic group-containing crosslinking agent is nucleophilic group-containing multi-arm polymer precursor.
41. The sustained release biodegradable intracanalicular insert of any one of Embodiments 36 to 39, wherein the nucleophilic group-containing crosslinking agent is an amine.
42. The sustained release biodegradable intracanalicular insert of Embodiment 41, wherein the nucleophilic group-containing crosslinking agent is a small molecule amine with a molecular weight below 1,000 Da, comprising two or more primary aliphatic amine groups.
43. The sustained release biodegradable intracanalicular insert of Embodiment 42, wherein the nucleophilic group-containing crosslinking agent is a small molecule amine selected from the group consisting of dilysine, trilysine, tetralysine, ethylenediamine, 1,3-diaminopropane, 1,3-diaminopropane, diethylenetriamine, and trimethylhexamethylenediamine.
44. The sustained release biodegradable intracanalicular insert of Embodiment 43, wherein the nucleophilic group-containing crosslinking agent is a trilysine.
45. The sustained release biodegradable intracanalicular insert of Embodiment 44, wherein the nucleophilic group-containing crosslinking agent is trilysine acetate.
46. The sustained release biodegradable intracanalicular insert of Embodiment 44, wherein the nucleophilic group-containing crosslinking agent is a labeled trilysine.
47. The sustained release biodegradable intracanalicular insert of Embodiment 46, wherein the trilysine is labeled with a visualization agent.
48. The sustained release biodegradable intracanalicular insert of Embodiment 47, wherein the trilysine is labeled with a visualization agent selected from the group consisting of a fluorophore such as fluorescein, rhodamine, coumarin, and cyanine.
49. The sustained release biodegradable intracanalicular insert of Embodiment 48, wherein the nucleophilic group-containing crosslinking agent is fluorescein-conjugated trilysine.
50. The sustained release biodegradable intracanalicular insert of Embodiment 49, wherein the fluorescein-conjugated trilysine is obtained by reacting trilysine acetate with N-hydroxysuccinimide (NHS)-fluorescein.
51. The sustained release biodegradable intracanalicular insert of any one of Embodiments 46 to 50, wherein the trilysine is labeled by partial conjugation with a visualization agent.
52. The sustained release biodegradable intracanalicular insert of Embodiment 51, wherein about 1% to about 20% of the trilysine amine groups are conjugated with a visualization agent.
53. The sustained release biodegradable intracanalicular insert of Embodiment 52, wherein 5% to 10% of the trilysine amine groups are conjugated with a visualization agent.
54. The sustained release biodegradable intracanalicular insert of Embodiment 53, wherein 8% of the trilysine amine groups are conjugated with a visualization agent.
55. The sustained release biodegradable intracanalicular insert of any one of Embodiments 30 to 54, wherein the multi-arm polymer units comprise 4a20 kPEG units and the cross-linking units comprise fluorescein-conjugated trilysine amide units.
56. The sustained release biodegradable intracanalicular insert of any one of Embodiments 22 to 55, wherein the polymer network is obtained by reacting 4a20 kPEG-SG with fluorescein-conjugated trilysine in a molar ratio ranging from about 1:2 to about 2:1.
57. The sustained release biodegradable intracanalicular insert of Embodiment 56, wherein the polymer network is obtained by reacting 4a20 kPEG-SG with fluorescein-conjugated trilysine in a molar ratio of about 1:1.
58. The sustained release biodegradable intracanalicular insert of any one of Embodiments 22 to 55, wherein the polymer network is obtained by reacting 4a20 kPEG-SAP with fluorescein-conjugated trilysine in a molar ratio ranging from about 1:2 to about 2:1.
59. The sustained release biodegradable intracanalicular insert of Embodiment 58, wherein the polymer network is obtained by reacting 4a20 kPEG-SAP with fluorescein-conjugated trilysine in a molar ratio of about 1:1.
60. The sustained release biodegradable intracanalicular insert of any one of Embodiments 1 to 59, wherein the insert in a dried state contains from about 15% to about 80% by weight of the cyclosporine based on the total weight of the insert and from about 20% to about 60% by weight polymer units based on the total weight of the insert.
61. The sustained release biodegradable intracanalicular insert of Embodiment 60, wherein the insert in a dried state contains from 30% to 65% by weight of the cyclosporine based on the total weight of the insert and from 25% to 50% by weight polymer units based on the total weight of the insert.
62. The sustained release biodegradable intracanalicular insert of Embodiment 61, wherein the insert in a dried state contains from 45% to 55% by weight of the cyclosporine based on the total weight of the insert and from 37% to 47% by weight polymer units based on the total weight of the insert.
63. A sustained release biodegradable intracanalicular insert comprising a hydrogel and cyclosporine, wherein the insert in a dried state contains from about 40% to about 80% by weight of the cyclosporine based on the total weight of the insert.
64. The sustained release biodegradable intracanalicular insert of any one of Embodiments 1 to 63, wherein the insert in a dried state contains from 45% to 55% by weight of the cyclosporine based on the total weight of the insert.
65. The sustained release biodegradable intracanalicular insert of any one of Embodiments 1 to 64, wherein the insert in a dried state contains from about 20% to about 60% by weight polymer units based on the total weight of the insert.
66. The sustained release biodegradable intracanalicular insert of Embodiment 65, wherein the insert in a dried state contains from 25% to 50% by weight polymer units based on the total weight of the insert.
67. The sustained release biodegradable intracanalicular insert of Embodiment 66, wherein the insert in a dried state contains from 37% to 47% by weight polymer units based on the total weight of the insert.
68. The sustained release biodegradable intracanalicular insert of any one of Embodiments 1 to 67, wherein the insert contains a surfactant.
69. A sustained release biodegradable intracanalicular insert comprising a hydrogel and cyclosporine, wherein the insert contains a surfactant.
70. The sustained release biodegradable intracanalicular insert of Embodiment 68 or 69, wherein the insert in a dried state contains from about 0.01% to about 5% by weight of a surfactant based on the total weight of the insert.
71. The sustained release biodegradable intracanalicular insert of Embodiment 70, wherein the insert in a dried state contains from 0.2% to 2% by weight of a surfactant based on the total weight of the insert.
72. The sustained release biodegradable intracanalicular insert of any one of Embodiments 68 to 71, wherein the insert contains a non-ionic surfactant.

73. The sustained release biodegradable intracanalicular insert of Embodiment 72, wherein the insert contains a non-ionic surfactant comprising a poly(ethylene glycol) chain.

74. The sustained release biodegradable intracanalicular insert of Embodiment 73, wherein the insert contains a surfactant selected from the group consisting of poly(ethylene glycol) sorbitan monolaurate, poly(ethylene glycol) ester of castor oil, and an ethoxylated 4-tert-octylphenol/formaldehyde condensation polymer.

75. The sustained release biodegradable intracanalicular insert of Embodiment 74, wherein the surfactant is selected from the group consisting of poly(ethylene glycol)-20-sorbitan monolaurate, poly(ethylene glycol)-80-sorbitan monolaurate, poly(ethylene glycol)-35 ester of castor oil and an ethoxylated 4-tert-octylphenol/formaldehyde condensation polymer.

76. The sustained release biodegradable intracanalicular insert of Embodiment 75, wherein the insert contains an ethoxylated 4-tert-octylphenol/formaldehyde condensation polymer.

77. The sustained release biodegradable intracanalicular insert of any one of Embodiments 1 to 76, wherein the insert contains one or more phosphate, borate or carbonate salt(s).

78. The sustained release biodegradable intracanalicular insert of Embodiment 77, wherein the insert contains phosphate salt originating from phosphate buffer used during the preparation of the hydrogel.

79. The sustained release biodegradable intracanalicular insert of any one of Embodiments 1 to 78, wherein the insert in a dried state contains not more than about 1% by weight water based on the total weight of the insert.

80. The sustained release biodegradable intracanalicular insert of any one of Embodiments 1 to 79, wherein the insert has an essentially cylindrical shape with an essentially round cross-section.

81. The sustained release biodegradable intracanalicular insert of any one of Embodiments 1 to 80, wherein the cyclosporine content as measured by HPLC after at least 3 months of storage at a temperature of from 2 to 8° C. is from about 300 to about 410 sg.

82. The sustained release biodegradable intracanalicular insert of any one of Embodiments 1 to 81, wherein the cyclosporine content as measured by HPLC after at least 6 months of storage at a temperature of from 2 to 8° C. is from about 300 to about 410 µg.

83. The sustained release biodegradable intracanalicular insert of any one of Embodiments 1 to 82, wherein the cyclosporine content as measured by HPLC after at least 12 months of storage at a temperature of from 2 to 8° C. is from about 300 to about 410 sg.

84. The sustained release biodegradable intracanalicular insert of any one of Embodiments 1 to 83, wherein the cyclosporine content as measured by HPLC after at least 3 months of storage at a temperature of from 2 to 8° C. is from about 90 to about 110% by weight. [1 have kept more of the ranges in the specification]

85. The sustained release biodegradable intracanalicular insert of any one of Embodiments 1 to 84, wherein the cyclosporine content as measured by HPLC after at least 6 months of storage at a temperature of from 2 to 8° C. is from about 90 to about 110% by weight.

86. The sustained release biodegradable intracanalicular insert of any one of Embodiments 1 to 85, wherein the cyclosporine content as measured by HPLC after at least 12 months of storage at a temperature of from 2 to 8° C. is from about 90 to about 110% by weight.

87. The sustained release biodegradable intracanalicular insert of any one of Embodiments 1 to 86, wherein the amount of impurities as measured by HPLC after at least 3 months of storage at a temperature of from 2 to 8° C. is not more than 3.0%.

88. The sustained release biodegradable intracanalicular insert of any one of Embodiments 1 to 87, wherein the amount of impurities as measured by HPLC after at least 6 months of storage at a temperature of from 2 to 8° C. is not more than 3.0%.

89. The sustained release biodegradable intracanalicular insert of any one of Embodiments 1 to 88, wherein the amount of impurities as measured by HPLC after at least 12 months of storage at a temperature of from 2 to 8° C. is not more than 3.0%.

90. The sustained release biodegradable intracanalicular insert of any one of Embodiments 1 to 89, wherein the insert is in the form of a fiber.

91. The sustained release biodegradable intracanalicular insert of Embodiment 90, wherein the insert is in the form of a fiber that has an average length of about 1.5 mm to about 4.0 mm and an average diameter of not more than 0.8 mm in its dried state.

92. The sustained release biodegradable intracanalicular insert of Embodiment 91, wherein the insert is in the form of a fiber that has an average length of 2.0 mm to 2.5 mm and an average diameter of not more than 0.62 mm in its dried state.

93. The sustained release biodegradable intracanalicular insert of Embodiment 92, wherein the insert is in the form of a fiber that has an average length of 2.5 mm to 2.9 mm and an average diameter of not more than 0.62 mm in its dried state.

94. The sustained release biodegradable intracanalicular insert of any one of Embodiments 1 to 93, wherein the insert after at least 3 months of storage at a temperature of from 2 to 8° C. is in the form of a fiber that has an average length of about 2.5 mm to about 2.9 mm and an average diameter of not more than 0.62 mm in its dried state.

95. The sustained release biodegradable intracanalicular insert of any one of Embodiments 1 to 94, wherein the insert after at least 6 months of storage at a temperature of from 2 to 8° C. is in the form of a fiber that has an average length of about 2.5 mm to about 2.9 mm and an average diameter of not more than 0.62 mm in its dried state.

96. The sustained release biodegradable intracanalicular insert of any one of Embodiments 1 to 95, wherein the insert after at least 12 months of storage at a temperature of from 2 to 8° C. is in the form of a fiber that has an average length of about 2.5 mm to about 2.9 mm and an average diameter of not more than 0.62 mm in its dried state.

97. The sustained release biodegradable intracanalicular insert of any one of Embodiments 1 to 96, wherein the insert is in the form of a fiber that has an average diameter of at least 1.0 mm in expanded state after 10 minutes of hydration in vitro in phosphate-buffered saline at a pH of 7.4 at 37° C.

98. The sustained release biodegradable intracanalicular insert of any one of Embodiments 1 to 97, wherein the insert is in the form of a fiber that has an average diameter of at least 1.3 mm in equilibrium state after 24 hours of hydration in vitro in phosphate-buffered saline at a pH of 7.4 at 37° C.

99. The sustained release biodegradable intracanalicular insert of any one of Embodiments 1 to 98, wherein the insert is inserted into the canaliculus with the aid of a grasping device selected from the group consisting of a forceps, a tweezer, and an applicator.

100. The sustained release biodegradable intracanalicular insert of any one of Embodiments 1 to 99, wherein upon hydration in vivo in the eye or in vitro the diameter of the insert is increased, or the length of the insert is decreased while its diameter is increased.

101. The sustained release biodegradable intracanalicular insert of Embodiment 100, wherein hydration is measured in vitro in phosphate-buffered saline at a pH of 7.4 at 37° C. after 24 hours.

102. The sustained release biodegradable intracanalicular insert of any one of Embodiments 1 to 101, wherein the insert disintegrates in the canaliculus within about 1 to about 6 months after insertion.

103. The sustained release biodegradable intracanalicular insert of Embodiment 102, wherein the insert disintegrates in the canaliculus within 2 to 4 months after insertion.

104. The sustained release biodegradable intracanalicular insert of Embodiment 103, wherein the insert disintegrates in the canaliculus within 2 to 3 months after insertion.

105. The sustained release biodegradable intracanalicular insert of Embodiment 103, wherein the insert disintegrates in the canaliculus within 3 to 4 months after insertion.

106. The sustained release biodegradable intracanalicular insert of any one of Embodiments 1 to 105, wherein the insert after insertion to the canaliculus releases a therapeutically effective amount of cyclosporine over a period of at least about 1 month after insertion.

107. The sustained release biodegradable intracanalicular insert of Embodiment 106, wherein the insert after insertion to the canaliculus releases a therapeutically effective amount of cyclosporine over a period of at least 2 months after insertion.

108. The sustained release biodegradable intracanalicular insert of Embodiment 107, wherein the insert after insertion to the canaliculus releases a therapeutically effective amount of cyclosporine over a period of at least 3 months after insertion.

109. The sustained release biodegradable intracanalicular insert of any one of Embodiments 1 to 108, wherein cyclosporine is released from the insert after insertion to a human subject at an average rate of about 0.1 µg/day to about 10 µg/day.

110. The sustained release biodegradable intracanalicular insert of any one of Embodiments 1 to 108, wherein cyclosporine is released from the insert after insertion at an average rate of about 0.1 µg/day to about 10 µg/day.

111. The sustained release biodegradable intracanalicular insert of Embodiment 109 or 110, wherein cyclosporine is released from the insert after insertion at an average rate of 1 µg/day to 5 µg/day.

112. The sustained release biodegradable intracanalicular insert of Embodiment 111, wherein cyclosporine is released from the insert after insertion at an average rate of 2 µg/day to 4 µg/day.

113. The sustained release biodegradable intracanalicular insert of any one of Embodiments 1 to 112, wherein the tear fluid concentration of cyclosporine after insertion to a human subject ranges from about 0.1 µg/mL to about 10 µg/mL.

114. The sustained release biodegradable intracanalicular insert of any one of Embodiments 1 to 112, wherein the tear fluid concentration of cyclosporine after insertion of the insert ranges from about 0.1 µg/mL to about 10 µg/mL.

115. The sustained release biodegradable intracanalicular insert of Embodiment 113 or 114, wherein the tear fluid concentration of cyclosporine after insertion of the insert ranges from about 1 µg/mL to about 5 µg/mL.

116. The sustained release biodegradable intracanalicular insert of any one of Embodiments 1 to 115, wherein the insert disintegrates in the canaliculus prior to complete solubilization of the cyclosporine particles contained in the insert.

117. The sustained release biodegradable intracanalicular insert of any one of Embodiments 1 to 116, wherein the insert is obtainable by preparing a precursor mixture containing hydrogel precursors and cyclosporine, filling the precursor mixture into a tubing, allowing the hydrogel precursors to cross-link in the tubing to provide a hydrogel mixture shaped as a fiber, and stretching the hydrogel mixture fiber to provide the insert.

118. The sustained release biodegradable intracanalicular insert of any one of Embodiments 1 to 117, wherein the fiber has been stretched prior to or after drying.

119. The sustained release biodegradable intracanalicular insert of Embodiment 118, wherein the fiber has been stretched prior to drying.

120. A sustained release biodegradable intracanalicular insert comprising a hydrogel and cyclosporine in the form of a fiber, wherein the fiber has been stretched.

121. The sustained release biodegradable intracanalicular insert of any one of Embodiments 118 to 120, wherein the fiber has been stretched by a stretch factor in the longitudinal direction of from about 1.0 to about 4.0.

122. The sustained release biodegradable intracanalicular insert of Embodiment 121, wherein the fiber has been stretched by a stretch factor in the longitudinal direction of from about 1.5 to about 3.0.

123. The sustained release biodegradable intracanalicular insert of Embodiment 122, wherein the fiber has been stretched by a stretch factor in the longitudinal direction of about 2.7.

124. A sustained release biodegradable intracanalicular insert comprising a hydrogel and cyclosporine in an amount of about 360 µg dispersed within the hydrogel, wherein the hydrogel comprises a polymer network comprising polyethylene glycol units, and wherein the insert is in a dried state prior to insertion.

125. A sustained release biodegradable intracanalicular insert comprising a hydrogel and cyclosporine in an amount of about 360 µg, in the form of a fiber that has an average length of about 2.5 mm to about 2.9 mm and an average diameter of not more than 0.62 mm in its dried state.

126. A sustained release biodegradable intracanalicular insert comprising a hydrogel and from about 45% to about 55% by weight of cyclosporine based on the total weight of the insert, in the form of a fiber that has an average length of about 2.5 mm to about 2.9 mm and an average diameter of not more than 0.62 mm in its dried state.

127. A sustained release biodegradable intracanalicular insert comprising a hydrogel and cyclosporine in an amount of about 360 µg dispersed within the hydrogel, wherein the insert after insertion to the canaliculus releases a therapeutically effective amount of cyclosporine over a period of at least about 3 months after insertion.

128. A sustained release biodegradable intracanalicular insert comprising a hydrogel and cyclosporine, wherein the cyclosporine is in the form of particles
the cyclosporine particles are dispersed within the hydrogel and have a d50 value of less than about 50 µm, and wherein
the cyclosporine is released from the insert after insertion to a human subject at an average rate of about 0.1 µg/day to about 10 µg/day.

129. A sustained release biodegradable intracanalicular insert comprising
a hydrogel comprising a polymer network, the polymer network comprising
one or more crosslinked multi-arm polymer units comprising about 300 µg 4a20K PEG units and
cross-linking units comprising fluorescein-conjugated trilysine amide units, and and cyclosporine in an amount of about 360 µg,
in the form of a fiber that has an average length of about 2.5 mm to about 2.9 mm and an average diameter of not more than 0.62 mm in its dried state.

130. A sustained release biodegradable intracanalicular insert comprising
a hydrogel comprising a polymer network obtained by reacting 4a20 kPEG-SG with fluorescein-conjugated trilysine in a molar ratio of about 1:1
and cyclosporine in an amount of about 360 µg,
in the form of a fiber that has an average length of about 2.5 mm to about 2.9 mm and an average diameter of not more than 0.62 mm in its dried state.

131. A sustained release biodegradable intracanalicular insert comprising
a hydrogel comprising a polymer network obtained by reacting 4a20 kPEG-SAP with fluorescein-conjugated trilysine in a molar ratio of about 1:1
and cyclosporine in an amount of about 360 µg,
in the form of a fiber that has an average length of about 2.5 mm to about 2.9 mm and an average diameter of not more than 0.62 mm in its dried state.

132. The sustained release biodegradable intracanalicular insert of any one of Embodiments 1 to 131, wherein the hydrogel comprises a polymer network which is semi-crystalline in the dry state at or below room temperature, and amorphous in the wet state.

133. The sustained release biodegradable intracanalicular insert of any one of Embodiments 1 to 132, wherein the insert has undergone wet or dry stretching during manufacture, and wherein the insert in the stretched form is dimensionally stable when in the dry state at or below room temperature.

134. A method of treating or preventing an ocular disease in a subject in need thereof, the method comprising inserting into the canaliculus of the subject a first sustained release biodegradable intracanalicular insert comprising a hydrogel and a cyclosporine according to any one of Embodiments 1 to 132.

135. The method of Embodiment 134, wherein said first insert is left to remain in the canaliculus until complete disintegration.

136. The method of Embodiment 134 or 135, wherein said first insert is designed to disintegrate in the canaliculus within about 3 to about 4 months after insertion.

137. The method of any one of Embodiments 134 to 136, wherein a second insert is inserted after at least 2 months without prior removal of said first insert.

138. A method of treating dry eye disease in a subject, the method comprising the steps of;
(a) inserting a first biodegradable insert into a first canaliculus of a first eye of the subject, wherein the insert comprises:
(1) a hydrogel;
(2) from about 100 µg to about 800 µg cyclosporine dispersed in the hydrogel;
(3) wherein the cyclosporine releases from the insert over a period of at least about 2-months from the date of inserting the first insert in the subject, at an average rate of about 0.1 µg/day to about 10 µg/day; and
(b) after at least about 2-months from the date of inserting the first insert, inserting a second insert into the first canaliculus of the first eye in the subject, wherein the second insert is substantially similar to the first insert.

139. The method of Embodiment 138, wherein said first insert is removed prior to complete disintegration.

140. The method of Embodiment 139, wherein said first insert is removed prior to complete disintegration and a second insert is inserted to replace the removed first insert.

141. The method of any one of Embodiments 138 to 140, wherein said first insert is designed to disintegrate in the canaliculus within about 2 to about 3 months after insertion.

142. The method of any one of Embodiments 134 to 141, wherein said first insert is left to remain in the canaliculus until complete disintegration.

143. The method of any one of Embodiments 134 to 142, wherein a second insert is inserted after at least 2 months without prior removal of said first insert.

144. The method of any one of Embodiments 134 to 142, wherein said first insert is removed prior to complete disintegration and a second insert is inserted to replace the removed first insert.

145. The method of any one of Embodiments 134 to 142, wherein said first insert is designed to disintegrate in the canaliculus within about 2 to about 3 months after insertion and wherein said first insert is removed within 2 months after insertion.

146. The method of any one of Embodiments 134 to 145, wherein the dose per eye administered once for a treatment period of at least 2 months is from about 300 µg to about 400 µg of the cyclosporine.

147. The method of any one of Embodiments 134 to 146, wherein the ocular disease is a disorder of the tear film and ocular surface.

148. The method of any one of Embodiments 134 to 146, wherein the ocular disease is dry eye disease.

149. The method of any one of Embodiments 134 to 146, wherein the ocular disease is associated with one or more conditions selected from the group consisting of burning sensation, itching, redness, singing, pain, foreign body sensation, visual disturbances, inflammation of the lacrimal gland, inflammation of the ocular surface, T-cell-mediated inflammation, presence of conjunctival T-cells in the tears and elevated levels of inflammatory cytokines in the tears.

150. The method of any one of Embodiments 134 to 149, wherein the treatment is effective in improving tear production as measured by Schirmer's tear test in a subject with a Schirmer's score of less than 10 mm prior to insertion of the insert.
151. The method of any one of Embodiments 134 to 150, wherein the treatment is effective in reducing eye dryness symptoms as determined by one or more assessments selected from the group consisting of rating of the severity of symptoms of eye dryness on a visual anaolgue scale, rating of the frequency of symptoms of eye dryness on a visual anaolgue scale, determination of tear film break up time, Corneal Fluorescein Staining, Conjunctival Lissamine Green Staining, best corrected visual acuity, determination of ocular surface disease index and standard patient evaluation of eye dryness.
152. The method of any one of Embodiments 134 to 151, wherein the dose per eye administered once for the treatment period is contained in one insert.
153. The method of any one of Embodiments 134 to 151, wherein the dose per eye administered once for the treatment period is contained in two inserts.
154. The method of any one of Embodiments 134 to 153, wherein the insert is inserted into the lower canaliculus.
155. The method of any one of Embodiments 134 to 154, wherein the treatment period is at least 1 month, at least 2 months or at least 3 months.
156. A method of treating dry eye disease in a subject in need thereof, the method comprising inserting to the canaliculus of a subject a sustained release biodegradable intracanalicular insert comprising a hydrogel and cyclosporine, wherein punctal occlusion and cyclosporine release to the eye provide a synergistic effect.
157. The method of Embodiment 156, wherein the synergistic effect consists in a higher bioavailability of the cyclosporine when compared to administration of eye drops containing cyclosporine designed to providing the same daily release of cyclosporine.
158. The method of Embodiment 157, wherein the higher bioavailability is determined by the amount of cyclosporine released to the tear fluid as calculated based on cyclosporine tear fluid concentration over time.
159. A method of manufacturing a sustained release biodegradable intracanalicular insert comprising a hydrogel and cyclosporine according to any one of Embodiments 1 to 133, the method comprising the steps of
a) preparing a precursor mixture containing hydrogel precursors and cyclosporine particles dispersed in the precursor mixture,
b) shaping the precursor mixture and allowing the hydrogel precursors to cross-link to form a polymer network and to obtain a shaped hydrogel mixture comprising the polymer network, and
c) drying the hydrogel mixture to provide the insert.
160. The method of Embodiment 159, wherein the cyclosporine particles are micronized particles homogeneously dispersed within the precursor mixture.
161. The method of Embodiment 159 or 160, wherein in step a) the precursor mixture is prepared by mixing an electrophilic group-containing multi-arm-polymer precursor with a nucleophilic group-containing cross-linking agent in a buffered aqueous solution in the presence of micronized cyclosporine particles.
162. The method of Embodiment 161, wherein in step a) the electrophilic group-containing multi-arm-polymer precursor is provided in a buffered aqueous precursor solution and the nucleophilic group-containing cross-linking agent is provided in a buffered aqueous precursor suspension comprising the micronized cyclosporine particles.
163. The method of Embodiment 161 or 162, wherein in step a) the buffered aqueous precursor solution is prepared by dissolving the multi-arm-polymer precursor in an aqueous buffer solution and is then mixed with the buffered aqueous precursor suspension comprising the nucleophilic group-containing cross-linking agent and micronized cyclosporine particles within 60 minutes.
164. The method of any one of Embodiments 159 to 163, wherein in step a) the precursor mixture containing cyclosporine particles is degassed under vacuum after mixing its component.
165. The method of any one of Embodiments 159 to 164, comprising reacting 4a20 kPEG-SAP with fluorescein-conjugated trilysine in a weight ratio ranging from about 30:1 to about 50:1.
166. The method of any one of Embodiments 159 to 164, comprising reacting 4a20 kPEG-SG with fluorescein-conjugated trilysine in a weight ratio ranging from about 30:1 to about 50:1.
167. The method of any one of Embodiments 159 to 166, wherein in step b) the shaping of the precursor mixture consists of filling the precursor mixture into a mold or tubing prior to complete cross-linking in order to provide the desired final shape of the hydrogel mixture and allowing the hydrogel precursors to cross-link.
168. The method of any one of Embodiments 159 to 167, wherein in step b) the precursor mixture is filled into a fine diameter tubing in order to prepare a hydrogel mixture fiber.
169. The method of Embodiment 168, wherein the inside of the tubing has a round geometry.
170. The method of Embodiment 169, wherein the inside of the tubing has a round geometry with an inner diameter of about 2.0 mm.
171. The method of Embodiment 169, wherein the inside of the tubing has a non-round geometry.
172. The method of any one of Embodiments 159 to 171, wherein the method further comprises stretching the hydrogel mixture fiber.
173. The method of Embodiment 172, wherein the stretching is performed prior to or after drying the hydrogel mixture.
174. The method of Embodiment 172 or 173, wherein the fiber is stretched by a stretch factor of about 1 to about 4.5.
175. A sustained release biodegradable intracanalicular insert obtainable by the method of any one of Embodiments 159 to 174.
176. A method of imparting shape memory to a hydrogel mixture fiber comprising cyclosporine particles dispersed in the hydrogel by stretching the hydrogel mixture fiber in the longitudinal direction.
177. Use of a sustained release biodegradable intracanalicular insert comprising a hydrogel and cyclosporine according to any one of embodiments 1 to 133 in the preparation of a medicament for the treatment of an ocular disease in a subject in need thereof according to any one of embodiments 134 to 158.
178. A sustained release biodegradable intracanalicular insert comprising a hydrogel and cyclosporine according to any one of embodiments 1 to 133 for use in the treatment of an ocular disease in a subject in need thereof according to any one of embodiments 134 to 158.
179. A method of increasing tear production as measured by Schirmer's tear test in a subject with a Schirmer's score of less than 10 mm prior to insertion of an intracanalicular insert, the method comprising administering to the subject the sustained release biodegradable intracanalicular insert comprising a hydrogel and cyclosporine according to any one of embodiments 1 to 133.

180. The method of embodiment 179, wherein the Schirmer's score increases by at least 2 mm at 6 weeks after insertion.

181. The method of embodiment 180, wherein the Schirmer's score increases by at least 3 mm at 12 weeks after insertion.

182. A method of reducing eye dryness symptoms as determined by one or more assessments selected from the group consisting of rating of the severity of symptoms of eye dryness on a visual anaolgue scale, rating of the frequency of symptoms of eye dryness on a visual anaolgue scale, determination of tear film break up time, Corneal Fluorescein Staining, Conjunctival Lissamine Green Staining, best corrected visual acuity, determination of ocular surface disease index OSDI, and standard patient evaluation of eye dryness SPEED, the method comprising administering to the subject the sustained release biodegradable intracanalicular insert comprising a hydrogel and cyclosporine according to any one of embodiments 1 to 133.

183. The method of claim 182, wherein the total Corneal Fluorescein Staining value tCFS decreases by at least 1.5 at 6 weeks after insertion.

184. The method of claim 183, wherein the total Corneal Fluorescein Staining value tCFS decreases by at least 3 at 12 weeks after insertion.

185. The method of any one of Claims 182 to 184, wherein the rating of the severity of symptoms of eye dryness on a visual analogue scale decreases by at least 10 at 2 weeks after insertion.

186. The method of claim 185, wherein the rating of the severity of symptoms of eye dryness on a visual analogue scale decreases by at least 15 at 6 weeks after insertion.

The invention claimed is:

1. An ocular composition comprising a sustained release biodegradable intracanalicular insert comprising a hydrogel and cyclosporine, wherein the cyclosporine is in the form of particles having d50 value of less than about 50 μm as measured by laser diffraction and wherein the cyclosporine particles are dispersed within the hydrogel, wherein the hydrogel comprises a polymer network comprising cross-linked polymer units that are identical or different which are polyethylene glycol units having two to ten arms, wherein the arms of the polyethylene glycol units are connected to a core molecule of pentaerythritol, the polymer network is formed by reacting an electrophilic group-containing multi-arm polymer precursor with a nucleophilic group-containing cross-linking agent, the electrophilic group is an N-hydroxysuccinimidyl (NHS) ester group, the nucleophilic group-containing crosslinking agent contains an amine group.

2. The ocular composition of claim 1, wherein the nucleophilic group-containing cross-linking agent is a small molecule amine with a molecular weight below 1,000 Da.

3. The ocular composition of claim 1, wherein the nucleophilic group-containing crosslinking agent is a labeled trilysine.

4. The ocular composition of claim 1, wherein the cyclosporine particles have a d50 value ranging from 3 to 17 μm.

5. The ocular composition of claim 1, wherein the multi-arm polymer units comprise 4a20kPEG units and the cross-linking units comprise fluorescein-conjugated trilysine amide units.

6. The ocular composition of claim 1, wherein the polymer network is obtained by reacting 4a20kPEG-SG or 4a20kPEG-SAP with fluorescein-conjugated trilysine in a molar ratio ranging from about 1:2 to about 2:1.

7. The ocular composition of claim 1, wherein the insert in a dried state contains from about 15% to about 80% by weight of the cyclosporine based on the total weight of the insert and from about 20% to about 60% by weight polymer units based on the total weight of the insert.

8. The ocular composition of claim 1, wherein the insert in a dried state contains from about 40% to about 80% by weight of the cyclosporine based on the total weight of the insert.

9. The ocular composition of claim 8, wherein the insert in a dried state contains from 45% to 55% by weight of the cyclosporine based on the total weight of the insert.

10. The ocular composition of claim 1, wherein the insert contains a surfactant.

11. The ocular composition of claim 10, wherein the insert in a dried state contains from about 0.01% to about 5% by weight of a surfactant based on the total weight of the insert.

12. The ocular composition of claim 10, wherein the insert contains a non-ionic surfactant.

13. The ocular composition of claim 1, wherein the cyclosporine content as measured by HPLC after at least 3 months at a temperature of from 2 to 8° C. is from about 300 to about 410 μg by weight.

14. The ocular composition of claim 13, wherein the amount of impurities as measured by HPLC after at least 3 months of storage at a temperature of from 2 to 8° C. is not more than 3.0%.

15. The ocular composition of claim 1, wherein the insert is in the form of a fiber, wherein the fiber has an average length of about 1.5 mm to about 4.0 mm and an average diameter of not more than 0.8 mm in its dried state.

16. The ocular composition of claim 1, wherein the insert after at least 3 months at a temperature of from 2 to 8° C. is in the form of a fiber that has an average length of about 2.5 mm to about 2.9 mm and an average diameter of not more than 0.62 mm in its dried state.

17. The ocular composition of claim 1, wherein the insert is in the form of a fiber that has an average diameter of at least 1.0 mm in expanded state after 10 minutes of hydration or of at least 1.3 mm in equilibrium state after 24 hours of hydration in vitro in phosphate-buffered saline at a pH of 7.4 at 37° C.

18. The ocular composition of claim 1, wherein the insert disintegrates in the canaliculus within about 1 to about 6 months after insertion.

19. The ocular composition of claim 18, wherein the insert after insertion to the canaliculus releases a therapeutically effective amount of cyclosporine over a period of at least about 1 month after insertion.

20. The ocular composition of claim 19, wherein cyclosporine is released from the insert after insertion to a human subject at an average rate of about 0.1 μg/day to about 10 μg/day.

* * * * *